US009187561B2

(12) United States Patent
Goldenberg et al.

(10) Patent No.: US 9,187,561 B2
(45) **Date of Patent: *Nov. 17, 2015**

(54) HUMANIZED ANTI-HLA-DR ANTIBODIES

(71) Applicant: Immunomedics, Inc., Morris Plains, NJ (US)

(72) Inventors: David M. Goldenberg, Mendham, NJ (US); Hans J. Hansen, Picayune, MS (US); Chien-Hsing Chang, Downingtown, PA (US)

(73) Assignee: Immunomedics, Inc., Morris Plains, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/224,866

(22) Filed: Mar. 25, 2014

(65) Prior Publication Data

US 2014/0227178 A1 Aug. 14, 2014

Related U.S. Application Data

(60) Division of application No. 12/754,140, filed on Apr. 5, 2010, now Pat. No. 8,722,047, which is a continuation-in-part of application No. 12/556,718, filed on Sep. 10, 2009, now Pat. No. 8,613,903, which is a division of application No. 11/368,296, filed on Mar. 3, 2006, now Pat. No. 7,612,180.

(60) Provisional application No. 60/657,695, filed on Mar. 3, 2005, provisional application No. 61/166,809, filed on Apr. 6, 2009, provisional application No. 61/168,715, filed on Apr. 13, 2009.

(51) Int. Cl.

| | |
|---|---|
| ***A61K 51/10*** | (2006.01) |
| ***A61K 39/395*** | (2006.01) |
| ***A61K 47/48*** | (2006.01) |
| ***C07K 16/28*** | (2006.01) |
| ***A61K 45/06*** | (2006.01) |
| *C07K 14/74* | (2006.01) |
| *A61K 39/00* | (2006.01) |

(52) U.S. Cl.

CPC ............ *C07K 16/28* (2013.01); *A61K 39/3955* (2013.01); *A61K 39/39558* (2013.01); *A61K 45/06* (2013.01); *A61K 47/48561* (2013.01); *A61K 51/1027* (2013.01); *A61K 51/1093* (2013.01); *C07K 16/2833* (2013.01); *C07K 16/2887* (2013.01); *A61K 2039/505* (2013.01); *A61K 2039/507* (2013.01); *C07K 2316/95* (2013.01); *C07K 2316/96* (2013.01); *C07K 2317/24* (2013.01); *C07K 2317/56* (2013.01); *C07K 2317/71* (2013.01); *C07K 2317/73* (2013.01); *C07K 2317/732* (2013.01); *C07K 2317/734* (2013.01); *C07K 2317/75* (2013.01); *C07K 2317/92* (2013.01)

(58) Field of Classification Search

None

See application file for complete search history.

(56) References Cited

U.S. PATENT DOCUMENTS

| | | | | |
|---|---|---|---|---|
| 5,530,101 | A | 6/1996 | Queen et al. | |
| 5,585,089 | A | 12/1996 | Queen et al. | |
| 5,693,762 | A | 12/1997 | Queen et al. | |
| 5,789,554 | A | 8/1998 | Leung et al. | |
| 5,792,852 | A * | 8/1998 | do Couto et al. | 536/23.53 |
| 5,859,205 | A | 1/1999 | Adair et al. | |
| 6,180,370 | B1 | 1/2001 | Queen et al. | |
| 6,180,377 | B1 | 1/2001 | Morgan et al. | |
| 6,187,287 | B1 | 2/2001 | Leung et al. | |
| 6,730,300 | B2 | 5/2004 | Leung et al. | |
| 7,022,500 | B1 | 4/2006 | Queen et al. | |
| 7,262,278 | B2 | 8/2007 | Tawara et al. | |
| 7,312,318 | B2 | 12/2007 | Hansen et al. | |
| 7,521,056 | B2 | 4/2009 | Chang et al. | |
| 7,527,787 | B2 | 5/2009 | Chang et al. | |
| 7,534,866 | B2 | 5/2009 | Chang et al. | |
| 7,550,143 | B2 | 6/2009 | Chang et al. | |
| 7,612,180 | B2 | 11/2009 | Goldenberg et al. | |
| 7,666,400 | B2 | 2/2010 | Chang et al. | |
| 2003/0103979 | A1 | 6/2003 | Leung et al. | |
| 2006/0210475 | A1 | 9/2006 | Goldenberg et al. | |
| 2009/0202487 | A1 | 8/2009 | Chang et al. | |

(Continued)

FOREIGN PATENT DOCUMENTS

WO WO 2006/094192 A2 * 9/2006

OTHER PUBLICATIONS

Brown et al (Clinical Lymphoma, 2001, 2(3): 188-190).*
Stein et al (Blood, 2010, 115(25): 5180-5190).*
Freshney (Culture of Animal Cells, A Manual of Basic Technique, Alan R. Liss, Inc., 1983, New York, p. 4).*
Dermer (Bio/Technology, 1994, 12:320).*
Zips et al (In Vivo, 2005, 19:1-7).*
Aagaard et al., "RNAi therapeutics: principles, prospects and challenges", Adv Drug Deily Rev. Mar. 30, 2007;59 (2-3):75-86.
Altomonte et al., "Targeting of HLA-DR molecules transduces agonistic functional signals in cutaneous melanoma", J Cell Physiol. 2004;200:272-276.

(Continued)

*Primary Examiner* — Gerald R Ewoldt
*Assistant Examiner* — Marianne DiBrino
(74) *Attorney, Agent, or Firm* — Richard A. Nakashima

(57) ABSTRACT

The present invention concerns compositions and methods of use of humanized anti-HLA-DR antibodies. In preferred embodiments, the antibodies induce apoptosis and inhibit proliferation of lymphoma cells without inducing CDC or ADCC. In more preferred embodiments, the humanized anti-HLA-DR antibodies bind to the same epitope of HLA-DR as, or compete for binding to HLA-DR with, a murine L243 antibody. Most preferably, the humanized anti-HLA-DR antibody exhibits a higher affinity for HLA-DR than the parental murine antibody. The humanized HLA-DR antibody is of use for therapy of various diseases such as cancer, autoimmune disease or immune dysregulatory function, and is of particular use for therapy of B cell lymphomas and leukemias. In most preferred embodiments, the humanized anti-HLA-DR antibody is capable of inducing at least partial remission of lymphomas that are resistant to other B cell antibodies, such as rituximab.

21 Claims, 28 Drawing Sheets

(56) References Cited

U.S. PATENT DOCUMENTS

| | | | |
|---|---|---|---|
| 2009/0300780 | A1 | 12/2009 | Cattaneo et al. |
| 2010/0196267 | A1 | 8/2010 | Goldenberg et al. |

OTHER PUBLICATIONS

Aoudjit et al., "HLA-DR signaling inhibits Fas-mediated apoptosis in A375 melanoma cells", Exp Cell Res. 2004;299:79-90.

Blancheteau et al., "HLA class II signals sensitize B lymphocytes to apoptosis via Fas/CD95 by increasing FADD recruitment to activated Fas and activation of caspases", Hum Immunol. 2002;63:375-383.

Bridges et al., "Selective in vivo antitumor effects of monoclonal anti-I-A antibody on a B lymphoma", J Immunol. 1987;139:4242-4249.

Brozek et al., "Anti-DR antibodies inhibit in vitro production of human rheumatoid factor", J Clin Lab Immunol. 1990;31:105-109.

Elsasser et al., "HLA class II as potential target antigen on malignant B cells for therapy with bispecific antibodies in combination with granulocyte colony-stimulating factor", Blood 1996;87:3803-3812.

Fu et al., "HLA-DR alpha chain residues located on the outer loops are involved in non-polymorphic and polymorphic antibody-binding epitopes", Hum Immunol. 1994; 39:253-260.

Gussow et al., "Humanization of monoclonal antibodies", Method Enzymol. 203:99-121, (1991).

Kabelitz et al., "Growth inhibition of Epstein-Barr virus-transformed B cells by anti-HLA-DR antibody L243: possible relationship to L243-induced down-regulation of CD23 antigen expression", Cell Immunol. 1989;120:21-30.

Lampson et al., "Two populations of la-like molecules on a human B cell line", J. Immunol. (1980) 125:293-299.

Lund et al., "Expression and characterization of truncated forms of humanized L243 IgG1. Architectural features can influence synthesis of its oligosaccharide chains and affect superoxide production triggered through human Fcgamma receptor I", Eur. J. Biochem. Dec. 2000. vol. 267, No. 24, pp. 7246-7257.

Nagy et al., "Fully human, HLA-DR specific monoclonal antibodies efficiently induce programmed death of malignant lymphoid cells", Nat Med. 2002;8:801-807.

Qu et al., "Humanization of Immu31, an alpha-fetoprotein-specific antibody", Clin Cancer Res. Oct. 1999;5(10 Suppl):3095s-3100s.

Rudikoff et al., "Single amino acid substitution altering antigen-binding specificity", Proc Natl Acad Sci U S A. Mar. 1982;79(6):1979-83.

Schuurman et al., "The inter-heavy chain disulfide bonds of IgG4 are in equilibrium with intra-chain disulfide bonds", Mol Immunol. Jan. 2001;38(1):1-8.

Stein et al., "Characterization of a humanized IgG4 anti-HLA-DR monoclonal antibody that lacks effector cell functions but retains direct antilymphoma activity and increases the potency of rituximab", Blood 2006;108:2736-44.

Stein et al., "HLA-DR as a target for therapy of human and canine B-cell malignancies", Proc. Amer. Assoc. Cancer Res. 2009, 50:301, Abstr #1255.

Ting et al., "A new monoclonal antibody recognizing a linear determinant on the HLA-DRalpha chain N-terminus", Hybridoma (Larchmt). Dec. 2009;28(6):423-9.

Vaswani et al., "Humanized antibodies as potential therapeutic drugs", Ann. Allergy Asthma Immunol. 1998; 81:105-119.

Vidovic et al., "Selective apoptosis of neoplastic cells by the HLA-DR-specific monoclonal antibody", Cancer Lett. Jun. 19, 1998;128(2):127-35.

* cited by examiner

L243Vk

```
GACATCCAGATGACTCAGTCTCCAGCCTCCCTATCTGTATCTGTGGGAGAAACTGTCACCATCACATGTCGAGCAAGTGAGAATATTTAC     90
 1                                                                                      30
 D  I  Q  M  T  Q  S  P  A  S  L  S  V  S  V  G  E  T  V  T  I  T  C  R  A  S  E  N  I  Y
                                                  10                            20              **CDR1**

AGTAATTTAGCATGGTATCGTCAGAAACAGGGAAAATCTCCTCAGCTCCTGGTCTTTGCTGCATCAAACTTAGCAGATGGTGTGCCATCA    180
                                                                                         60
 S  N  L  A  W  Y  R  Q  K  Q  G  K  S  P  Q  L  L  V  F  A  A  S  N  L  A  D  G  V  P  S
              30                            40                            50
                                                                         **CDR2**

AGGTTCAGTGGCAGTGGATCAGGCACAGGTATTCCCTCAAGATCAACAGCCTGCAGTCTGAAGATTTTGGGATTATTACTGTCAACAT    270
                                                                                         90
 R  F  S  G  S  G  S  G  T  Q  Y  S  L  K  I  N  S  L  Q  S  E  D  F  G  D  Y  Y  C  Q  H
                            60                            70                            80

TTTTGGACTACTCCGTGGGGCGTTCGGTGGAGGCACCAACCTGGAAATCAAACGT                                      321
                                                108
 F  W  T  T  P  W  A  F  G  G  G  T  N  L  E  I  K  R
                                    100
 **CDR3**
```

Figure 2:
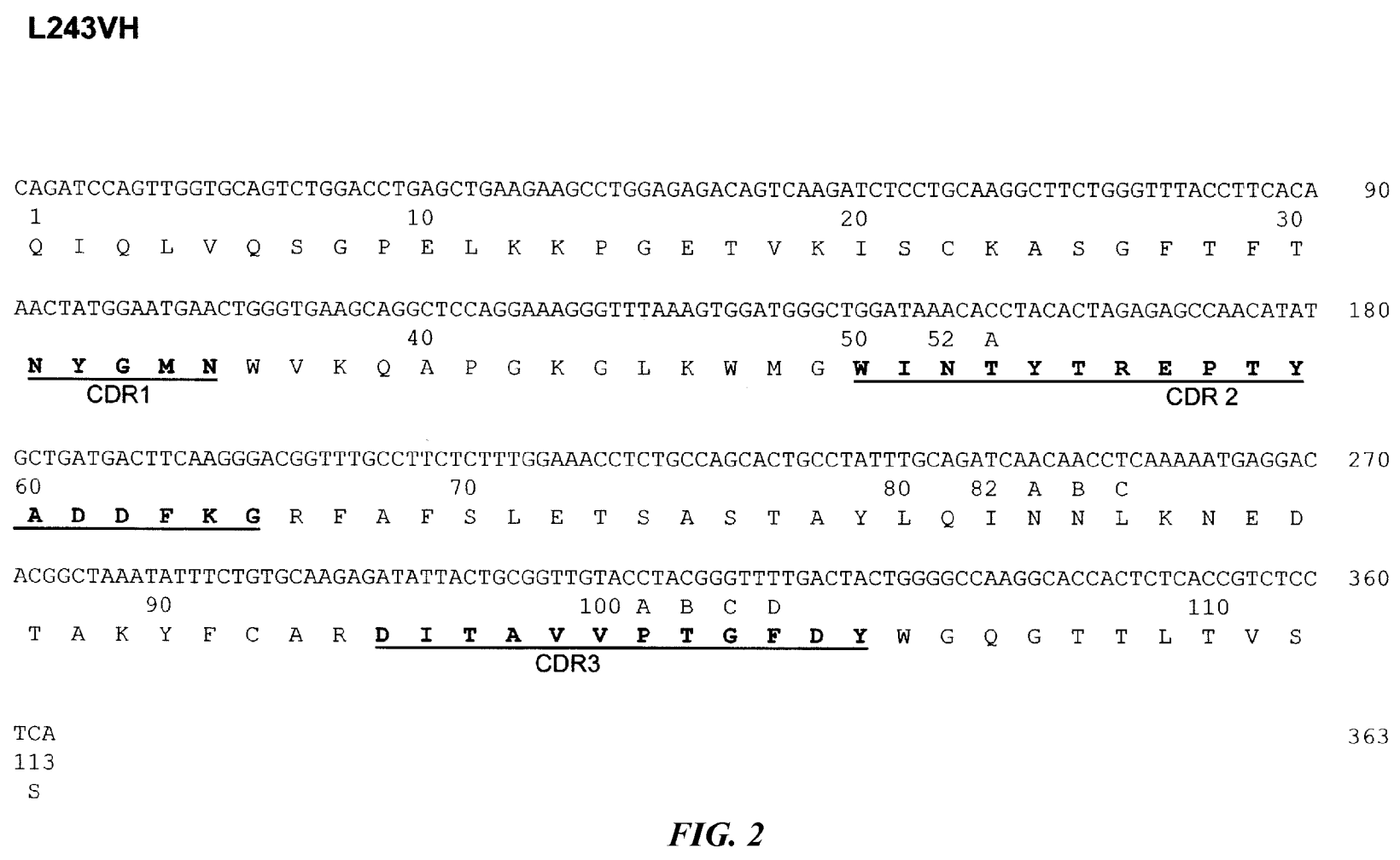

CAGATCCAGTTGGTGCAGTCTGGACCTGAGCTGAAGAAGCCTGGAGAGACAGTCAAGATCTCCTGCAAGGCTTCTGGGTTTACCTTCACA 90

1 10 20 30

Q I Q L V Q S G P E L K K P G E T V K I S C K A S G F T F T

AACTATGGAATGAACTGGGTGAAGCAGGCTCCAGGAAAGGGTTTAAAGTGGATGGGCTGGATAAACACCTACACTAGAGAGCCAACATAT 180

40 50 52 A

N Y G M N W V K Q A P G K G L K W M G W I N T Y T R E P T Y

CDR1 CDR 2

GCTGATGACTTCAAGGGACGGTTTGCCTTCTCTTTGGAAACCTCTGCCAGCACTGCCTATTTGCAGATCAACAACCTCAAAAATGAGGAC 270

60 70 80 82 A B C

A D D F K G R F A F S L E T S A S T A Y L Q I N N L K N E D

ACGGCTAAATATTTCTGTGCAAGAGATATTACTGCGGTTGTACCTACGGGTTTTGACTACTGGGGCCAAGGCACCACTCTCACCGTCTCC 360

90 100 A B C D 110

T A K Y F C A R D I T A V V P T G F D Y W G Q G T T L T V S

CDR3

TCA 363

```
GACATCCAGCTGACCCAGTCTCCATCATCTCTGAGCGCATCTGTTGGAGATAGGGTCACTATCACTTGTCGAGCAAGTGAGAATATTTAC    90
 1                                      10                                      20                                      30
 D  I  Q  L  T  Q  S  P  S  S  L  S  A  S  V  G  D  R  V  T  I  T  C  R  A  S  E  N  I  Y
                                                                          CDR1

AGTAATTTAGCATGGTATCGTCAGAAACCAGGGAAAGCACCTAAACTGCTGGTCTTTGCTGCATCAAACTTAGCAGATGGTGTGCCTTCG   180
                                        40                                      50                                      60
 S  N  L  A  W  Y  R  Q  K  P  G  K  A  P  K  L  L  V  F  A  A  S  N  L  A  D  G  V  P  S
                                                          CDR2

CGATTCTCTGGCAGCGGATCTGGGACAGATTATACTTTCACCATCAGCTCTCTTCAACCAGAAGACATTGCAACATATTATTGTCAACAT   270
                                        70                                      80                                      90
 R  F  S  G  S  G  S  G  T  D  Y  T  F  T  I  S  S  L  Q  P  E  D  I  A  T  Y  Y  C  Q  H

TTTTGGACTACTCCGTGGGCGTTCGGTGGAGGGACCAAGCTGCAGATCAAACGT                                         324
                                       100                                      108
 F  W  T  T  P  W  A  F  G  G  G  T  K  L  Q  I  R  K
   CDR3
```

CDR1: R A S E N I Y S N L A
CDR2: A A S N L A D
CDR3: Q H F W T T P W A

*FIG. 3* hL243VH

```
CAGGTGCAACTGCAGCAATCTGGGTCTGAGTTGAAGAAGCCTGGGGCCTCAGTGAAGGTTTCCTGCAAGGCTTCTGGATTTACCTTCACA   90
 1                                       10                                      20                                      30
 Q   V   Q   L   Q   Q   S   G   S   E   L   K   K   P   G   A   S   V   K   V   S   C   K   A   S   G   F   T   F   T

AACTATGGAATGAACTGGGTGAAGCAGGCCCCTGGACAAGGGCTTAAGTGGATGGGCTGGATAAACACCTACACTAGAGAGCCAACATAT  180
                                         40                                      50      52  A
 N   Y   G   M   N   W   V   K   Q   A   P   G   Q   G   L   K   W   M   G   W   I   N   T   Y   T   R   E   P   T   Y
     CDR1                                                                                                CDR 2

GCTGATGACTTCAAGGGACGGTTTGCCTTCTCCTTGGACACCTCTGTCAGCACGGCATATCTCCAGATCAGCAGCCTAAAGGCTGACGAC  270
60                                           70                                      80      82  A   B   C
 A   D   D   F   K   G   R   F   A   F   S   L   D   T   S   V   S   T   A   Y   L   Q   I   S   S   L   K   A   D   D

ACTGCCGTGTATTTCTGTGCAAGAGATATTACTGCGGTTGTACCTACGGGTTTTGACTACTGGGGCCAAGGGTCCCTGGTCACCGTCTCC  360
             90                                     100  A   B   C   D                                       110
 T   A   V   Y   F   C   A   R   D   I   T   A   V   V   P   T   G   F   D   Y   W   G   Q   G   S   L   V   T   V   S
                                             CDR3

TCA                                                                                                          363
113
 S
```

*FIG. 4*

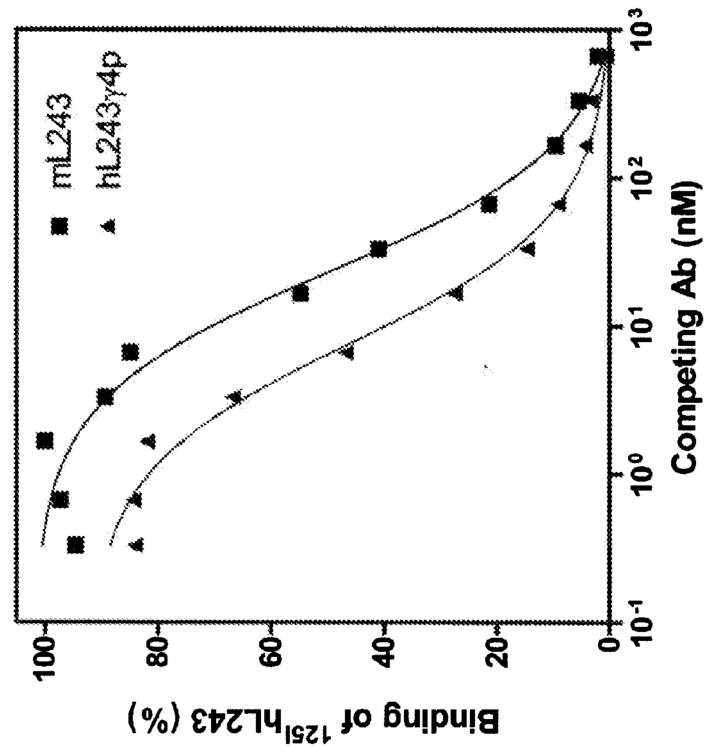
FIG. 6
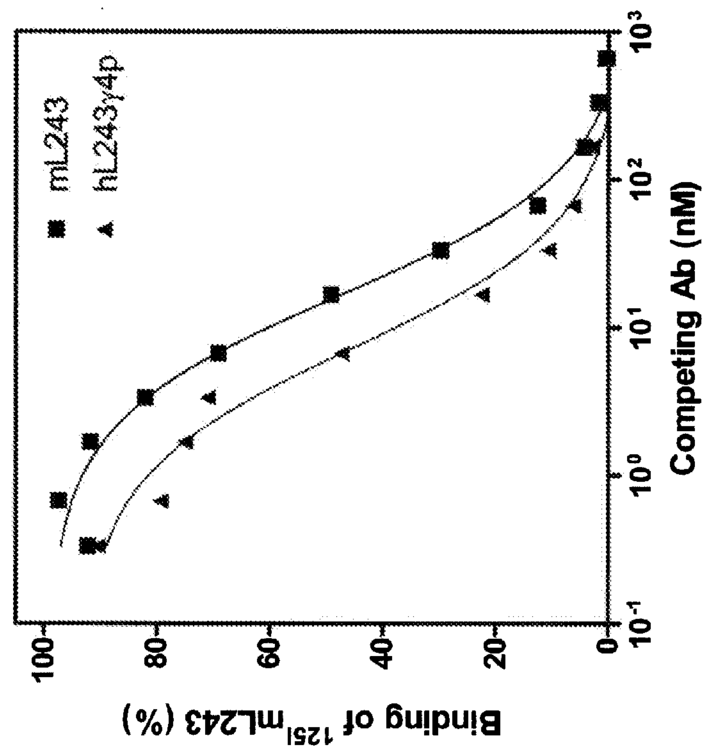

A

B

A
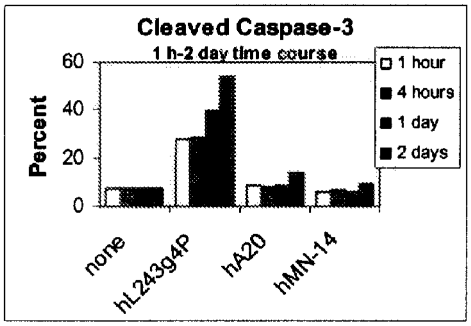
B
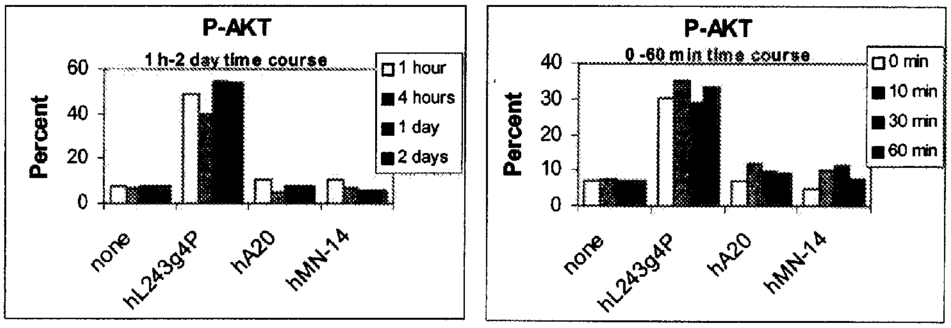
*FIG. 20*

MST: median survival time

| | a | b | c | d | e | f | g | h | i | j | k | l |
|---|---|---|---|---|---|---|---|---|---|---|---|---|
| hL243γ4P (10 nM) | - | - | - | - | + | + | + | + | + | + | + | + |
| NAC (5mM) | - | + | - | - | - | - | - | + | + | + | - | + |
| U0126 (10 μM) | - | - | - | + | - | - | + | - | - | + | + | + |
| SP600125 (10 μM) | - | - | + | - | - | + | - | - | + | - | + | + |

SEQUENCE LISTING

```
<160> NUMBER OF SEQ ID NOS: 44

<210> SEQ ID NO 1
<211> LENGTH: 44
<212> TYPE: PRT
<213> ORGANISM: Homo sapiens

<400> SEQUENCE: 1

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30
```

```
Val Glu Tyr Phe Thr Arg Leu Arg Glu Ala Arg Ala
        35                  40


<210> SEQ ID NO 2
<211> LENGTH: 45
<212> TYPE: PRT
<213> ORGANISM: Homo sapiens

<400> SEQUENCE: 2

Cys Gly His Ile Gln Ile Pro Pro Gly Leu Thr Glu Leu Leu Gln Gly
1               5                   10                  15

Tyr Thr Val Glu Val Leu Arg Gln Gln Pro Pro Asp Leu Val Glu Phe
            20                  25                  30

Ala Val Glu Tyr Phe Thr Arg Leu Arg Glu Ala Arg Ala
        35                  40                  45


<210> SEQ ID NO 3
<211> LENGTH: 17
<212> TYPE: PRT
<213> ORGANISM: Homo sapiens

<400> SEQUENCE: 3

Gln Ile Glu Tyr Leu Ala Lys Gln Ile Val Asp Asn Ala Ile Gln Gln
1               5                   10                  15

Ala


<210> SEQ ID NO 4
<211> LENGTH: 21
<212> TYPE: PRT
<213> ORGANISM: Homo sapiens

<400> SEQUENCE: 4

Cys Gly Gln Ile Glu Tyr Leu Ala Lys Gln Ile Val Asp Asn Ala Ile
1               5                   10                  15

Gln Gln Ala Gly Cys
            20


<210> SEQ ID NO 5
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(2)
<223> OTHER INFORMATION: Any conservative amino acid substitution
<220> FEATURE:
<221> NAME/KEY: MOD_RES
<222> LOCATION: (4)..(4)
<223> OTHER INFORMATION: Any conservative amino acid substitution
<220> FEATURE:
<221> NAME/KEY: MOD_RES
<222> LOCATION: (6)..(8)
<223> OTHER INFORMATION: Any conservative amino acid substitution
<220> FEATURE:
<221> NAME/KEY: MOD_RES
<222> LOCATION: (10)..(11)
<223> OTHER INFORMATION: Any conservative amino acid substitution
<220> FEATURE:
<221> NAME/KEY: MOD_RES
<222> LOCATION: (14)..(15)
<223> OTHER INFORMATION: Any conservative amino acid substitution
<220> FEATURE:
<221> NAME/KEY: MOD_RES
<222> LOCATION: (17)..(17)
```

<223> OTHER INFORMATION: Any conservative amino acid substitution
<220> FEATURE:
<221> NAME/KEY: MOD_RES
<222> LOCATION: (19)..(19)
<223> OTHER INFORMATION: Any conservative amino acid substitution
<220> FEATURE:
<221> NAME/KEY: MOD_RES
<222> LOCATION: (22)..(27)
<223> OTHER INFORMATION: Any conservative amino acid substitution
<220> FEATURE:
<221> NAME/KEY: MOD_RES
<222> LOCATION: (30)..(30)
<223> OTHER INFORMATION: Any conservative amino acid substitution
<220> FEATURE:
<221> NAME/KEY: MOD_RES
<222> LOCATION: (32)..(32)
<223> OTHER INFORMATION: Any conservative amino acid substitution
<220> FEATURE:
<221> NAME/KEY: MOD_RES
<222> LOCATION: (34)..(34)
<223> OTHER INFORMATION: Any conservative amino acid substitution
<220> FEATURE:
<221> NAME/KEY: MOD_RES
<222> LOCATION: (37)..(38)
<223> OTHER INFORMATION: Any conservative amino acid substitution
<220> FEATURE:
<221> NAME/KEY: MOD_RES
<222> LOCATION: (40)..(44)
<223> OTHER INFORMATION: Any conservative amino acid substitution

<400> SEQUENCE: 5

```
Xaa Xaa Ile Xaa Ile Xaa Xaa Xaa Leu Xaa Xaa Leu Leu Xaa Xaa Tyr
1               5                   10                  15

Xaa Val Xaa Val Leu Xaa Xaa Xaa Xaa Xaa Xaa Leu Val Xaa Phe Xaa
            20                  25                  30

Val Xaa Tyr Phe Xaa Xaa Leu Xaa Xaa Xaa Xaa Xaa
        35                  40
```

<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (1)..(5)
<223> OTHER INFORMATION: Any conservative amino acid substitution
<220> FEATURE:
<221> NAME/KEY: MOD_RES
<222> LOCATION: (7)..(8)
<223> OTHER INFORMATION: Any conservative amino acid substitution
<220> FEATURE:
<221> NAME/KEY: MOD_RES
<222> LOCATION: (11)..(12)
<223> OTHER INFORMATION: Any conservative amino acid substitution
<220> FEATURE:
<221> NAME/KEY: MOD_RES
<222> LOCATION: (15)..(17)
<223> OTHER INFORMATION: Any conservative amino acid substitution

<400> SEQUENCE: 6

```
Xaa Xaa Xaa Xaa Xaa Ala Xaa Xaa Ile Val Xaa Xaa Ala Ile Xaa Xaa
1               5                   10                  15

Xaa
```

<210> SEQ ID NO 7
<211> LENGTH: 17
<212> TYPE: PRT
<213> ORGANISM: Artificial Sequence
<220> FEATURE:

-continued

<223> OTHER INFORMATION: Description of Artificial Sequence: Synthetic
      peptide

<400> SEQUENCE: 7

Gln Ile Glu Tyr Val Ala Lys Gln Ile Val Asp Tyr Ala Ile His Gln
1               5                   10                  15

Ala

<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gln Ile Glu Tyr Lys Ala Lys Gln Ile Val Asp His Ala Ile His Gln
1               5                   10                  15

Ala

<210> SEQ ID NO 9
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gln Ile Glu Tyr His Ala Lys Gln Ile Val Asp His Ala Ile His Gln
1               5                   10                  15

Ala

<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gln Ile Glu Tyr Val Ala Lys Gln Ile Val Asp His Ala Ile His Gln
1               5                   10                  15

Ala

<210> SEQ ID NO 11
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Asp Leu Ile Glu Glu Ala Ala Ser Arg Ile Val Asp Ala Val Ile Glu
1               5                   10                  15

Gln Val Lys Ala Ala Gly Ala Tyr
            20

<210> SEQ ID NO 12
<211> LENGTH: 18
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 12

```
Leu Glu Gln Tyr Ala Asn Gln Leu Ala Asp Gln Ile Ile Lys Glu Ala
1               5                   10                  15

Thr Glu
```

<210> SEQ ID NO 13
<211> LENGTH: 20
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 13

```
Phe Glu Glu Leu Ala Trp Lys Ile Ala Lys Met Ile Trp Ser Asp Val
1               5                   10                  15

Phe Gln Gln Cys
            20
```

<210> SEQ ID NO 14
<211> LENGTH: 25
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 14

```
Pro Glu Asp Ala Glu Leu Val Arg Leu Ser Lys Arg Leu Val Glu Asn
1               5                   10                  15

Ala Val Leu Lys Ala Val Gln Gln Tyr
            20                  25
```

<210> SEQ ID NO 15
<211> LENGTH: 25
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 15

```
Pro Glu Asp Ala Glu Leu Val Arg Thr Ser Lys Arg Leu Val Glu Asn
1               5                   10                  15

Ala Val Leu Lys Ala Val Gln Gln Tyr
            20                  25
```

<210> SEQ ID NO 16
<211> LENGTH: 25
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 16

```
Pro Glu Asp Ala Glu Leu Val Arg Leu Ser Lys Arg Asp Val Glu Asn
1               5                   10                  15

Ala Val Leu Lys Ala Val Gln Gln Tyr
            20                  25
```

```
<210> SEQ ID NO 17
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any conservative amino acid substitution
<220> FEATURE:
<221> NAME/KEY: MOD_RES
<222> LOCATION: (4)..(4)
<223> OTHER INFORMATION: Any conservative amino acid substitution
<220> FEATURE:
<221> NAME/KEY: MOD_RES
<222> LOCATION: (7)..(7)
<223> OTHER INFORMATION: Any conservative amino acid substitution
<220> FEATURE:
<221> NAME/KEY: MOD_RES
<222> LOCATION: (10)..(10)
<223> OTHER INFORMATION: Any conservative amino acid substitution
<220> FEATURE:
<221> NAME/KEY: MOD_RES
<222> LOCATION: (18)..(18)
<223> OTHER INFORMATION: Any conservative amino acid substitution
<220> FEATURE:
<221> NAME/KEY: MOD_RES
<222> LOCATION: (23)..(23)
<223> OTHER INFORMATION: Any conservative amino acid substitution
<220> FEATURE:
<221> NAME/KEY: MOD_RES
<222> LOCATION: (26)..(26)
<223> OTHER INFORMATION: Any conservative amino acid substitution
<220> FEATURE:
<221> NAME/KEY: MOD_RES
<222> LOCATION: (33)..(34)
<223> OTHER INFORMATION: Any conservative amino acid substitution
<220> FEATURE:
<221> NAME/KEY: MOD_RES
<222> LOCATION: (37)..(38)
<223> OTHER INFORMATION: Any conservative amino acid substitution
<220> FEATURE:
<221> NAME/KEY: MOD_RES
<222> LOCATION: (40)..(40)
<223> OTHER INFORMATION: Any conservative amino acid substitution
<220> FEATURE:
<221> NAME/KEY: MOD_RES
<222> LOCATION: (42)..(42)
<223> OTHER INFORMATION: Any conservative amino acid substitution
<220> FEATURE:
<221> NAME/KEY: MOD_RES
<222> LOCATION: (44)..(44)
<223> OTHER INFORMATION: Any conservative amino acid substitution

<400> SEQUENCE: 17

Xaa His Ile Xaa Ile Pro Xaa Gly Leu Xaa Glu Leu Leu Gln Gly Tyr
1               5                   10                  15

Thr Xaa Glu Val Leu Arg Xaa Gln Pro Xaa Asp Leu Val Glu Phe Ala
            20                  25                  30

Xaa Xaa Tyr Phe Xaa Xaa Leu Xaa Glu Xaa Arg Xaa
        35                  40


<210> SEQ ID NO 18
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18
```

```
Gln Lys Ser Leu Ser Leu Ser Pro Gly Leu Gly Ser Gly Gly Gly Gly
1               5                   10                  15

Ser Gly Gly Cys Gly
            20


<210> SEQ ID NO 19
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gln Lys Ser Leu Ser Leu Ser Pro Gly Ala Gly Ser Gly Gly Gly Gly
1               5                   10                  15

Ser Gly Gly Cys Gly
            20


<210> SEQ ID NO 20
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gln Lys Ser Leu Ser Leu Ser Pro Gly Gly Ser Gly Gly Gly Gly Ser
1               5                   10                  15

Gly Gly Cys Gly
            20


<210> SEQ ID NO 21
<211> LENGTH: 175
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21

ggtctgagtt gaagaagcct ggggcctcag tgaaggtttc ctgcaaggct tctggattta      60

ccttcacaaa ctatggaatg aactgggtga agcaggcccc tggacaaggg cttaagtgga     120

tgggctggat aaacacctac actagagagc caacatatgc tgatgacttc aaggg          175


<210> SEQ ID NO 22
<211> LENGTH: 168
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22

acccttggcc ccagtagtca aaacccgtag gtacaaccgc agtaatatct cttgcacaga      60

aatacacggc agtgtcgtca gcctttaggc tgctgatctg gagatatgcc gtgctgacag     120

aggtgtccaa ggagaaggca aaccgtccct tgaagtcatc agcatatg                  168


<210> SEQ ID NO 23
<211> LENGTH: 38
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 23
gtggtgctgc agcaatctgg gtctgagttg aagaagcc 38

<210> SEQ ID NO 24
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tgaggagacg gtgaccaggg acccttggcc ccagtagt 38

<210> SEQ ID NO 25
<211> LENGTH: 155
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
tccatcatct ctgagcgcat ctgttggaga tagggtcact atcacttgtc gagcaagtga 60
gaatatttac agtaatttag catggtatcg tcagaaacca gggaaagcac ctaaactgct 120
ggtctttgct gcatcaaact tagcagatgg tgtgc 155

<210> SEQ ID NO 26
<211> LENGTH: 159
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
cagcttggtc cctccaccga acgcccacgg agtagtccaa aaatgttgac aataatatgt 60
tgcaatgtct tctggttgaa gagagctgat ggtgaaagta taatctgtcc cagatccgct 120
gccagagaat cgcgaaggca caccatctgc taagtttga 159

<210> SEQ ID NO 27
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gacattcagc tgacccagtc tccatcatct ctgagcgc 38

<210> SEQ ID NO 28
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28

```
ccggcagatc tgcagcttgg tccctccacc g                                31


<210> SEQ ID NO 29
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29

ccgcggtcac atggcaccac ctctcttgca gcttccacca agggccc               47


<210> SEQ ID NO 30
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30

ccggccgtcg cactcattta cccagagaca ggg                              33


<210> SEQ ID NO 31
<211> LENGTH: 324
<212> TYPE: DNA
<213> ORGANISM: Mus muscularis
<220> FEATURE:
<221> NAME/KEY: CDS
<222> LOCATION: (1)..(323)

<400> SEQUENCE: 31

gac atc cag atg act cag tct cca gcc tcc cta tct gta tct gtg gga       48
Asp Ile Gln Met Thr Gln Ser Pro Ala Ser Leu Ser Val Ser Val Gly
1               5                   10                  15

gaa act gtc acc atc aca tgt cga gca agt gag aat att tac agt aat       96
Glu Thr Val Thr Ile Thr Cys Arg Ala Ser Glu Asn Ile Tyr Ser Asn
            20                  25                  30

tta gca tgg tat cgt cag aaa cag gga aaa tct cct cag ctc ctg gtc      144
Leu Ala Trp Tyr Arg Gln Lys Gln Gly Lys Ser Pro Gln Leu Leu Val
        35                  40                  45

ttt gct gca tca aac tta gca gat ggt gtg cca tca agg ttc agt ggc      192
Phe Ala Ala Ser Asn Leu Ala Asp Gly Val Pro Ser Arg Phe Ser Gly
    50                  55                  60

agt gga tca ggc aca cag tat tcc ctc aag atc aac agc ctg cag tct      240
Ser Gly Ser Gly Thr Gln Tyr Ser Leu Lys Ile Asn Ser Leu Gln Ser
65                  70                  75                  80

gaa gat ttt ggg gat tat tac tgt caa cat ttt tgg act act ccg tgg      288
Glu Asp Phe Gly Asp Tyr Tyr Cys Gln His Phe Trp Thr Thr Pro Trp
                85                  90                  95

gcg ttc ggt gga ggc acc aac ctg gaa atc aaa cgt                      324
Ala Phe Gly Gly Gly Thr Asn Leu Glu Ile Lys Arg
            100                 105


<210> SEQ ID NO 32
<211> LENGTH: 108
<212> TYPE: PRT
<213> ORGANISM: Mus muscularis

<400> SEQUENCE: 32

Asp Ile Gln Met Thr Gln Ser Pro Ala Ser Leu Ser Val Ser Val Gly
1               5                   10                  15
```

```
Glu Thr Val Thr Ile Thr Cys Arg Ala Ser Glu Asn Ile Tyr Ser Asn
            20                  25                  30

Leu Ala Trp Tyr Arg Gln Lys Gln Gly Lys Ser Pro Gln Leu Leu Val
        35                  40                  45

Phe Ala Ala Ser Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Asp Tyr Tyr Cys Gln His Phe Trp Thr Thr Pro Trp
                85                  90                  95

Ala Phe Gly Gly Gly Thr Asn Leu Glu Ile Lys Arg
            100                 105


<210> SEQ ID NO 33
<211> LENGTH: 363
<212> TYPE: DNA
<213> ORGANISM: Mus muscularis
<220> FEATURE:
<221> NAME/KEY: CDS
<222> LOCATION: (1)..(363)

<400> SEQUENCE: 33

cag atc cag ttg gtg cag tct gga cct gag ctg aag aag cct gga gag       48
Gln Ile Gln Leu Val Gln Ser Gly Pro Glu Leu Lys Lys Pro Gly Glu
1               5                   10                  15

aca gtc aag atc tcc tgc aag gct tct ggg ttt acc ttc aca aac tat       96
Thr Val Lys Ile Ser Cys Lys Ala Ser Gly Phe Thr Phe Thr Asn Tyr
            20                  25                  30

gga atg aac tgg gtg aag cag gct cca gga aag ggt tta aag tgg atg      144
Gly Met Asn Trp Val Lys Gln Ala Pro Gly Lys Gly Leu Lys Trp Met
        35                  40                  45

ggc tgg ata aac acc tac act aga gag cca aca tat gct gat gac ttc      192
Gly Trp Ile Asn Thr Tyr Thr Arg Glu Pro Thr Tyr Ala Asp Asp Phe
    50                  55                  60

aag gga cgg ttt gcc ttc tct ttg gaa acc tct gcc agc act gcc tat      240
Lys Gly Arg Phe Ala Phe Ser Leu Glu Thr Ser Ala Ser Thr Ala Tyr
65                  70                  75                  80

ttg cag atc aac aac ctc aaa aat gag gac acg gct aaa tat ttc tgt      288
Leu Gln Ile Asn Asn Leu Lys Asn Glu Asp Thr Ala Lys Tyr Phe Cys
                85                  90                  95

gca aga gat att act gcg gtt gta cct acg ggt ttt gac tac tgg ggc      336
Ala Arg Asp Ile Thr Ala Val Val Pro Thr Gly Phe Asp Tyr Trp Gly
            100                 105                 110

caa ggc acc act ctc acc gtc tcc tca                                  363
Gln Gly Thr Thr Leu Thr Val Ser Ser
        115                 120


<210> SEQ ID NO 34
<211> LENGTH: 121
<212> TYPE: PRT
<213> ORGANISM: Mus muscularis

<400> SEQUENCE: 34

Gln Ile Gln Leu Val Gln Ser Gly Pro Glu Leu Lys Lys Pro Gly Glu
1               5                   10                  15

Thr Val Lys Ile Ser Cys Lys Ala Ser Gly Phe Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Arg Glu Pro Thr Tyr Ala Asp Asp Phe
```

```
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Lys Tyr Phe Cys
                85                  90                  95

Ala Arg Asp Ile Thr Ala Val Val Pro Thr Gly Phe Asp Tyr Trp Gly
            100                 105                 110

Gln Gly Thr Thr Leu Thr Val Ser Ser
        115                 120


<210> SEQ ID NO 35
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(324)

<400> SEQUENCE: 35

gac atc cag ctg acc cag tct cca tca tct ctg agc gca tct gtt gga       48
Asp Ile Gln Leu Thr Gln Ser Pro Ser Ser Leu Ser Ala Ser Val Gly
1               5                   10                  15

gat agg gtc act atc act tgt cga gca agt gag aat att tac agt aat       96
Asp Arg Val Thr Ile Thr Cys Arg Ala Ser Glu Asn Ile Tyr Ser Asn
            20                  25                  30

tta gca tgg tat cgt cag aaa cca ggg aaa gca cct aaa ctg ctg gtc      144
Leu Ala Trp Tyr Arg Gln Lys Pro Gly Lys Ala Pro Lys Leu Leu Val
        35                  40                  45

ttt gct gca tca aac tta gca gat ggt gtg cct tcg cga ttc tct ggc      192
Phe Ala Ala Ser Asn Leu Ala Asp Gly Val Pro Ser Arg Phe Ser Gly
    50                  55                  60

agc gga tct ggg aca gat tat act ttc acc atc agc tct ctt caa cca      240
Ser Gly Ser Gly Thr Asp Tyr Thr Phe Thr Ile Ser Ser Leu Gln Pro
65                  70                  75                  80

gaa gac att gca aca tat tat tgt caa cat ttt tgg act act ccg tgg      288
Glu Asp Ile Ala Thr Tyr Tyr Cys Gln His Phe Trp Thr Thr Pro Trp
                85                  90                  95

gcg ttc ggt gga ggg acc aag ctg cag atc aaa cgt                      324
Ala Phe Gly Gly Gly Thr Lys Leu Gln Ile Lys Arg
            100                 105


<210> SEQ ID NO 36
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Asp Ile Gln Leu Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Arg Gln Lys Pro Gly Lys Ala Pro Lys Leu Leu Val
        35                  40                  45

Phe Ala Ala Ser Asn Leu Ala Asp Gly Val Pro Ser Arg Phe Ser Gly
    50                  55                  60
```

```
Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln His Phe Trp Thr Thr Pro Trp
                85                  90                  95

Ala Phe Gly Gly Gly Thr Lys Leu Gln Ile Lys Arg
            100                 105


<210> SEQ ID NO 37
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(363)

<400> SEQUENCE: 37

cag gtg caa ctg cag caa tct ggg tct gag ttg aag aag cct ggg gcc       48
Gln Val Gln Leu Gln Gln Ser Gly Ser Glu Leu Lys Lys Pro Gly Ala
1               5                   10                  15

tca gtg aag gtt tcc tgc aag gct tct gga ttt acc ttc aca aac tat       96
Ser Val Lys Val Ser Cys Lys Ala Ser Gly Phe Thr Phe Thr Asn Tyr
            20                  25                  30

gga atg aac tgg gtg aag cag gcc cct gga caa ggg ctt aag tgg atg      144
Gly Met Asn Trp Val Lys Gln Ala Pro Gly Gln Gly Leu Lys Trp Met
        35                  40                  45

ggc tgg ata aac acc tac act aga gag cca aca tat gct gat gac ttc      192
Gly Trp Ile Asn Thr Tyr Thr Arg Glu Pro Thr Tyr Ala Asp Asp Phe
    50                  55                  60

aag gga cgg ttt gcc ttc tcc ttg gac acc tct gtc agc acg gca tat      240
Lys Gly Arg Phe Ala Phe Ser Leu Asp Thr Ser Val Ser Thr Ala Tyr
65                  70                  75                  80

ctc cag atc agc agc cta aag gct gac gac act gcc gtg tat ttc tgt      288
Leu Gln Ile Ser Ser Leu Lys Ala Asp Asp Thr Ala Val Tyr Phe Cys
                85                  90                  95

gca aga gat att act gcg gtt gta cct acg ggt ttt gac tac tgg ggc      336
Ala Arg Asp Ile Thr Ala Val Val Pro Thr Gly Phe Asp Tyr Trp Gly
            100                 105                 110

caa ggg tcc ctg gtc acc gtc tcc tca                                  363
Gln Gly Ser Leu Val Thr Val Ser Ser
        115                 120


<210> SEQ ID NO 38
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Gln Val Gln Leu Gln Gln Ser Gly Ser Glu Leu Lys Lys Pro Gly Ala
1               5                   10                  15

Ser Val Lys Val Ser Cys Lys Ala Ser Gly Phe Thr Phe Thr Asn Tyr
            20                  25                  30

Gly Met Asn Trp Val Lys Gln Ala Pro Gly Gln Gly Leu Lys Trp Met
        35                  40                  45

Gly Trp Ile Asn Thr Tyr Thr Arg Glu Pro Thr Tyr Ala Asp Asp Phe
    50                  55                  60

Lys Gly Arg Phe Ala Phe Ser Leu Asp Thr Ser Val Ser Thr Ala Tyr
```

-continued

```
65                  70                  75                  80

Leu Gln Ile Ser Ser Leu Lys Ala Asp Asp Thr Ala Val Tyr Phe Cys
                85                  90                  95

Ala Arg Asp Ile Thr Ala Val Val Pro Thr Gly Phe Asp Tyr Trp Gly
            100                 105                 110

Gln Gly Ser Leu Val Thr Val Ser Ser
        115                 120


<210> SEQ ID NO 39
<211> LENGTH: 5
<212> TYPE: PRT
<213> ORGANISM: Mus muscularis

<400> SEQUENCE: 39

Asn Tyr Gly Met Asn
1               5


<210> SEQ ID NO 40
<211> LENGTH: 17
<212> TYPE: PRT
<213> ORGANISM: Mus muscularis

<400> SEQUENCE: 40

Trp Ile Asn Thr Tyr Thr Arg Glu Pro Thr Tyr Ala Asp Asp Phe Lys
1               5                   10                  15

Gly


<210> SEQ ID NO 41
<211> LENGTH: 12
<212> TYPE: PRT
<213> ORGANISM: Mus muscularis

<400> SEQUENCE: 41

Asp Ile Thr Ala Val Val Pro Thr Gly Phe Asp Tyr
1               5                   10


<210> SEQ ID NO 42
<211> LENGTH: 11
<212> TYPE: PRT
<213> ORGANISM: Mus muscularis

<400> SEQUENCE: 42

Arg Ala Ser Glu Asn Ile Tyr Ser Asn Leu Ala
1               5                   10


<210> SEQ ID NO 43
<211> LENGTH: 7
<212> TYPE: PRT
<213> ORGANISM: Mus muscularis

<400> SEQUENCE: 43

Ala Ala Ser Asn Leu Ala Asp
1               5


<210> SEQ ID NO 44
<211> LENGTH: 9
<212> TYPE: PRT
<213> ORGANISM: Mus muscularis

<400> SEQUENCE: 44

Gln His Phe Trp Thr Thr Pro Trp Ala
1               5
```

HUMANIZED ANTI-HLA-DR ANTIBODIES

CROSS REFERENCE TO RELATED APPLICATIONS

This application is a divisional of U.S. patent application Ser. No. 12/754,140 (now issued U.S. Pat. No. 8,722,047, filed Apr. 5, 2010, which is a continuation-in-part of U.S. patent application Ser. No. 12/556,718 (now issued U.S. Pat. No. 8,613,903), filed Sep. 10, 2009, which is a divisional of U.S. patent application Ser. No. 11/368,296 (now issued U.S. Pat. No. 7,612,180), filed Mar. 3, 2006, which claims the benefit under 35 USC 119(e) of provisional U.S. patent application Ser. No. 60/657,695 filed on Mar. 3, 2005. U.S. patent application Ser. No. 12/754,140 (now issued U.S. Pat. No. 8,722,047) claims the benefit under 35 U.S.C. 119(e) of U.S. Provisional Patent Application Nos. 61/166,809, filed Apr. 6, 2009, and 61/168,715, filed Apr. 13, 2009. Each priority application is incorporated herein by reference in its entirety.

GOVERNMENT FUNDING

This work was supported in part by grant P01-CA103985 from the National Cancer Institute, National Institutes of Health. The federal government may have certain rights in the invention.

SEQUENCE LISTING

The instant application contains a Sequence Listing which has been submitted via EFS-Web and is hereby incorporated by reference in its entirety. Said ASCII copy, created on Apr. 1, 2010, is named IMM318US.txt and is 25,698 bytes in size.

FIELD

The present invention relates to compositions and methods of use of humanized antibodies directed to an epitope recognized by the murine monoclonal antibody L243. One exemplary embodiment relates to a humanized L243 (hL243) antibody that is specific for the human leucocyte antigen (HLA) encoded in the D region of the HLA gene cluster of the major histocompatibility complex (MHC), otherwise known as HLA-DR. Other embodiments relate to humanized antibodies that bind to the same epitope of HLA-DR as an antibody comprising the L243 CDR sequences or that block binding to HLA-DR of an antibody comprising the L243 CDR sequences. The subject antibodies inhibit proliferation of $HLA-DR^+$ cells and induce expression and release of TNF molecules. The subject antibodies are of use for treatment and/or diagnosis of various diseases, such as leukemias, lymphomas or other cancers or autoimmune disease, in dogs, humans and other subjects.

BACKGROUND

Rituximab anti-CD20 IgG therapy is credited with revitalizing antibody therapies with its ability to effectively treat follicular lymphoma without the extensive side effects associated with more traditional chemotherapy regimens. Since rituximab's approval by the FDA in 1997, the mortality rate from NHL has declined by 2.8% per year (Molina, 2008, Ann Rev Med 59:237-50), and the use of this agent has been expanded to a variety of diseases. While rituximab has been a remarkable success in follicular non-Hodgkin lymphoma (NHL), for which it was first approved, only half of the patients had an objective response, with at most 10% having a complete response (McLaughlin et al., 1998, J Clin Oncol 16:2825-33). Rituximab was less effective in the more aggressive types of NHL, such as diffuse large B cell lymphoma (DLBCL), but when it was combined with combination chemotherapy, improved and durable objective responses compared to the separate therapies were found, making R—CHOP a standard protocol for the treatment of DLBCL (e.g., Leonard et al., 2008, Semin Hematol 45:S11-16; Friedberg et al., 2002, Br J Haematol 117:828-34). The success of rituximab stimulated the evaluation of a number of other antibodies and antibody conjugates, and while a number of these have shown promising activity, to-date only one other unconjugated antibody therapy, alemtuzumab anti-CD52 for chronic lymphocytic leukemia (CLL), has been approved for use in hematologic malignancies (Robak, 2008, Curr Cancer Drug Targets 8:156-71).

Novel immunotherapeutic approaches, such as infusion of monoclonal antibodies (mAbs) to improve the management of lymphoma, are traditionally examined in murine models for efficacy and in Cynomolgus monkeys for safety and pharmacodynamics/pharmacokinetics, but could be more carefully evaluated prior to human studies to identify and better anticipate the impact of such interventions in humans if other tumor models were available. Spontaneously-arising neoplasms in companion animals have been proposed as a useful system for examining numerous hypotheses relevant to human cancer control, and have recently been acknowledged by the National Cancer Institute as valuable study models (Dewhirst et al., 2001, Spontaneous Pet Animal Cancers. In: B. A. Teicher (ed.), Tumor Models in Cancer Research., pp. 565-89. Totowa, N.J.: Humana Press; Hansen and Khanna, 2004, Eur J Can 40:858-80; Paloni and Khanna, 2008, Nature Reviews Cancer 8:147-56). Canine lymphoma is particularly valuable as a model system, because it is common (incidence 25-40/100,000), similar pathologically to human high-grade, B cell NHL, and is initially controllable with chemotherapy followed by subsequent resistance that limits long-term control (median remission and survival times are 6-9 months and 10-14 months, respectively) (Vail and Young, 2007, Canine lymphoma and lymphoid leukemia. In: S. J. Withrow and D. M. Vail (eds.), Small Animal Clinical Oncology., 4 edition, pp. 699-733. St. Louis (MO): Saunders). Recent investigations have confirmed that canine lymphoma is genetically similar to the human disease (Modiano et al., 2005, Cancer Res 65:5654-61; Breen and Modiano, 2008, Croimosome Res 16:145-54), further justifying the model for evaluating novel, targeted therapeutic strategies for the benefit of both species.

The human leukocyte antigen-DR (HLA-DR) is one of three isotypes of the major histocompatibilty complex (MHC) class II antigens. HLA-DR is highly expressed on a variety of hematologic malignancies and has been actively pursued for antibody-based lymphoma therapy (Brown et al., 2001, Clin Lymphoma 2:188-90; DeNardo et al., 2005, Clin Cancer Res 11:7075s-9s; Stein et al., 2006, Blood 108:2736-44). Preliminary studies indicate that anti-HLA-DR mAbs are markedly more potent than other naked mAbs of current clinical interest in in vitro and in vivo experiments in lymphomas, leukemias, and multiple myeloma (Stein et al., unpublished results). HLA-DR is also expressed on a subset of normal immune cells, including B cells, monocytes/macrophages, Langerhans cells, dendritic cells, and activated T cells (Dechant et al., 2003, Semin Oncol 30:465-75). Thus, it is perhaps not surprising that infusional toxicities, likely related to complement activation, have been problematic clinically with the administration of anti-HLA-DR antibody (Shi et al., 2002, Leuk Lymphoma 43:1303-12.

The L243 antibody (hereafter mL243) is a murine IgG2an anti-HLA-DR antibody. This antibody may be of potential use in the treatment of diseases such as autoimmune disease or cancer, particularly leukemias or lymphomas, by targeting the D region of HLA. mL243 demonstrates potent suppression of in vitro immune function and is monomorphic for all HLA-DR proteins. However, problems exist with the administration of mouse antibodies to human patients, such as the induction of a human anti-mouse antibody (HAMA) response. A need exists for antibodies with the antigenic specificity of mL243, that may be administered to human subjects.

SUMMARY

One embodiment of the present invention provides for a recombinant humanized anti-HLA-DR antibody molecule having specificity for the epitope recognized by the murine monoclonal antibody mL243. This epitope can be an antigenic determinant dependent on the DR-α chain. In particular embodiments, the antibody may be a humanized CDR-grafted antibody, such as an hL243 antibody comprising the murine L243 heavy chain CDR sequences CDR1 (NYGMN (SEQ ID NO: 39)), CDR2 (WINTYTREPTYADDFKG (SEQ ID NO: 40)) and CDR3 (DITAVVPTGFDY (SEQ ID NO: 41)) and the light chain CDR sequences CDR1 (RASENIYSNLA (SEQ ID NO: 42)), CDR2 (AASNLAD (SEQ ID NO: 43)), and CDR3 (QHFWTTPWA (SEQ ID NO: 44)), attached to human antibody framework (FR) and constant region sequences. In preferred embodiments, a humanized L243 antibody may further comprise one or more of framework residues 27, 38, 46, 68 and 91 substituted from the mL243 heavy chain and/or one or more of framework residues 37, 39, 48 and 49 substituted from the mL243 light chain. In a more preferred embodiment, the hL243 antibody comprises the sequences of SEQ ID NO:6 and SEQ ID NO:8.

In alternative embodiments the humanized anti-HLA-DR antibody may be an antibody that competes for binding to the HLA-DR antigen with an antibody comprising the L243 heavy chain CDR sequences CDR1 (NYGMN (SEQ ID NO: 39)), CDR2 (WINTYTREPTYADDFKG (SEQ ID NO: 40)) and CDR3 (DITAVVPTGFDY (SEQ ID NO: 41)) and the light chain CDR sequences CDR1 (RASENIYSNLA (SEQ ID NO: 42)), CDR2 (AASNLAD (SEQ ID NO: 43)), and CDR3 (QHFWTTPWA (SEQ ID NO: 44)). The L243 antibody used in competition experiments may be an mL243 antibody, which may be obtained at the American Type Culture Collection, 10801 University Blvd., Manassas, Va. 20110-2209 (see Accession number ATCC HB55). Antibody competition experiments are well known in the art, as disclosed in the Examples below.

In another embodiment, the humanized anti-HLA-DR antibody may be an immunoconjugate that is attached to at least one therapeutic and/or diagnostic agent. Conjugates with multiple therapeutic agents of the same or different type are also encompassed. Alternatively, the humanized anti-HLA-DR antibody may be administered in combination with at least one therapeutic agent administered before, simultaneously with or after the humanized anti-HLA-DR antibody. Any therapeutic agent known in the art, as discussed in more detail below, may be utilized in combination with or attached to the humanized anti-HLA-DR antibody, including but not limited to radionuclides, immunomodulators, anti-angiogenic agents, cytokines, chemokines, growth factors, hormones, drugs, prodrugs, enzymes, oligonucleotides, siRNAs, pro-apoptotic agents, photoactive therapeutic agents, cytotoxic agents, chemotherapeutic agents, toxins, other antibodies or antigen binding fragments thereof.

In certain methods of use, the subject antibody may bind to at least one epitope of HLA-DR on HLA-DR$^+$ cells, resulting in cell death. Either naked anti-HLA-DR antibodies or immunoconjugates may be used. In one particular embodiment, cell death may result without use of either cytotoxic addends or immunological effector mechanisms, for example by induction of apoptosis. The anti-HLA-DR antibodies may be of use for therapy of any disease state in which HLA-DR$^+$ cells are involved, including but not limited to various forms of cancer or autoimmune disease.

In certain embodiments, the subject antibodies may be used in a pharmaceutical composition for therapeutic and/or diagnostic use. A pharmaceutical composition may contain further therapeutic agents as described below, in addition to other standard components such as buffers, detergents, salts, excipients, preservatives and other such agents known in the art.

Other embodiments may concern nucleic acid molecules that encode one or more of the disclosed antibodies, conjugates or fusion proteins described herein. The nucleic acids may be contained in one or more expression vectors, which may be transfected into appropriate host cells for expression of the subject antibodies, conjugates or fusion proteins.

The pharmaceutical composition, fusion protein or multispecific antibody may further comprise one or more additional antibodies or fragments thereof which bind to an antigen selected from the group consisting of carbonic anhydrase IX, CCCL19, CCCL21, CSAp, CD1, CD1a, CD2, CD3, CD4, CD5, CD8, CD11A, CD14, CD15, CD16, CD18, CD19, IGF-1R, CD20, CD21, CD22, CD23, CD25, CD29, CD30, CD32b, CD33, CD37, CD38, CD40, CD40L, CD45, CD46, CD52, CD54, CD55, CD59, CD64, CD66a-e, CD67, CD70, CD74, CD79a, CD80, CD83, CD95, CD126, CD133, CD138, CD147, CD154, AFP, PSMA, CEACAM5, CEACAM-6, B7, ED-B of fibronectin, Factor H, FHL-1, Flt-3, folate receptor, GROB, HMGB-1, hypoxia inducible factor (HIF), HM1.24, insulin-like growth factor-1 (ILGF-1), IFN-γ, IFN-α, IFN-β, IL-2, IL-4R, IL-6R, IL-13R, IL-15R, IL-17R, IL-18R, IL-6, IL-8, IL-12, IL-15, IL-17, IL-18, IL-25, IP-10, MAGE, mCRP, MCP-1, MIP-1A, MIP-1B, MIF, MUC1, MUC2, MUC3, MUC4, MUC5, PAM4 antigen, NCA-95, NCA-90, Ia, HM1.24, EGP-1, EGP-2, HLA-DR, tenascin, Le(y), RANTES, T101, TAC, Tn antigen, Thomson-Friedenreich antigens, tumor necrosis antigens, TNF-α, TRAIL receptor (R1 and R2), VEGFR, EGFR, P1GF, complement factors C3, C3a, C3b, C5a, C5, and an oncogene product. The additional antibody or fragment thereof may be administered before, with, or after any pharmaceutical composition containing a humanized anti-CD74 antibody.

Exemplary additional antibodies that may be utilized include, but are not limited to, hR1 (anti-IGF-1R, U.S. patent application Ser. No. 12/722,645, filed Mar. 12, 2010) hPAM4 (anti-mucin, U.S. Pat. No. 7,282,567), hA20 (anti-CD20, U.S. Pat. No. 7,251,164), hA19 (anti-CD19, U.S. Pat. No. 7,109,304), hIMMU31 (anti-AFP, U.S. Pat. No. 7,300,655), hLL1 (anti-CD74, U.S. Pat. No. 7,312,318), hLL2 (anti-CD22, U.S. Pat. No. 7,074,403), hMu-9 (anti-CSAp, U.S. Pat. No. 7,387,773), hL243 (anti-HLA-DR, U.S. Pat. No. 7,612,180), hMN-14 (anti-CEA, U.S. Pat. No. 6,676,924), hMN-15 (anti-CEA, U.S. Pat. No. 7,541,440), hRS7 (anti-EGP-1, U.S. Pat. No. 7,238,785) and hMN-3 (anti-CEA, U.S. Pat. No. 7,541,440) the Examples section of each cited patent or application incorporated herein by reference. The skilled artisan will realize that this list is not limiting and that any known antibody may be used, as discussed in more detail below.

Various embodiments may concern use of the subject anti-HLA-DR antibodies or fragments thereof to treat or diagnose a disease, including but not limited to B cell non-Hodgkin's lymphomas, B cell acute and chronic lymphoid leukemias, Burkitt lymphoma, Hodgkin's lymphoma, hairy cell leukemia, acute and chronic myeloid leukemias, T cell lymphomas and leukemias, multiple myeloma, Waldenstrom's macroglobulinemia, carcinomas, melanomas, sarcomas, gliomas, and skin cancers. The carcinomas may be selected from the group consisting of carcinomas of the oral cavity, gastrointestinal tract, pulmonary tract, breast, ovary, prostate, uterus, urinary bladder, pancreas, liver, gall bladder, skin, and testes. In addition, the subject anti-HLA-DR antibodies or fragments may be used to treat an autoimmune disease, for example acute idiopathic thrombocytopenic purpura, chronic idiopathic thrombocytopenic purpura, dermatomyositis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcal nephritis, erythema nodosum, Takayasu's arteritis, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitis obliterans, Sjogren's syndrome, primary biliary cirrhosis, Hashimoto's thyroiditis, thyrotoxicosis, scleroderma, chronic active hepatitis, polymyositis/dermatomyositis, polychondritis, pemphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis, psoriasis, or fibrosing alveolitis. In certain embodiments, the subject antibodies may be used to treat leukemia, such as chronic lymphocytic leukemia, acute lymphocytic leukemia, chronic myeloid leukemia or acute myeloid leukemia.

In one embodiment, a pharmaceutical composition of the present invention may be use to treat a subject having a metabolic disease, such amyloidosis, or a neurodegenerative disease, such as Alzheimer's disease. In addition, a pharmaceutical composition of the present invention may be use to treat a subject having an immune-dysregulatory disorder.

BRIEF DESCRIPTION OF THE DRAWINGS

The following drawings form part of the present specification and are included to further demonstrate certain embodiments of the present invention. The embodiments may be better understood by reference to one or more of these drawings in combination with the detailed description of specific embodiments presented herein.

FIG. 1 (also SEQ ID NO:31 and SEQ ID NO:32) illustrates an exemplary DNA encoding an amino acid sequence $V_K$ of the mouse L243 anti-HLA-DR antibody. The putative CDR regions are underlined. Nucleotide residues are numbered sequentially. Kabat's Ig molecule numbering is used for amino acid residues. The numbering for the residues with a letter (on top) is the number of preceding residues plus the letter, eg, the number for T following N52 is 52A; the numbers for N, N and L following 82 are 82A, 82B and 82C, respectively.

FIG. 2 (also SEQ ID NO:33 and SEQ ID NO:34) illustrates an exemplary DNA encoding an amino acid sequence $V_H$ of the mouse L243 anti-HLA-DR antibody. The putative CDR regions are underlined. Nucleotide residues are numbered sequentially. Kabat's Ig molecule numbering is used for amino acid residues as described above.

FIG. 3 (also SEQ ID NO:35 and SEQ ID NO:36) illustrates exemplary DNA and amino acid sequences of a humanized L243 $V_K$. The bold and underlined sections of the amino acid sequences indicate the CDRs as defined by the Kabat numbering scheme.

FIG. 4 (also SEQ ID NO:37 and SEQ ID NO:38) illustrates exemplary DNA and amino acid sequences of a humanized L243 $V_H$. The bold and underlined sections of the amino acid sequences indicate the CDRs as defined by the Kabat numbering scheme.

FIG. 6 illustrates exemplary Ag-binding affinities comparing hL243 γ 4P and mL243 in a competitive cell surface binding assay. A constant amount (100,000 cpm, ~10 μCi/μg) of $^{125}$I-labeled mL234 (A) or hL243γ4P (B) was mixed with varying concentrations (0.2-700 nM) of unlabeled hL243γ4P (solid triangle) or mL2343 (solid box). The mixtures were added to Raji cells and incubated at room temperature for 2 h. The cells were washed to remove unbound antibodies and the radioactivity associated with the cells was counted. hL243γ4P and mL234 were shown to compete with each other for binding to cell surface Ag. In both cases hL243γ4P appeared to bind to Raji cells more strongly than mL243.

FIG. 20 illustrates cleaved caspase-3 (A) and P-AKT (B) time course studies in Daudi cells.

DETAILED DESCRIPTION

Definitions

Figure 5:
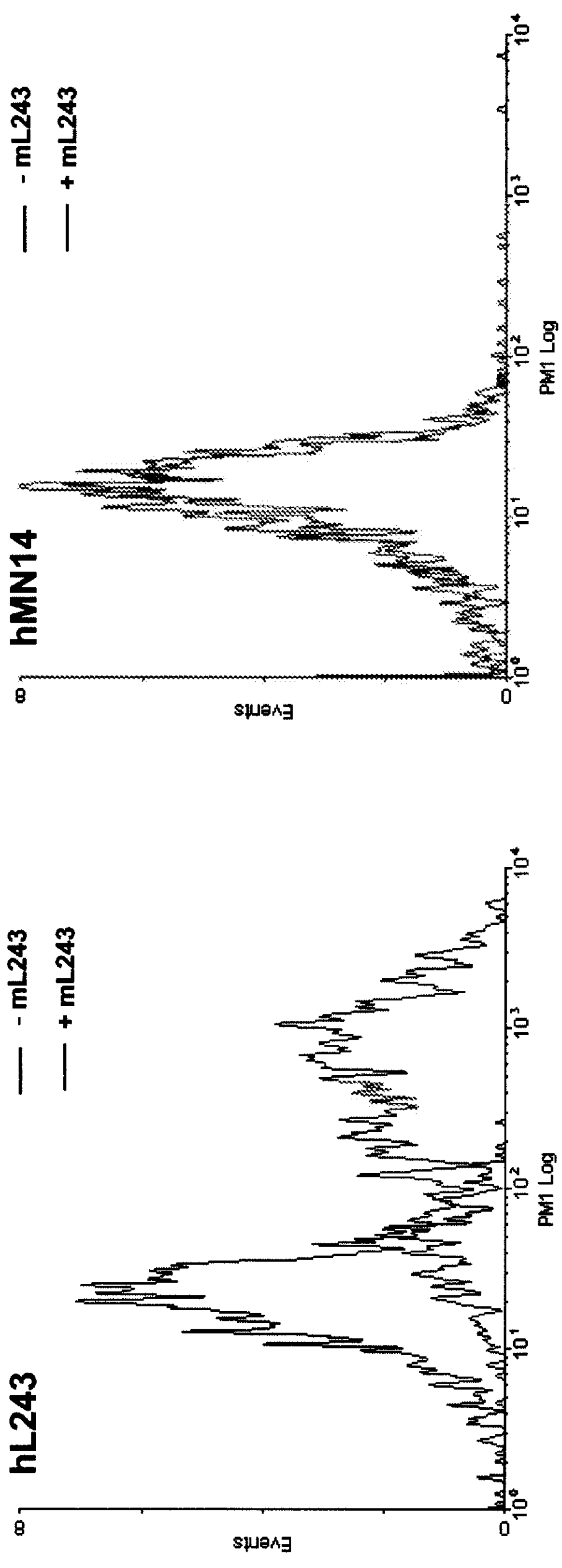
FIG. 5 illustrates an exemplary antigen-binding specificity of hL243. Raji cells, preincubated with a saturating concentration of mL234 (for blocking cell surface antigen ("Ag") sites) or without, were resuspended in PBS containing 1% BSA and 10 μg/ml of purified hL243 and incubated for 1 h at 4° C. After washing, the cells were resuspended in PBS containing 1% BSA and PE-labeled goat anti-human IgG, Fc fragment specific antibody. After further incubation at 4° C. for 30 min, the cells were counted in a Guava PCA. (A) shows specific binding of hL243 to Raji human lymphoma cells, which was blocked by preincubation of the cells with mL243. (B) is a negative binding control, performed with anti-CEA antibody (hMN-14) in place of hL243 under identical conditions.

Unless otherwise specified, "a" or "an" means "one or more".

As used herein, "subject" or "subjects" may include, but are not limited to, mammals such as humans, dogs, cats, rabbits, pigs, goats, sheep, horses, alpacas, llamas or cattle.

"Antibody-dependent cell mediated cytotoxicity" or "ADCC" is a cell-mediated reaction in which nonspecific cytotoxic cells that express Fc receptors (natural killer cells, neutrophils, and macrophages) recognize bound antibody on target cells and subsequently cause lysis of the target cells. The primary cells for mediating ADCC are the natural killer cells (express the FcDRIII only) and monocytes (express FcDRI, FcDRII and FcDRIII).

"Complement-dependent cytotoxicity" or "CDC" refers to the lysing of a target in the presence of complement. The complement activation pathway is initiated by the binding of the first component of the complement system (C1q) to a molecule (eg, an antibody) complexed with a cognate antigen.

The "Fc receptor" or "FcR" is used to describe a receptor that binds to the Fc region of an antibody. Both CDC and ADCC require the Fc portion of a MAb and the effect of ADCC can be augmented by increasing the binding affinity for FcγR (IgG Fc receptors) on effector cells (Shinkawa, et al, *J Biol Chem* 278: 3466-3473, 23; Shields et al, *J Biol Chem* 211: 26733-2674, 22; Shields et al, *J Biol Chem* 276: 6591-664, 22; Davies et al, *Biotechnol Bioeng* 74: 288-294,21; and Umana et al, *Nature Biotechnol* 176-18, 1999).

An "antibody" as used herein refers to a full-length (ie, naturally occurring or formed by normal immunoglobulin gene fragment recombinatorial processes) immunoglobulin molecule (eg, an IgG antibody) or an immunologically active (ie, specifically binding) portion of an immunoglobulin molecule, like an antibody fragment. An "antibody" includes monoclonal, polyclonal, bispecific, multispecific, murine, chimeric, humanized and human antibodies.

A "naked antibody" is an antibody or antigen binding fragment thereof that is not attached to a therapeutic or diagnostic agent. The Fc portion of an intact naked antibody can provide effector functions, such as complement fixation and ADCC (see, e.g., Markrides, *Pharmacol Rev* 50:59-87, 1998). Other mechanisms by which naked antibodies induce cell death may include apoptosis. (Vaswani and Hamilton, *Ann Allergy Asthma Immunol* 81: 105-119, 1998.)

An "antibody fragment" is a portion of an intact antibody such as $F(ab')_2$, $F(ab)_2$, Fab', Fab, Fv, sFv, scFv and the like. Regardless of structure, an antibody fragment binds with the same antigen that is recognized by the full-length antibody.

For example, antibody fragments include isolated fragments consisting of the variable regions, such as the "Fv" fragments consisting of the variable regions of the heavy and light chains or recombinant single chain polypeptide molecules in which light and heavy variable regions are connected by a peptide linker ("scFv proteins"). "Single-chain antibodies", often abbreviated as "scFv" consist of a polypeptide chain that comprises both a $V_H$ and a $V_L$ domain which interact to form an antigen-binding site. The $V_H$ and $V_L$ domains are usually linked by a peptide of 1 to 25 amino acid residues. Antibody fragments also include diabodies, triabodies and single domain antibodies (dAb).

Humanized L243 Antibodies

In preferred embodiments, the subject anti-HLA-DR antibody may be a humanized L243 antibody. Such antibodies bind to the same epitope on HLA-DR as the parental murine L243 antibody, but have reduced immunogenicity. mL243 is a monoclonal antibody previously described by Lampson & Levy (J Immunol, 1980, 125:293). The amino acid sequences of the light and heavy chain variable regions of the mL243 antibody are shown in FIG. 1 and FIG. 2. mL243 has been deposited at the American Type Culture Collection, 10801 University Blvd., Manassas, Va. 20110-2209, under Accession number ATCC HB55.

The humanized L243 antibodies may comprise the L243 heavy chain CDR sequences CDR1 (NYGMN (SEQ ID NO: 39)), CDR2 (WINTYTREPTYADDFKG (SEQ ID NO: 40)) and CDR3 (DITAVVPTGFDY (SEQ ID NO: 41)) and the light chain CDR sequences CDR1 (RASENIYSNLA (SEQ ID NO: 42)), CDR2 (AASNLAD (SEQ ID NO: 43)), and CDR3 (QHFWTTPWA (SEQ ID NO: 44)), attached to human antibody FR and constant region sequences. In more preferred embodiments, one or more murine FR amino acid residues are substituted for the corresponding human FR residues, particularly at locations adjacent to or nearby the CDR residues. Exemplary murine $V_H$ residues that may be substituted in the humanized design are at positions: F27, K38, K46, A68 and F91. Exemplary murine $V_L$ residues that may be substituted in the humanized design are at positions R37, K39, V48, F49, and G1. Further details for humanizing antibody sequences, while retaining the antigenic specificity of the original non-human antibody, are disclosed in the Examples below.

A particularly preferred form of hL243 antibody is illustrated in FIG. 3 and FIG. 4, incorporating FR sequences from the human RF-TS3, NEWM and REI antibodies. However, in other embodiments, the FR residues may be derived from any suitable human immunoglobulin, provided that the humanized antibody can fold such that it retains the ability to specifically bind HLA-DR. Preferably the type of human framework (FR) used is of the same/similar class/type as the donor antibody. More preferably, the human FR sequences are selected to have a high degree of sequence homology with the corresponding murine FR sequences, particularly at positions spatially close or adjacent to the CDRs. In accordance with this embodiment, the frameworks (ie, FR1-4) of the humanized L243 $V_H$ or $V_L$ may be derived from a combination of human antibodies. Examples of human frameworks which may be used to construct CDR-grafted humanized antibodies are LAY, POM, TUR, TEI, KOL, NEWM, REI, RF and EU. Preferably human RF-TS3 FR1-3 and NEWM FR4 are used for the heavy chain and REI FR1-4 are used for the light chain. The variable domain residue numbering system used herein is described in Kabat et al, (1991), Sequences of Proteins of Immunological Interest, 5th Edition, United States Department of Health and Human Services The light and heavy chain variable domains of the humanized antibody molecule may be fused to human light or heavy chain constant domains. The human constant domains may be selected with regard to the proposed function of the antibody. In one embodiment, the human constant domains may be selected based on a lack of effector functions. The heavy chain constant domains fused to the heavy chain variable region may be those of human IgA (α1 or α2 chain), IgG (γ1, γ2, γ3 or γ4 chain) or IgM (μ chain). The light chain constant domains which may be fused to the light chain variable region include human lambda and kappa chains.

In one particular embodiment of the present invention, a γ1 Chain is used. In yet another particular embodiment, a γ4 chain is used. The use of the γ4 chain may in some cases increase the tolerance to hL243 in subjects (decreased side effects and infusion reactions, etc).

In one embodiment, analogues of human constant domains may be used. These include but are not limited to those constant domains containing one or more additional amino acids than the corresponding human domain or those constant domains wherein one or more existing amino acids of the corresponding human domain have been deleted or altered. Such domains may be obtained, for example, by oligonucleotide directed mutagenesis.

As used herein, the term "altered" when used in conjunction with the ability of an antibody to fix complement indicates a decrease in the ability of antibody to fix complement compared to the starting unaltered antibody. As used herein the phrase "substantially" reduce complement fixation denotes that human complement fixation is preferably less than or equal to 30%, more preferably less than or equal to 20%, and is most preferably less than or equal to 10% of the level seen with wild type antibody. Altered complement fixing ability may be produced by techniques that are well known in the art, for example, deleting residues, inserting a glycosylation site at a suitable position in the molecule, or exchanging lower hinge regions of antibodies of different isotypes.

In a particular embodiment, an anti-HLA-DR antibody or fragment thereof may be a fusion protein. The fusion protein may contain one or more humanized L243 antibodies or fragments thereof. In various embodiments, the fusion protein may also comprise one or more additional antibodies, against HLA-DR or a different antigen, or may comprise a different effector protein or peptide, such as a cytokine. For example, the different antigen may be a tumor marker selected from a B cell lineage antigen, (eg, CD19, CD20, or CD22) for the treatment of B cell malignancies. In another example, the different antigen may be expressed on other cells that cause other types of malignancies. Further, the cell marker may be a non-B cell lineage antigen, such as selected from the group consisting of HLA-DR, CD3, CD33, CD52, CD66, MUC1 and TAC.

In one embodiment, an hL243 antibody may be combined with other antibodies and used to treat a subject having or suspected of developing a disease. In accordance with this embodiment, an hL243 antibody or fragment thereof may be combined with an anticancer monoclonal antibody such as a humanized monoclonal antibody (eg hA20, anti-CD20 Mab) and used to treat cancer. It is contemplated herein that an hL243 antibody may be used as a separate antibody composition in combination with one or more other separate antibody compositions, or used as a bi-functional antibody containing, for example, one hL243 and one other anti-tumor antibody, such as hA20. In another particular embodiment, the antibody may target a B cell malignancy. The B cell malignancy may consist of indolent forms of B cell lymphomas, aggressive forms of B cell lymphomas, chronic lymphatic leukemias, acute lymphatic leukemias, Waldenstrom's macroglobulinemia, and multiple myeloma. Other non-malignant B cell disorders and related diseases that may be treated with the subject antibodies include many autoimmune and immune dysregulatory diseases, such as septicemia and septic shock.

Antibodies and Antibody Fragments

Techniques for preparing monoclonal antibodies against virtually any target antigen are well known in the art. See, for example, Kohler and Milstein, *Nature* 256: 495 (1975), and Coligan et al. (eds.), CURRENT PROTOCOLS IN IMMUNOLOGY, VOL. 1, pages 2.5.1-2.6.7 (John Wiley & Sons 1991). Briefly, monoclonal antibodies can be obtained by injecting mice with a composition comprising an antigen, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

MAbs can be isolated and purified from hybridoma cultures by a variety of well-established techniques. Such isolation techniques include affinity chromatography with Protein-A Sepharose, size-exclusion chromatography, and ion-exchange chromatography. See, for example, Coligan at pages 2.7.1-2.7.12 and pages 2.9.1-2.9.3. Also, see Baines et al., "Purification of Immunoglobulin G (IgG)," in METHODS iN MOLECULAR BIOLOGY, VOL. 10, pages 79-104 (The Humana Press, Inc. 1992).

After the initial raising of antibodies to the immunogen, the antibodies can be sequenced and subsequently prepared by recombinant techniques. Humanization and chimerization of murine antibodies and antibody fragments are well known to those skilled in the art. The use of antibody components derived from humanized, chimeric or human antibodies obviates potential problems associated with the immunogenicity of murine constant regions.

Chimeric Antibodies

A chimeric antibody is a recombinant protein in which the variable regions of a human antibody have been replaced by the variable regions of, for example, a mouse antibody, including the complementarity-determining regions (CDRs) of the mouse antibody. Chimeric antibodies exhibit decreased immunogenicity and increased stability when administered to a subject. General techniques for cloning murine immunoglobulin variable domains are disclosed, for example, in Orlandi et al., *Proc. Nat'l Acad. Sci. USA* 86: 3833 (1989). Techniques for constructing chimeric antibodies are well known to those of skill in the art. As an example, Leung et al., *Hybridoma* 13:469 (1994), produced an LL2 chimera by combining DNA sequences encoding the $V_\kappa$ and $V_H$ domains of murine LL2, an anti-CD22 monoclonal antibody, with respective human κ and $IgG_1$ constant region domains.

Humanized Antibodies

Techniques for producing humanized MAbs are well known in the art (see, e.g., Jones et al., *Nature* 321: 522 (1986), Riechmann et al., *Nature* 332: 323 (1988), Verhoeyen et al., *Science* 239: 1534 (1988), Carter et al., *Proc. Nat'l Acad. Sci. USA* 89: 4285 (1992), Sandhu, *Crit. Rev. Biotech.* 12: 437 (1992), and Singer et al., *J. Immun.* 150: 2844 (1993)). A chimeric or murine monoclonal antibody may be humanized by transferring the mouse CDRs from the heavy and light variable chains of the mouse immunoglobulin into the corresponding variable domains of a human antibody. The mouse framework regions (FR) in the chimeric monoclonal antibody are also replaced with human FR sequences. As simply transferring mouse CDRs into human FRs often results in a reduction or even loss of antibody affinity, additional modification might be required in order to restore the original affinity of the murine antibody. This can be accomplished by the replacement of one or more human residues in the FR regions with their murine counterparts to obtain an antibody that possesses good binding affinity to its epitope. See, for example, Tempest et al., *Biotechnology* 9:266 (1991) and Verhoeyen et al., *Science* 239: 1534 (1988). Generally, those human FR amino acid residues that differ from their murine counterparts and are located close to or touching one or more CDR amino acid residues would be candidates for substitution.

Human Antibodies

Methods for producing fully human antibodies using either combinatorial approaches or transgenic animals transformed with human immunoglobulin loci are known in the art (e.g., Mancini et al., 2004, *New Microbiol.* 27:315-28; Conrad and Scheller, 2005, *Comb. Chem. High Throughput Screen.* 8:117-26; Brekke and Loset, 2003, *Curr. Opin. Phamacol.* 3:544-50). A fully human antibody also can be constructed by genetic or chromosomal transfection methods, as well as phage display technology, all of which are known in the art. See for example, McCafferty et al., *Nature* 348:552-553 (1990). Such fully human antibodies are expected to exhibit even fewer side effects than chimeric or humanized antibodies and to function in vivo as essentially endogenous human antibodies. In certain embodiments, the claimed methods and procedures may utilize human antibodies produced by such techniques.

In one alternative, the phage display technique may be used to generate human antibodies (e.g., Dantas-Barbosa et al., 2005, *Genet. Mol. Res.* 4:126-40). Human antibodies may be generated from normal humans or from humans that exhibit a particular disease state, such as cancer (Dantas-Barbosa et al., 2005). The advantage to constructing human antibodies from a diseased individual is that the circulating antibody repertoire may be biased towards antibodies against disease-associated antigens.

In one non-limiting example of this methodology, Dantas-Barbosa et al. (2005) constructed a phage display library of human Fab antibody fragments from osteosarcoma patients. Generally, total RNA was obtained from circulating blood lymphocytes (Id.). Recombinant Fab were cloned from the μ, γ and κ chain antibody repertoires and inserted into a phage display library (Id.). RNAs were converted to cDNAs and used to make Fab cDNA libraries using specific primers against the heavy and light chain immunoglobulin sequences (Marks et al., 1991, *J. Mol. Biol.* 222:581-97). Library construction was performed according to Andris-Widhopf et al. (2000, In: *Phage Display Laboratory Manual*, Barbas et al. (eds), $1^{st}$ edition, Cold Spring Harbor Laboratory Press, Cold Spring Harbor, N.Y. pp. 9.1 to 9.22). The final Fab fragments were digested with restriction endonucleases and inserted into the bacteriophage genome to make the phage display library. Such libraries may be screened by standard phage display methods, as known in the art (see, e.g., Pasqualini and Ruoslahti, 1996, Nature 380:364-366; Pasqualini, 1999, The Quart. J. Nucl. Med. 43:159-162).

Phage display can be performed in a variety of formats, for their review, see e.g. Johnson and Chiswell, *Current Opinion in Structural Biology* 3:5564-571 (1993). Human antibodies may also be generated by in vitro activated B cells. See U.S. Pat. Nos. 5,567,610 and 5,229,275, incorporated herein by reference in their entirety. The skilled artisan will realize that these techniques are exemplary and any known method for making and screening human antibodies or antibody fragments may be utilized.

In another alternative, transgenic animals that have been genetically engineered to produce human antibodies may be used to generate antibodies against essentially any immunogenic target, using standard immunization protocols. Methods for obtaining human antibodies from transgenic mice are disclosed by Green et al., *Nature Genet.* 7:13 (1994), Lonberg et al., *Nature* 368:856 (1994), and Taylor et al., *Int. Immun.* 6:579 (1994). A non-limiting example of such a system is the XenoMouse® (e.g., Green et al., 1999, *J. Immunol. Methods* 231:11-23) from Abgenix (Fremont, Calif.). In the XenoMouse® and similar animals, the mouse antibody genes have been inactivated and replaced by functional human antibody genes, while the remainder of the mouse immune system remains intact.

The XenoMouse® was transformed with germline-configured YACs (yeast artificial chromosomes) that contained portions of the human IgH and Igkappa loci, including the majority of the variable region sequences, along accessory genes and regulatory sequences. The human variable region repertoire may be used to generate antibody producing B cells, which may be processed into hybridomas by known techniques. A XenoMouse® immunized with a target antigen will produce human antibodies by the normal immune response, which may be harvested and/or produced by standard techniques discussed above. A variety of strains of XenoMouse® are available, each of which is capable of producing a different class of antibody. Transgenically produced human antibodies have been shown to have therapeutic potential, while retaining the pharmacokinetic properties of normal human antibodies (Green et al., 1999). The skilled artisan will realize that the claimed compositions and methods are not limited to use of the XenoMouse® system but may utilize any transgenic animal that has been genetically engineered to produce human antibodies.

Antibody Fragments

Antibody fragments which recognize specific epitopes can be generated by known techniques. Antibody fragments are antigen binding portions of an antibody, such as $F(ab')_2$, Fab', $F(ab)_2$, Fab, Fv, sFv and the like. $F(ab')_2$ fragments can be produced by pepsin digestion of the antibody molecule and Fab' fragments can be generated by reducing disulfide bridges of the $F(ab')_2$ fragments. Alternatively, Fab' expression libraries can be constructed (Huse et al., 1989, *Science,* 246:1274-1281) to allow rapid and easy identification of monoclonal Fab' fragments with the desired specificity. $F(ab)_2$ fragments may be generated by papain digestion of an antibody and Fab fragments obtained by disulfide reduction.

A single chain Fv molecule (scFv) comprises a VL domain and a VH domain. The VL and VH domains associate to form a target binding site. These two domains are further covalently linked by a peptide linker (L). Methods for making scFv molecules and designing suitable peptide linkers are described in U.S. Pat. Nos. 4,704,692, 4,946,778, R. Raag and M. Whitlow, "*Single Chain Fvs.*" FASEB Vol 9:73-80 (1995) and R. E. Bird and B. W. Walker, "*Single Chain Antibody Variable Regions,*" TIBTECH, Vol 9: 132-137 (1991).

Techniques for producing single domain antibodies (DABs) are also known in the art, as disclosed for example in Cossins et al. (2006, Prot Express Purif 51:253-259), incorporated herein by reference.

An antibody fragment can be prepared by proteolytic hydrolysis of the full length antibody or by expression in *E. coli* or another host of the DNA coding for the fragment. An antibody fragment can be obtained by pepsin or papain digestion of full length antibodies by conventional methods. These methods are described, for example, by Goldenberg, U.S. Pat. Nos. 4,036,945 and 4,331,647 and references contained therein. Also, see Nisonoff et al., *Arch Biochem. Biophys.* 89: 230 (1960); Porter, *Biochem. J.* 73: 119 (1959), Edelman et al., in METHODS IN ENZYMOLOGY VOL. 1, page 422 (Academic Press 1967), and Coligan at pages 2.8.1-2.8.10 and 2.10.-2.10.4.

Known Antibodies

Antibodies of use may be commercially obtained from a wide variety of known sources. For example, a variety of antibody secreting hybridoma lines are available from the American Type Culture Collection (ATCC, 10801 University Blvd., Manassas, Va. 20110-2209). A large number of antibodies against various disease targets, including but not limited to tumor-associated antigens, have been deposited at the ATCC and/or have published variable region sequences and are available for use in the claimed methods and compositions. See, e.g., U.S. Pat. Nos. 7,312,318; 7,282,567; 7,151,164; 7,074,403; 7,060,802; 7,056,509; 7,049,060; 7,045,132; 7,041,803; 7,041,802; 7,041,293; 7,038,018; 7,037,498; 7,012,133; 7,001,598; 6,998,468; 6,994,976; 6,994,852; 6,989,241; 6,974,863; 6,965,018; 6,964,854; 6,962,981; 6,962,813; 6,956,107; 6,951,924; 6,949,244; 6,946,129; 6,943,020; 6,939,547; 6,921,645; 6,921,645; 6,921,533; 6,919,433; 6,919,078; 6,916,475; 6,905,681; 6,899,879; 6,893,625; 6,887,468; 6,887,466; 6,884,594; 6,881,405; 6,878,812; 6,875,580; 6,872,568; 6,867,006; 6,864,062; 6,861,511; 6,861,227; 6,861,226; 6,838,282; 6,835,549; 6,835,370; 6,824,780; 6,824,778; 6,812,206; 6,793,924; 6,783,758; 6,770,450; 6,767,711; 6,764,688; 6,764,681; 6,764,679; 6,743,898; 6,733,981; 6,730,307; 6,720,155; 6,716,966; 6,709,653; 6,693,176; 6,692,908; 6,689,607; 6,689,362; 6,689,355; 6,682,737; 6,682,736; 6,682,734; 6,673,344; 6,653,104; 6,652,852; 6,635,482; 6,630,144; 6,610,833; 6,610,294; 6,605,441; 6,605,279; 6,596,852; 6,592,868; 6,576,745; 6,572,856; 6,566,076; 6,562,618; 6,545,130; 6,544,749; 6,534,058; 6,528,625; 6,528,269; 6,521,227; 6,518,404; 6,511,665; 6,491,915; 6,488,930; 6,482,598; 6,482,408; 6,479,247; 6,468,531; 6,468,529; 6,465,173; 6,461,823; 6,458,356; 6,455,044; 6,455,040, 6,451,310; 6,444,206, 6,441,143; 6,432,404; 6,432,402; 6,419,928; 6,413,726; 6,406,694; 6,403,770; 6,403,091; 6,395,276; 6,395,274; 6,387,350; 6,383,759; 6,383,484; 6,376,654; 6,372,215; 6,359,126; 6,355,481; 6,355,444; 6,355,245; 6,355,244; 6,346,246; 6,344,198; 6,340,571; 6,340,459; 6,331,175; 6,306,393; 6,254,868; 6,187,287; 6,183,744; 6,129,914; 6,120,767; 6,096,289; 6,077,499; 5,922,302; 5,874,540; 5,814,440; 5,798,229; 5,789,554; 5,776,456; 5,736,119; 5,716,595; 5,677,136; 5,587,459; 5,443,953, 5,525,338. These are exemplary only and a wide variety of other antibodies and their hybridomas are known in the art. The skilled artisan will realize that antibody sequences or antibody-secreting hybridomas against almost any disease-associated antigen may be obtained by a simple search of the ATCC, NCBI and/or USPTO databases for antibodies against a selected disease-associated target of interest. The antigen binding domains of the cloned antibodies may be amplified, excised, ligated into an expression vector, transfected into an adapted host cell and used for protein production, using standard techniques well known in the art.

Bi-Specific Antibodies

In certain embodiments, the anti-HLA-DR antibodies disclosed herein may be used in combination with another molecule attached to the antibody. Attachment may be either covalent or non-covalent. In some embodiments, a anti-HLA-DR antibody may be attached to a bi-specific antibody, i.e., an antibody that has two different binding sites, one for HLA-DR antibody and another for a different target antigen, such as a hapten or a disease-associated antigen. Methods for construction and use of bi-specific and multi-specific antibodies are disclosed, for example, in U.S. Pat. Nos. 6,962,702; 7,074,405; 7,230,084; 7,300,644; 7,429,381 and 7,563,439, the Examples section of each of which is incorporated herein by reference.

Where the bi-specific antibody is targeted in part against a tumor-associated antigen, exemplary types of tumors that may be targeted include acute lymphoblastic leukemia, acute myelogenous leukemia, biliary cancer, breast cancer, cervical cancer, chronic lymphocytic leukemia, chronic myelogenous leukemia, colorectal cancer, endometrial cancer, esophageal, gastric, head and neck cancer, Hodgkin's lymphoma, lung cancer, medullary thyroid, non-Hodgkin's lymphoma, ovarian cancer, pancreatic cancer, glioma, melanoma, liver cancer, prostate cancer, and urinary bladder cancer Preferred are tumors that have constitutive expression of HLA-DR.

Pre-Targeting

One strategy for use of bi-specific antibodies includes pre-targeting methodologies, in which therapeutic agent attached to a targetable construct is administered to a subject after a bi-specific antibody has been administered. Pretargeting methods have been developed to increase the target:background ratios of detection or therapeutic agents Examples of pre-targeting and biotin/avidin approaches are described, for example, in Goodwin et al, U.S. Pat. No. 4,863,713; Goodwin et al, J Nucl Med 29:226, 1988; Hnatowich et al, J Nucl Med 28:1294, 1987; Oehr et al, J Nucl Med 29:728, 1988; Klibanov et al, J Nucl Med 29:1951, 1988; Sinitsyn et al, J Nucl Med 3:66, 1989; Kalofonos et al, J Nucl Med 31:1791, 199; Schechter et al, Int J Cancer 48:167, 1991; Paganelli et al, Cancer Res 51:596, 1991; Paganelli et al, Nucl Med Commun 12:211, 1991; U.S. Pat. No. 5,256,395; Stickney et al, Cancer Res 51:665, 1991; Yuan et al, Cancer Res 51:3119, 1991; U.S. Pat. Nos. 6,77,499; 6,472,511; the Examples section of each of which is incorporated herein by reference.

In certain embodiments, bispecific antibodies and targetable constructs may be of use in treating and/or imaging normal or diseased tissue and organs, for example using the methods described in U.S. Pat. Nos. 6,126,916; 5,772,981; 5,746,996; 5,328,679; and 5,128,119, each incorporated herein by reference.

Immunoconjugates

In certain embodiments, the anti-HLA-DR antibody or fragment may be conjugated to one or more therapeutic or diagnostic agents. The therapeutic agents do not need to be the same but can be different, e.g. a drug and a radioisotope. For example, $^{131}I$ can be incorporated into a tyrosine of an antibody or fusion protein and a drug attached to an epsilon amino group of a lysine residue. Therapeutic and diagnostic agents also can be attached, for example to reduced SH groups and/or to carbohydrate side chains. Many methods for making covalent or non-covalent conjugates of therapeutic or diagnostic agents with antibodies or fusion proteins are known in the art and any such known method may be utilized.

A therapeutic or diagnostic agent can be attached at the hinge region of a reduced antibody component via disulfide bond formation. Alternatively, such agents can be attached using a heterobifunctional cross-linker, such as N-succinyl 3-(2-pyridyldithio)propionate (SPDP). Yu et al., *Int. J. Cancer* 56: 244 (1994). General techniques for such conjugation are well-known in the art. See, for example, Wong, CHEMISTRY OF PROTEIN CONJUGATION AND CROSS-LINKING (CRC Press 1991); Upeslacis et al., "Modification of Antibodies by Chemical Methods," in MONOCLONAL ANTIBODIES: PRINCIPLES AND APPLICATIONS, Birch et al. (eds.), pages 187-230 (Wiley-Liss, Inc. 1995); Price, "Production and Characterization of Synthetic Peptide-Derived Antibodies," in MONOCLONAL ANTIBODIES: PRODUCTION, ENGINEERING AND CLINICAL APPLICATION, Ritter et al. (eds.), pages 60-84 (Cambridge University Press 1995). Alternatively, the therapeutic or diagnostic agent can be conjugated via a carbohydrate moiety in the Fc region of the antibody. The carbohydrate group can be used to increase the loading of the same agent that is bound to a thiol group, or the carbohydrate moiety can be used to bind a different therapeutic or diagnostic agent.

Methods for conjugating peptides to antibody components via an antibody carbohydrate moiety are well-known to those of skill in the art. See, for example, Shih et al., *Int. J. Cancer* 41: 832 (1988); Shih et al., *Int. J. Cancer* 46: 1101 (1990); and Shih et al., U.S. Pat. No. 5,057,313, incorporated herein in their entirety by reference. The general method involves reacting an antibody component having an oxidized carbohydrate portion with a carrier polymer that has at least one free amine function. This reaction results in an initial Schiff base (imine) linkage, which can be stabilized by reduction to a secondary amine to form the final conjugate.

The Fc region may be absent if the antibody used as the antibody component of the immunoconjugate is an antibody fragment. However, it is possible to introduce a carbohydrate moiety into the light chain variable region of a full length antibody or antibody fragment. See, for example, Leung et al., *J. Immunol.* 154: 5919 (1995); Hansen et al., U.S. Pat. No. 5,443,953 (1995), Leung et al., U.S. Pat. No. 6,254,868, incorporated herein by reference in their entirety. The engineered carbohydrate moiety is used to attach the therapeutic or diagnostic agent.

In some embodiments, a chelating agent may be attached to an antibody, antibody fragment or fusion protein and used to chelate a therapeutic or diagnostic agent, such as a radionuclide. Exemplary chelators include but are not limited to DTPA (such as Mx-DTPA), DOTA, TETA, NETA or NOTA. Methods of conjugation and use of chelating agents to attach metals or other ligands to proteins are well known in the art (see, e.g., U.S. patent application Ser. No. 12/112,289, incorporated herein by reference in its entirety).

In certain embodiments, radioactive metals or paramagnetic ions may be attached to proteins or peptides by reaction with a reagent having a long tail, to which may be attached a multiplicity of chelating groups for binding ions. Such a tail can be a polymer such as a polylysine, polysaccharide, or other derivatized or derivatizable chains having pendant groups to which can be bound chelating groups such as, e.g., ethylenediaminetetraacetic acid (EDTA), diethylenetriaminepentaacetic acid (DTPA), porphyrins, polyamines, crown ethers, bis-thiosemicarbazones, polyoximes, and like groups known to be useful for this purpose.

Chelates may be directly linked to antibodies or peptides, for example as disclosed in U.S. Pat. No. 4,824,659, incorporated herein in its entirety by reference. Particularly useful metal-chelate combinations include 2-benzyl-DTPA and its monomethyl and cyclohexyl analogs, used with diagnostic isotopes in the general energy range of 60 to 4,000 keV, such as $^{125}I$, $^{131}I$, $^{123}I$, $^{124}I$, $^{62}Cu$, $^{64}Cu$, $^{18}F$, $^{111}In$, $^{67}Ga$, $^{68}Ga$, $^{99m}Tc$, $^{94m}Tc$, $^{11}C$, $^{13}N$, $^{15}O$ $^{76}Br$, for radioimaging. The same chelates, when complexed with non-radioactive metals, such as manganese, iron and gadolinium are useful for MRI. Macrocyclic chelates such as NOTA, DOTA, and TETA are of use with a variety of metals and radiometals, most particularly with radionuclides of gallium, yttrium and copper, respectively. Such metal-chelate complexes can be made very stable by tailoring the ring size to the metal of interest. Other ring-type chelates such as macrocyclic polyethers, which are of interest for stably binding nuclides, such as $^{223}$Ra for RAIT are encompassed.

More recently, methods of $^{18}$F-labeling of use in PET scanning techniques have been disclosed, for example by reaction of F-18 with a metal or other atom, such as aluminum. The $^{18}$F-Al conjugate may be complexed with chelating groups, such as DOTA, NOTA or NETA that are attached directly to antibodies or used to label targetable constructs in pre-targeting methods. Such F-18 labeling techniques are disclosed in U.S. patent application Ser. No. 12/112,289, filed Apr. 30, 2008, the entire text of which is incorporated herein by reference.

Therapeutic Agents

In alternative embodiments, therapeutic agents such as cytotoxic agents, anti-angiogenic agents, pro-apoptotic agents, antibiotics, hormones, hormone antagonists, chemokines, drugs, prodrugs, toxins, enzymes or other agents may be used, either conjugated to the subject anti-HLA-DR antibodies or separately administered before, simultaneously with, or after the antibody. Drugs of use may possess a pharmaceutical property selected from the group consisting of antimitotic, antikinase, alkylating, antimetabolite, antibiotic, alkaloid, anti-angiogenic, pro-apoptotic agents and combinations thereof.

Exemplary drugs of use may include 5-fluorouracil, aplidin, azaribine, anastrozole, anthracyclines, bendamustine, bleomycin, bortezomib, bryostatin-1, busulfan, calicheamycin, camptothecin, carboplatin, 10-hydroxycamptothecin, carmustine, CELEBREX® (celecoxib), chlorambucil, cisplatinum, Cox-2 inhibitors, irinotecan (CPT-11), SN-38, carboplatin, cladribine, camptothecans, cyclophosphamide, cytarabine, dacarbazine, docetaxel, dactinomycin, daunorubicin, doxorubicin, 2-pyrrolinodoxorubicine (2P-DOX), cyano-morpholino doxorubicin, doxorubicin glucuronide, epirubicin glucuronide, estramustine, epipodophyllotoxin, estrogen receptor binding agents, etoposide (VP16), etoposide glucuronide, etoposide phosphate, floxuridine (FUdR), 3',5'-O-dioleoyl-FudR (FUdR-dO), fludarabine, flutamide, farnesyl-protein transferase inhibitors, gemcitabine, hydroxyurea, idarubicin, ifosfamide, L-asparaginase, lenolidamide, leucovorin, lomustine, mechlorethamine, melphalan, mercaptopurine, 6-mercaptopurine, methotrexate, mitoxantrone, mithramycin, mitomycin, mitotane, navelbine, nitrosurea, plicomycin, procarbazine, paclitaxel, pentostatin, PSI-341, raloxifene, semustine, streptozocin, tamoxifen, temazolomide (an aqueous form of DTIC), transplatinum, thalidomide, thioguanine, thiotepa, teniposide, topotecan, uracil mustard, vinorelbine, vinblastine, vincristine and vinca alkaloids.

Toxins of use may include ricin, abrin, alpha toxin, saporin, ribonuclease (RNase), e.g., onconase, DNase I, *Staphylococcal* enterotoxin-A, pokeweed antiviral protein, gelonin, diphtheria toxin, *Pseudomonas* exotoxin, and *Pseudomonas* endotoxin.

Chemokines of use may include RANTES, MCAF, MIP1-alpha, MIP1-Beta and IP-10.

In certain embodiments, anti-angiogenic agents, such as angiostatin, baculostatin, canstatin, maspin, anti-VEGF antibodies, anti-P1GF peptides and antibodies, anti-vascular growth factor antibodies, anti-Flk-1 antibodies, anti-Flt-1 antibodies and peptides, anti-Kras antibodies, anti-cMET antibodies, anti-MIF (macrophage migration-inhibitory factor) antibodies, laminin peptides, fibronectin peptides, plasminogen activator inhibitors, tissue metalloproteinase inhibitors, interferons, interleukin-12, IP-10, Gro-β, thrombospondin, 2-methoxyoestradiol, proliferin-related protein, carboxiamidotriazole, CM101, Marimastat, pentosan polysulphate, angiopoietin-2, interferon-alpha, herbimycin A, PNU145156E, 16K prolactin fragment, Linomide (roquinimex), thalidomide, pentoxifylline, genistein, TNP-470, endostatin, paclitaxel, accutin, angiostatin, cidofovir, vincristine, bleomycin, AGM-1470, platelet factor 4 or minocycline may be of use.

Immunomodulators of use may be selected from a cytokine, a stem cell growth factor, a lymphotoxin, an hematopoietic factor, a colony stimulating factor (CSF), an interferon (IFN), erythropoietin, thrombopoietin and a combination thereof. Specifically useful are lymphotoxins such as tumor necrosis factor (TNF), hematopoietic factors, such as interleukin (IL), colony stimulating factor, such as granulocyte-colony stimulating factor (G-CSF) or granulocyte macrophage-colony stimulating factor (GM-CSF), interferon, such as interferons-α, -β or -γ, and stem cell growth factor, such as that designated "S1 factor". Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; prostaglandin, fibroblast growth factor; prolactin; placental lactogen, OB protein; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); interleukins (ILs) such as IL-1, IL-1α, IL-2, IL-3, IL-4, IL-5, IL-6, IL-7, IL-8, IL-9, IL-10, IL-11, IL-12; IL-13, IL-14, IL-15, IL-16, IL-17, IL-18, IL-21, IL-25, LIF, kit-ligand or FLT-3, angiostatin, thrombospondin, endostatin, tumor necrosis factor and LT.

Radionuclides of use include, but are not limited to—$^{111}$In, $^{177}$Lu, $^{212}$Bi, $^{213}$Bi, $^{211}$At, $^{62}$Cu, $^{67}$Cu, $^{90}$Y, $^{125}$I, $^{131}$I, $^{32}$P, $^{33}$P, $^{47}$Sc, $^{111}$Ag, $^{67}$Ga, $^{142}$Pr, $^{153}$Sm, $^{161}$Tb, $^{166}$Dy, $^{166}$Ho, $^{186}$Re, $^{188}$Re, $^{189}$Re, $^{212}$Pb, $^{223}$Ra, $^{225}$Ac, $^{59}$Fe, $^{75}$Se, $^{77}$As, $^{89}$Sr, $^{99}$Mo, $^{105}$Rh, $^{109}$Pd, $^{143}$Pr, $^{149}$Pm, $^{169}$Er, $^{194}$Ir, $^{198}$Au, $^{199}$Au, and $^{211}$Pb. The therapeutic radionuclide preferably has a decay-energy in the range of 20 to 6,000 keV, preferably in the ranges 60 to 200 keV for an Auger emitter, 100-2,500 keV for a beta emitter, and 4,000-6,000 keV for an alpha emitter. Maximum decay energies of useful beta-particle-emitting nuclides are preferably 20-5,000 keV, more preferably 100-4,000 keV, and most preferably 500-2,500 keV. Also preferred are radionuclides that substantially decay with Auger-emitting particles. For example, Co-58, Ga-67, Br-80m, Tc-99m, Rh-103m, Pt-109, In-111, Sb-119, 1-125, Ho-161, Os-189m and Ir-192. Decay energies of useful beta-particle-emitting nuclides are preferably <1,000 keV, more preferably <100 keV, and most preferably <70 keV. Also preferred are radionuclides that substantially decay with generation of alpha-particles. Such radionuclides include, but are not limited to: Dy-152, At-211, Bi-212, Ra-223, Rn-219, Po-215, Bi-211, Ac-225, Fr-221, At-217, Bi-213 and Fm-255. Decay energies of useful alpha-particle-emitting radionuclides are preferably 2,000-10,000 keV, more preferably 3,000-8,000 keV, and most preferably 4,000-7,000 keV. Additional potential radioisotopes of use include $^{11}C$, $^{13}N$, $^{15}O$, $^{75}Br$, $^{198}Au$, $^{224}Ac$, $^{126}I$, $^{133}I$, $^{77}Br$, $^{113m}In$, $^{95}Ru$, $^{97}Ru$, $^{103}Ru$, $^{105}Ru$, $^{107}Hg$, $^{203}Hg$, $^{121m}Te$, $^{122m}Te$, $^{125m}Te$, $^{165}Tm$, $^{167}Tm$, $^{168}Tm$, $^{197}Pt$, $^{109}Pd$, $^{105}Rh$, $^{142}Pr$, $^{143}Pr$, $^{161}Tb$, $^{166}Ho$, $^{199}Au$, $^{57}Co$, $^{58}Co$, $^{51}Cr$, $^{59}Fe$, $^{75}Se$, $^{201}Tl$, $^{225}Ac$, $^{76}Br$, $^{169}Yb$, and the like. Some useful diagnostic nuclides may include $^{18}F$, $^{52}Fe$, $^{62}Cu$, $^{64}Cu$, $^{67}Cu$, $^{67}Ga$, $^{68}Ga$, $^{86}Y$, $^{89}Zr$, $^{94}Tc$, $^{94m}Tc$, $^{99m}Tc$, or $^{111}In$. In certain embodiments, anti-IGF-1R antibodies, such as hR1, may be of use in combination with therapeutic radionuclides for sensitization of tumors to radiation therapy (see, e.g., Allen et al., 2007, Cancer Res. 67:1155).

Therapeutic agents may include a photoactive agent or dye. Fluorescent compositions, such as fluorochrome, and other chromogens, or dyes, such as porphyrins sensitive to visible light, have been used to detect and to treat lesions by directing the suitable light to the lesion. In therapy, this has been termed photoradiation, phototherapy, or photodynamic therapy. See Joni et al. (eds.), PHOTODYNAMIC THERAPY OF TUMORS AND OTHER DISEASES (Libreria Progetto 1985); van den Bergh, Chem. Britain (1986), 22:430. Moreover, monoclonal antibodies have been coupled with photoactivated dyes for achieving phototherapy. See Mew et al., J. Immunol. (1983), 130:1473; idem., Cancer Res. (1985), 45:4380; Oseroff et al., Proc. Natl. Acad. Sci. USA (1986), 83:8744; idem., Photochem. Photobiol. (1987), 46:83; Hasan et al., Prog. Clin. Biol. Res. (1989), 288:471; Tatsuta et al., Lasers Surg. Med. (1989), 9:422; Pelegrin et al., Cancer (1991), 67:2529.

Other useful therapeutic agents may comprise oligonucleotides, especially antisense oligonucleotides that preferably are directed against oncogenes and oncogene products, such as bcl-2 or p53. A preferred form of therapeutic oligonucleotide is siRNA.

Diagnostic Agents

Diagnostic agents are preferably selected from the group consisting of a radionuclide, a radiological contrast agent, a paramagnetic ion, a metal, a fluorescent label, a chemiluminescent label, an ultrasound contrast agent and a photoactive agent. Such diagnostic agents are well known and any such known diagnostic agent may be used. Non-limiting examples of diagnostic agents may include a radionuclide such as $^{110}In$, $^{111}In$, $^{177}Lu$, $^{18}F$, $^{52}Fe$, $^{62}Cu$, $^{64}Cu$, $^{67}Cu$, $^{67}Ga$, $^{68}Ga$, $_{86}Y$, $^{90}Y$, $^{89}Zr$, $^{94m}Tc$, $^{94}Tc$, $^{99m}Tc$, $^{120}I$, $^{123}I$, $^{124}I$, $^{125}I$, $^{131}I$, $^{154-}$ $_{158}Gd$, $^{32}P$, $^{11}C$, $^{13}N$, $^{15}O$, $^{186}Re$, $^{188}Re$, $^{51}Mn$, $^{52m}Mn$, $^{55}Co$, $^{72}As$, $^{75}Br$, $^{76}Br$, $^{82m}Rb$, $^{83}Sr$, or other gamma-, beta-, or positron-emitters. Paramagnetic ions of use may include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) or erbium (III). Metal contrast agents may include lanthanum (III), gold (III), lead (II) or bismuth (III). Ultrasound contrast agents may comprise liposomes, such as gas filled liposomes. Radiopaque diagnostic agents may be selected from compounds, barium compounds, gallium compounds, and thallium compounds. A wide variety of fluorescent labels are known in the art, including but not limited to fluorescein isothiocyanate, rhodamine, phycoerytherin, phycocyanin, allophycocyanin, o-phthaldehyde and fluorescamine. Chemiluminescent labels of use may include luminol, isoluminol, an aromatic acridinium ester, an imidazole, an acridinium salt or an oxalate ester.

Methods of Therapeutic Treatment

Various embodiments concern methods of treating a cancer in a subject, such as a mammal, including humans, domestic or companion pets, such as dogs and cats, comprising administering to the subject a therapeutically effective amount of an anti-HLA-DR antibody. In preferred embodiments, the anti-HLA-DR antibody is a humanized L243 antibody, as described in further detail in the Examples below.

In one embodiment, immunological diseases which may be treated with the subject antibodies may include, for example, joint diseases such as ankylosing spondylitis, juvenile rheumatoid arthritis, rheumatoid arthritis; neurological disease such as multiple sclerosis and myasthenia gravis; pancreatic disease such as diabetes, especially juvenile onset diabetes; gastrointestinal tract disease such as chronic active hepatitis, celiac disease, ulcerative colitis, Crohn's disease, pernicious anemia; skin diseases such as psoriasis or scleroderma; allergic diseases such as asthma and in transplantation related conditions such as graft versus host disease and allograft rejection.

The administration of anti-HLA-DR antibody can be supplemented by administering concurrently or sequentially a therapeutically effective amount of another antibody that binds to or is reactive with another antigen on the surface of the target cell. Preferred additional MAbs comprise at least one humanized, chimeric or human MAb selected from the group consisting of a MAb reactive with CD4, CD5, CD8, CD14, CD15, CD16, CD19, IGF-1R, CD20, CD21, CD22, CD23, CD25, CD30, CD32b, CD33, CD37, CD38, CD40, CD40L, CD45, CD46, CD52, CD54, CD70, CD74, CD79a, CD80, CD95, CD126, CD133, CD138, CD154, CEACAM5, CEACAM6, B7, AFP, PSMA, EGP-1, EGP-2, carbonic anhydrase IX, PAM4 antigen, MUC1, MUC2, MUC3, MUC4, MUC5, Ia, MIF, HM1.24, HLA-DR, tenascin, Flt-3, VEGFR, P1GF, ILGF, IL-6, IL-25, tenascin, TRAIL-R1, TRAIL-R2, complement factor C5, oncogene product, or a combination thereof. Various antibodies of use, such as anti-CD19, anti-CD20, and anti-CD22 antibodies, are known to those of skill in the art. See, for example, Ghetie et al., *Cancer Res.* 48:2610 (1988); Hekman et al., *Cancer Immunol. Immunother.* 32:364 (1991); Longo, *Curr. Opin. Oncol.* 8:353 (1996), U.S. Pat. Nos. 5,798,554; 6,187,287; 6,306,393; 6,676,924; 7,109,304; 7,151,164; 7,230,084; 7,230,085; 7,238,785; 7,238,786; 7,282,567; 7,300,655; 7,312,318; and U.S. Patent Application Publ. Nos. 20080131363; 20080089838; 20070172920; 20060193865; 20060210475; 20080138333; and 20080146784, each incorporated herein by reference.

The anti-HLA-DR antibody therapy can be further supplemented with the administration, either concurrently or sequentially, of at least one therapeutic agent. For example, "CVB" (1.5 g/m$^2$ cyclophosphamide, 200-400 mg/m$^2$ etoposide, and 150-200 mg/m$^2$ carmustine) is a regimen used to treat non-Hodgkin's lymphoma. Patti et al., *Eur. J. Haematol.* 51: 18 (1993). Other suitable combination chemotherapeutic regimens are well-known to those of skill in the art. See, for example, Freedman et al., "Non-Hodgkin's Lymphomas," in CANCER MEDICINE, VOLUME 2, 3rd Edition, Holland et al. (eds.), pages 2028-2068 (Lea & Febiger 1993). As an illustration, first generation chemotherapeutic regimens for treatment of intermediate-grade non-Hodgkin's lymphoma (NHL) include C-MOPP (cyclophosphamide, vincristine, procarbazine and prednisone) and CHOP (cyclophosphamide, doxorubicin, vincristine, and prednisone). A useful second generation chemotherapeutic regimen is m-BACOD (methotrexate, bleomycin, doxorubicin, cyclophosphamide, vincristine, dexamethasone and leucovorin), while a suitable third generation regimen is MACOP-B (methotrexate, doxorubicin, cyclophosphamide, vincristine, prednisone, bleomycin and leucovorin). Additional useful drugs include phenyl butyrate, bendamustine, and bryostatin-1.

The anti-HLA-DR antibody can be formulated according to known methods to prepare pharmaceutically useful compositions, whereby the anti-HLA-DR antibody is combined in a mixture with a pharmaceutically suitable excipient. Sterile phosphate-buffered saline is one example of a pharmaceutically suitable excipient. Other suitable excipients are well-known to those in the art. See, for example, Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The anti-HLA-DR antibody can be formulated for intravenous administration via, for example, bolus injection or continuous infusion. Preferably, anti-HLA-DR antibody is infused over a period of less than about 4 hours, and more preferably, over a period of less than about 3 hours. For example, the first 25-50 mg could be infused within 30 minutes, preferably even 15 min, and the remainder infused over the next 2-3 hrs. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

Additional pharmaceutical methods may be employed to control the duration of action of the anti-HLA-DR antibody. Control release preparations can be prepared through the use of polymers to complex or adsorb the anti-HLA-DR antibody. For example, biocompatible polymers include matrices of poly(ethylene-co-vinyl acetate) and matrices of a polyanhydride copolymer of a stearic acid dimer and sebacic acid. Sherwood et al., *Bio/Technology* 10: 1446 (1992). The rate of release from such a matrix depends upon the molecular weight of the anti-HLA-DR antibody, the amount of anti-HLA-DR antibody within the matrix, and the size of dispersed particles. Saltzman et al., *Biophys. J.* 55: 163 (1989); Sherwood et al., supra. Other solid dosage forms are described in Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The anti-HLA-DR antibody may also be administered to a mammal subcutaneously or even by other parenteral routes. Moreover, the administration may be by continuous infusion or by single or multiple boluses. Preferably, the anti-HLA-DR antibody is infused over a period of less than about 4 hours, and more preferably, over a period of less than about 3 hours.

More generally, the dosage of an administered anti-HLA-DR antibody for humans will vary depending upon such factors as the patient's age, weight, height, sex, general medical condition and previous medical history. It may be desirable to provide the recipient with a dosage of anti-HLA-DR antibody that is in the range of from about 1 mg/kg to 25 mg/kg as a single intravenous infusion, although a lower or higher dosage also may be administered as circumstances dictate. A dosage of 1-20 mg/kg for a 70 kg patient, for example, is 70-1,400 mg, or 41-824 $mg/m^2$ for a 1.7-m patient. The dosage may be repeated as needed, for example, once per week for 4-10 weeks, once per week for 8 weeks, or once per week for 4 weeks. It may also be given less frequently, such as every other week for several months, or monthly or quarterly for many months, as needed in a maintenance therapy.

Alternatively, an anti-HLA-DR antibody may be administered as one dosage every 2 or 3 weeks, repeated for a total of at least 3 dosages. Or, the construct may be administered twice per week for 4-6 weeks. If the dosage is lowered to approximately 200-300 $mg/m^2$ (340 mg per dosage for a 1.7-m patient, or 4.9 mg/kg for a 70 kg patient), it may be administered once or even twice weekly for 4 to 10 weeks. Alternatively, the dosage schedule may be decreased, namely every 2 or 3 weeks for 2-3 months. It has been determined, however, that even higher doses, such as 20 mg/kg once weekly or once every 2-3 weeks can be administered by slow i.v. infusion, for repeated dosing cycles. The dosing schedule can optionally be repeated at other intervals and dosage may be given through various parenteral routes, with appropriate adjustment of the dose and schedule.

In preferred embodiments, the anti-HLA-DR antibodys are of use for therapy of cancer. Examples of cancers include, but are not limited to, carcinoma, lymphoma, glioblastoma, melanoma, sarcoma, and leukemia, myeloma, or lymphoid malignancies. More particular examples of such cancers are noted below and include: squamous cell cancer (e.g., epithelial squamous cell cancer), Ewing sarcoma, Wilms tumor, astrocytomas, lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma multiforme, cervical cancer, ovarian cancer, liver cancer, bladder cancer, hepatoma, hepatocellular carcinoma, neuroendocrine tumors, medullary thyroid cancer, differentiated thyroid carcinoma, breast cancer, ovarian cancer, colon cancer, rectal cancer, endometrial cancer or uterine carcinoma, salivary gland carcinoma, kidney or renal cancer, prostate cancer, vulvar cancer, anal carcinoma, penile carcinoma, as well as head-and-neck cancer. The term "cancer" includes primary malignant cells or tumors (e.g., those whose cells have not migrated to sites in the subject's body other than the site of the original malignancy or tumor) and secondary malignant cells or tumors (e.g., those arising from metastasis, the migration of malignant cells or tumor cells to secondary sites that are different from the site of the original tumor). Cancers conducive to treatment methods of the present invention involves cells which express, over-express, or abnormally express IGF-1R.

Other examples of cancers or malignancies include, but are not limited to: Acute Childhood Lymphoblastic Leukemia, Acute Lymphoblastic Leukemia, Acute Lymphocytic Leukemia, Acute Myeloid Leukemia, Adrenocortical Carcinoma, Adult (Primary) Hepatocellular Cancer, Adult (Primary) Liver Cancer, Adult Acute Lymphocytic Leukemia, Adult Acute Myeloid Leukemia, Adult Hodgkin's Lymphoma, Adult Lymphocytic Leukemia, Adult Non-Hodgkin's Lymphoma, Adult Primary Liver Cancer, Adult Soft Tissue Sarcoma, AIDS-Related Lymphoma, AIDS-Related Malignancies, Anal Cancer, Astrocytoma, Bile Duct Cancer, Bladder Cancer, Bone Cancer, Brain Stem Glioma, Brain Tumors, Breast Cancer, Cancer of the Renal Pelvis and Ureter, Central Nervous System (Primary) Lymphoma, Central Nervous System Lymphoma, Cerebellar Astrocytoma, Cerebral Astrocytoma, Cervical Cancer, Childhood (Primary) Hepatocellular Cancer, Childhood (Primary) Liver Cancer, Childhood Acute Lymphoblastic Leukemia, Childhood Acute Myeloid Leukemia, Childhood Brain Stem Glioma, Childhood Cerebellar Astrocytoma, Childhood Cerebral Astrocytoma, Childhood Extracranial Germ Cell Tumors, Childhood Hodgkin's Disease, Childhood Hodgkin's Lymphoma, Childhood Hypothalamic and Visual Pathway Glioma, Childhood Lymphoblastic Leukemia, Childhood Medulloblastoma, Childhood Non-Hodgkin's Lymphoma, Childhood Pineal and Supratentorial Primitive Neuroectodermal Tumors, Childhood Primary Liver Cancer, Childhood Rhabdomyosarcoma, Childhood Soft Tissue Sarcoma, Childhood Visual Pathway and Hypothalamic Glioma, Chronic Lymphocytic Leukemia, Chronic Myelogenous Leukemia, Colon Cancer, Cutaneous T-Cell Lymphoma, Endocrine Pancreas Islet Cell Carcinoma, Endometrial Cancer, Ependymoma, Epithelial Cancer, Esophageal Cancer, Ewing's Sarcoma and Related Tumors, Exocrine Pancreatic Cancer, Extracranial Germ Cell Tumor, Extragonadal Germ Cell Tumor, Extrahepatic Bile Duct Cancer, Eye Cancer, Female Breast Cancer, Gaucher's Disease, Gallbladder Cancer, Gastric Cancer, Gastrointestinal Carcinoid Tumor, Gastrointestinal Tumors, Germ Cell Tumors, Gestational Trophoblastic Tumor, Hairy Cell Leukemia, Head and Neck Cancer, Hepatocellular Cancer, Hodgkin's Lymphoma, Hypergammaglobulinemia, Hypopharyngeal Cancer, Intestinal Cancers, Intraocular Melanoma, Islet Cell Carcinoma, Islet Cell Pancreatic Cancer, Kaposi's Sarcoma, Kidney Cancer, Laryngeal Cancer, Lip and Oral Cavity Cancer, Liver Cancer, Lung Cancer, Lymphoproliferative Disorders, Macroglobulinemia, Male Breast Cancer, Malignant Mesothelioma, Malignant Thymoma, Medulloblastoma, Melanoma, Mesothelioma, Metastatic Occult Primary Squamous Neck Cancer, Metastatic Primary Squamous Neck Cancer, Metastatic Squamous Neck Cancer, Multiple Myeloma, Multiple Myeloma/Plasma Cell Neoplasm, Myelodysplastic Syndrome, Myelogenous Leukemia, Myeloid Leukemia, Myeloproliferative Disorders, Nasal Cavity and Paranasal Sinus Cancer, Nasopharyngeal Cancer, Neuroblastoma, Non-Hodgkin's Lymphoma, Nonmelanoma Skin Cancer, Non-Small Cell Lung Cancer, Occult Primary Metastatic Squamous Neck Cancer, Oropharyngeal Cancer, Osteo-/Malignant Fibrous Sarcoma, Osteosarcoma/Malignant Fibrous Histiocytoma, Osteosarcoma/Malignant Fibrous Histiocytoma of Bone, Ovarian Epithelial Cancer, Ovarian Germ Cell Tumor, Ovarian Low Malignant Potential Tumor, Pancreatic Cancer, Paraproteinemias, Polycythemia vera, Parathyroid Cancer, Penile Cancer, Pheochromocytoma, Pituitary Tumor, Primary Central Nervous System Lymphoma, Primary Liver Cancer, Prostate Cancer, Rectal Cancer, Renal Cell Cancer, Renal Pelvis and Ureter Cancer, Retinoblastoma, Rhabdomyosarcoma, Salivary Gland Cancer, Sarcoidosis Sarcomas, Sezary Syndrome, Skin Cancer, Small Cell Lung Cancer, Small Intestine Cancer, Soft Tissue Sarcoma, Squamous Neck Cancer, Stomach Cancer, Supratentorial Primitive Neuroectodermal and Pineal Tumors, T-Cell Lymphoma, Testicular Cancer, Thymoma, Thyroid Cancer, Transitional Cell Cancer of the Renal Pelvis and Ureter, Transitional Renal Pelvis and Ureter Cancer, Trophoblastic Tumors, Ureter and Renal Pelvis Cell Cancer, Urethral Cancer, Uterine Cancer, Uterine Sarcoma, Vaginal Cancer, Visual Pathway and Hypothalamic Glioma, Vulvar Cancer, Waldenstrom's Macroglobulinemia, Wilms' Tumor, and any other hyperproliferative disease, besides neoplasia, located in an organ system listed above.

The methods and compositions described and claimed herein may be used to treat malignant or premalignant conditions and to prevent progression to a neoplastic or malignant state, including but not limited to those disorders described above. Such uses are indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, Basic Pathology, 2d Ed., W. B. Saunders Co., Philadelphia, pp. 68-79 (1976)).

Dysplasia is frequently a forerunner of cancer, and is found mainly in the epithelia. It is the most disorderly form of non-neoplastic cell growth, involving a loss in individual cell uniformity and in the architectural orientation of cells. Dysplasia characteristically occurs where there exists chronic irritation or inflammation. Dysplastic disorders which can be treated include, but are not limited to, anhidrotic ectodermal dysplasia, anterofacial dysplasia, asphyxiating thoracic dysplasia, atriodigital dysplasia, bronchopulmonary dysplasia, cerebral dysplasia, cervical dysplasia, chondroectodermal dysplasia, cleidocranial dysplasia, congenital ectodermal dysplasia, craniodiaphysial dysplasia, craniocarpotarsal dysplasia, craniometaphysial dysplasia, dentin dysplasia, diaphysial dysplasia, ectodermal dysplasia, enamel dysplasia, encephalo-ophthalmic dysplasia, dysplasia epiphysialis hemimelia, dysplasia epiphysialis multiplex, dysplasia epiphysialis punctata, epithelial dysplasia, faciodigitogenital dysplasia, familial fibrous dysplasia of jaws, familial white folded dysplasia, fibromuscular dysplasia, fibrous dysplasia of bone, florid osseous dysplasia, hereditary renal-retinal dysplasia, hidrotic ectodermal dysplasia, hypohidrotic ectodermal dysplasia, lymphopenic thymic dysplasia, mammary dysplasia, mandibulofacial dysplasia, metaphysial dysplasia, Mondini dysplasia, monostotic fibrous dysplasia, mucoepithelial dysplasia, multiple epiphysial dysplasia, oculoauriculovertebral dysplasia, oculodentodigital dysplasia, oculovertebral dysplasia, odontogenic dysplasia, opthalmomandibulomelic dysplasia, periapical cemental dysplasia, polyostotic fibrous dysplasia, pseudoachondroplastic spondyloepiphysial dysplasia, retinal dysplasia, septo-optic dysplasia, spondyloepiphysial dysplasia, and ventriculoradial dysplasia.

Additional pre-neoplastic disorders which can be treated include, but are not limited to, benign dysproliferative disorders (e.g., benign tumors, fibrocystic conditions, tissue hypertrophy, intestinal polyps or adenomas, and esophageal dysplasia), leukoplakia, keratoses, Bowen's disease, Farmer's Skin, solar cheilitis, and solar keratosis.

In preferred embodiments, the method of the invention is used to inhibit growth, progression, and/or metastasis of cancers, in particular those listed above.

Additional hyperproliferative diseases, disorders, and/or conditions include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, emangioblastoma, acoustic neuroma, oligodendroglioma, meningioma, melanoma, neuroblastoma, and retinoblastoma.

Expression Vectors

Still other embodiments may concern DNA sequences comprising a nucleic acid encoding an anti-HLA-DR antibody or fusion protein. Fusion proteins may comprise an antibody or fragment attached to a different antibody or fragment or to a therapeutic protein or peptide, such as a cytokine Various embodiments relate to expression vectors comprising the coding DNA sequences. The vectors may contain sequences encoding the light and heavy chain constant regions and the hinge region of a human immunoglobulin to which may be attached chimeric, humanized or human variable region sequences. The vectors may additionally contain promoters that express the encoded protein(s) in a selected host cell, enhancers and signal or leader sequences. Vectors that are particularly useful are pdHL2 or GS. More preferably, the light and heavy chain constant regions and hinge region may be from a human EU myeloma immunoglobulin, where optionally at least one of the amino acid in the allotype positions is changed to that found in a different IgG 1 allotype, and wherein optionally amino acid 253 of the heavy chain of EU based on the EU number system may be replaced with alanine See Edelman et al., *Proc. Natl. Acad. Sci. USA* 63: 78-85 (1969). In other embodiments, an IgG1 sequence may be converted to an IgG4 sequence.

The skilled artisan will realize that methods of genetically engineering expression constructs and insertion into host cells to express engineered proteins are well known in the art and a matter of routine experimentation. Host cells and methods of expression of cloned antibodies or fragments have been described, for example, in U.S. patent application Ser. No. 11/187,863, filed Jul. 25, 2005; Ser. No. 11/253,666, filed Oct. 20, 2005 and Ser. No. 11/487,215, filed Jul. 14, 2006, each incorporated herein by reference in its entirety.

Kits

Various embodiments may concern kits containing components suitable for treating or diagnosing diseased tissue in a patient. Exemplary kits may contain at least one or more anti-HLA-DR antibody as described herein. If the composition containing components for administration is not formulated for delivery via the alimentary canal, such as by oral delivery, a device capable of delivering the kit components through some other route may be included. One type of device, for applications such as parenteral delivery, is a syringe that is used to inject the composition into the body of a subject. Inhalation devices may also be used. In certain embodiments, a therapeutic agent may be provided in the form of a prefilled syringe or autoinjection pen containing a sterile, liquid formulation or lyophilized preparation.

The kit components may be packaged together or separated into two or more containers. In some embodiments, the containers may be vials that contain sterile, lyophilized formulations of a composition that are suitable for reconstitution. A kit may also contain one or more buffers suitable for reconstitution and/or dilution of other reagents. Other containers that may be used include, but are not limited to, a pouch, tray, box, tube, or the like. Kit components may be packaged and maintained sterilely within the containers. Another component that can be included is instructions to a person using a kit for its use.

Dock and Lock (DNL) method

In certain embodiments, the anti-HLA-DR antibodies or fragments may be incorporated into a multimeric complex, for example using a technique referred to as "dock-and-lock" (DNL). The DNL method exploits specific protein/protein interactions that occur between the regulatory (R) subunits of cAMP-dependent protein kinase (PKA) and the anchoring domain (AD) of A-kinase anchoring proteins (AKAPs) (Baillie et al., FEBS Letters. 2005; 579: 3264. Wong and Scott, Nat. Rev. Mol. Cell. Biol. 2004; 5: 959). PKA, which plays a central role in one of the best studied signal transduction pathways triggered by the binding of the second messenger cAMP to the R subunits, was first isolated from rabbit skeletal muscle in 1968 (Walsh et al., J. Biol. Chem. 1968; 243:3763). The structure of the holoenzyme consists of two catalytic subunits held in an inactive form by the R subunits (Taylor, J. Biol. Chem. 1989; 264:8443). Isozymes of PKA are found with two types of R subunits (RI and RII), and each type has α and β isoforms (Scott, Pharmacol. Ther. 1991; 50:123). The R subunits have been isolated only as stable dimers and the dimerization domain has been shown to consist of the first 44 amino-terminal residues (Newlon et al., Nat. Struct. Biol. 1999; 6:222). Binding of cAMP to the R subunits leads to the release of active catalytic subunits for a broad spectrum of serine/threonine kinase activities, which are oriented toward selected substrates through the compartmentalization of PKA via its docking with AKAPs (Scott et al., J. Biol. Chem. 1990; 265; 21561)

Since the first AKAP, microtubule-associated protein-2, was characterized in 1984 (Lohmann et al., Proc. Natl. Acad. Sci. USA. 1984; 81:6723), more than 50 AKAPs that localize to various suB cellular sites, including plasma membrane, actin cytoskeleton, nucleus, mitochondria, and endoplasmic reticulum, have been identified with diverse structures in species ranging from yeast to humans (Wong and Scott, Nat. Rev. Mol. Cell. Biol. 2004; 5:959). The AD of AKAPs for PKA is an amphipathic helix of 14-18 residues (Carr et al., J. Biol. Chem. 1991; 266:14188). The amino acid sequences of the AD are quite varied among individual AKAPs, with the binding affinities reported for RII dimers ranging from 2 to 90 nM (Alto et al., Proc. Natl. Acad. Sci. USA. 2003; 100:4445). Interestingly, AKAPs will only bind to dimeric R subunits. For human RIIα, the AD binds to a hydrophobic surface formed by the 23 amino-terminal residues (Colledge and Scott, Trends Cell Biol. 1999; 6:216). Thus, the dimerization domain and AKAP binding domain of human RIIα are both located within the same N-terminal 44 amino acid sequence (Newlon et al., Nat. Struct. Biol. 1999; 6:222; Newlon et al., EMBO J. 2001; 20:1651), which is termed the DDD herein.

DDD of Human RIIα and AD of AKAPs as Linker Modules

We have developed a platform technology to utilize the DDD of human RIIα and the AD of AKAP proteins as an excellent pair of linker modules for docking any two entities, referred to hereafter as A and B, into a noncovalent complex, which could be further locked into a stably tethered structure through the introduction of cysteine residues into both the DDD and AD at strategic positions to facilitate the formation of disulfide bonds. The general methodology of the "dock-and-lock" approach is as follows. Entity A is constructed by linking a DDD sequence to a precursor of A, resulting in a first component hereafter referred to as a. Because the DDD sequence would effect the spontaneous formation of a dimer, A would thus be composed of $a_2$. Entity B is constructed by linking an AD sequence to a precursor of B, resulting in a second component hereafter referred to as b. The dimeric motif of DDD contained in $a_2$ will create a docking site for binding to the AD sequence contained in b, thus facilitating a ready association of $a_2$ and b to form a binary, trimeric complex composed of $a_2b$. This binding event is made irreversible with a subsequent reaction to covalently secure the two entities via disulfide bridges, which occurs very efficiently based on the principle of effective local concentration because the initial binding interactions should bring the reactive thiol groups placed onto both the DDD and AD into proximity (Chimura et al., Proc. Natl. Acad. Sci. USA. 2001; 98:8480) to ligate site-specifically.

In preferred embodiments, the anti-HLA-DR MAb DNL constructs may be based on a variation of the $a_2b$ structure, in which an IgG immunoglobulin molecule (e.g., hL243) is attached at its C-terminal end to two copies of an AD moiety. Each AD moiety is capable of binding to two DDD moieties in the form of a dimer. By attaching a cytokine or other therapeutic protein or peptide to each DDD moiety, four copies of cytokine or other therapeutic moiety are conjugated to each IgG molecule.

By attaching the DDD and AD away from the functional groups of the two precursors, such site-specific ligations are also expected to preserve the original activities of the two precursors. This approach is modular in nature and potentially can be applied to link, site-specifically and covalently, a wide range of substances. The DNL method was disclosed in U.S. Pat. Nos. 7,550,143; 7,521,056; 76,534,866; 7,527,787 and 7,666,400, the Examples section of each incorporated herein by reference.

In preferred embodiments, the effector moiety is a protein or peptide, more preferably an antibody, antibody fragment or cytokine, which can be linked to a DDD or AD unit to form a fusion protein or peptide. A variety of methods are known for making fusion proteins, including nucleic acid synthesis, hybridization and/or amplification to produce a synthetic double-stranded nucleic acid encoding a fusion protein of interest. Such double-stranded nucleic acids may be inserted into expression vectors for fusion protein production by standard molecular biology techniques (see, e.g. Sambrook et al., Molecular Cloning, A laboratory manual, 2$^{nd}$ Ed, 1989). In such preferred embodiments, the AD and/or DDD moiety may be attached to either the N-terminal or C-terminal end of an effector protein or peptide. However, the skilled artisan will realize that the site of attachment of an AD or DDD moiety to an effector moiety may vary, depending on the chemical nature of the effector moiety and the part(s) of the effector moiety involved in its physiological activity. Site-specific attachment of a variety of effector moieties may be performed using techniques known in the art, such as the use of bivalent cross-linking reagents and/or other chemical conjugation techniques.

DDD and AD Sequence Variants

In certain embodiments, the AD and DDD sequences incorporated into the anti-HLA-DR MAb DNL complex comprise the amino acid sequences of DDD1 (SEQ ID NO:1) and AD1 (SEQ ID NO:3) below. In more preferred embodiments, the AD and DDD sequences comprise the amino acid sequences of DDD2 (SEQ ID NO:2) and AD2 (SEQ ID NO:4), which are designed to promote disulfide bond formation between the DDD and AD moieties.

DDD1
(SEQ ID NO: 1)
SHIQIPPGLTELLQGYTVEVLRQQPPDLVEFAVEYFTRLREARA

DDD2
(SEQ ID NO: 2)
CGHIQIPPGLTELLQGYTVEVLRQQPPDLVEFAVEYFTRLREARA

AD1
(SEQ ID NO: 3)
QIEYLAKQIVDNAIQQA

AD2
(SEQ ID NO: 4)
CGQIEYLAKQIVDNAIQQAGC

However, in alternative embodiments sequence variants AD and/or DDD moieties may be utilized in construction of the anti-HLA-DR MAb DNL complexes. The structure-function relationships of the AD and DDD domains have been the subject of investigation. (See, e.g., Burns-Hamuro et al., 2005, Protein Sci 14:2982-92; Carr et al., 2001, J Biol Chem 276:17332-38; Alto et al., 2003, Proc Natl Acad Sci USA 100:4445-50; Hundsrucker et al., 2006, Biochem J 396:297-306; Stokka et al., 2006, Biochem J 400:493-99; Gold et al., 2006, Mol Cell 24:383-95; Kinderman et al., 2006, Mol Cell 24:397-408, the entire text of each of which is incorporated herein by reference.)

For example, Kinderman et al. (2006) examined the crystal structure of the AD-DDD binding interaction and concluded that the human DDD sequence contained a number of conserved amino acid residues that were important in either dimer formation or AKAP binding, underlined below in SEQ ID NO:1. (See FIG. 1 of Kinderman et al., 2006, incorporated herein by reference.) The skilled artisan will realize that in designing sequence variants of the DDD sequence, one would desirably avoid changing any of the underlined residues, while conservative amino acid substitutions might be made for residues that are less critical for dimerization and AKAP binding. Thus, a potential alternative DDD sequence of use for construction of DNL complexes is shown in SEQ ID NO:5, wherein "X" represents a conservative amino acid substitution. Conservative amino acid substitutions are discussed in more detail below, but could involve for example substitution of an aspartate residue for a glutamate residue, or a leucine or valine residue for an isoleucine residue, etc. Such conservative amino acid substitutions are well known in the art.

Human DDD sequence from protein kinase A
(SEQ ID NO: 1)
SHIQIPPGLTELLQGYTVEVLRQQPPDLVEFAVEYFTRLREARA (SEQ ID NO: 5)
XXIXIXXXLXXLLXXYXVXVLXXXXXXLVXFXVXYFXXLXXXXX Alto et al. (2003) performed a bioinformatic analysis of the AD sequence of various AKAP proteins to design an RII selective AD sequence called AKAP-IS (SEQ ID NO:3), with a binding constant for DDD of 0.4 nM. The AKAP-IS sequence was designed as a peptide antagonist of AKAP binding to PKA. Residues in the AKAP-IS sequence where substitutions tended to decrease binding to DDD are underlined in SEQ ID NO:3. Therefore, the skilled artisan will realize that variants which may function for DNL constructs are indicated by SEQ ID NO:6, where "X" is a conservative amino acid substitution.

```
AKAP-IS sequence
                                        (SEQ ID NO: 3)
QIEYLAKQIVDNAIQQA

                                        (SEQ ID NO: 6)
XXXXXAXXIVXXAIXXX
```

Similarly, Gold (2006) utilized crystallography and peptide screening to develop a SuperAKAP-IS sequence (SEQ ID NO:7), exhibiting a five order of magnitude higher selectivity for the RII isoform of PKA compared with the R1 isoform. Underlined residues indicate the positions of amino acid substitutions, relative to the AKAP-IS sequence, that increased binding to the DDD moiety of RIIα. In this sequence, the N-terminal Q residue is numbered as residue number 4 and the C-terminal A residue is residue number 20. Residues where substitutions could be made to affect the affinity for RIIα were residues 8, 11, 15, 16, 18, 19 and 20 (Gold et al., 2006). It is contemplated that in certain alternative embodiments, the SuperAKAP-IS sequence may be substituted for the AKAP-IS AD moiety sequence to prepare anti-HLA-DR MAb DNL constructs. Other alternative sequences that might be substituted for the AKAP-IS AD sequence are shown in SEQ ID NO:8-10. Substitutions relative to the AKAP-IS sequence are underlined. It is anticipated that, as with the AKAP-IS sequence shown in SEQ ID NO:3, the AD moiety may also include the additional N-terminal residues cysteine and glycine and C-terminal residues glycine and cysteine, as shown in SEQ ID NO:4.

```
SuperAKAP-IS
                                        (SEQ ID NO: 7)
QIEYVAKQIVDYAIHQA

Alternative AKAP sequences
                                        (SEQ ID NO: 8)
QIEYKAKQIVDHAIHQA

                                        (SEQ ID NO: 9)
QIEYHAKQIVDHAIHQA

                                        (SEQ ID NO: 10)
QIEYVAKQIVDHAIHQA
```

Stokka et al. (2006) also developed peptide competitors of AKAP binding to PKA, shown in SEQ ID NO:11-13. The peptide antagonists were designated as Ht31 (SEQ ID NO:11), RIAD (SEQ ID NO:12) and PV-38 (SEQ ID NO:13). The Ht-31 peptide exhibited a greater affinity for the R11 isoform of PKA, while the RIAD and PV-38 showed higher affinity for RI.

```
Ht31
                                        (SEQ ID NO: 11)
DLIEEAASRIVDAVIEQVKAAGAY

RIAD
                                        (SEQ ID NO: 12)
LEQYANQLADQIIKEATE

PV-38
                                        (SEQ ID NO: 13)
FEELAWKIAKMIWSDVFQQC
```

Hundsrucker et al. (2006) developed still other peptide competitors for AKAP binding to PKA, with a binding constant as low as 0.4 nM to the DDD of the RII form of PKA. The sequences of various AKAP antagonistic peptides is provided in Table 1 of Hundsrucker et al. (incorporated herein by reference). Residues that were highly conserved among the AD domains of different AKAP proteins are indicated below by underlining with reference to the AKAP IS sequence (SEQ ID NO:3). The residues are the same as observed by Alto et al. (2003), with the addition of the C-terminal alanine residue. (See FIG. 4 of Hundsrucker et al. (2006), incorporated herein by reference.) The sequences of peptide antagonists with particularly high affinities for the RII DDD sequence are shown in SEQ ID NO:14-16.

```
AKAP-IS
                                        (SEQ ID NO: 3)
QIEYLAKQIVDNAIQQA

AKAP7δ-wt-pep
                                        (SEQ ID NO: 14)
PEDAELVRLSKRLVENAVLKAVQQY

AKAP7δ-L304T-pep
                                        (SEQ ID NO: 15)
PEDAELVRTSKRLVENAVLKAVQQY

AKAP7δ-L308D-pep
                                        (SEQ ID NO: 16)
PEDAELVRLSKRDVENAVLKAVQQY
```

Carr et al. (2001) examined the degree of sequence homology between different AKAP-binding DDD sequences from human and non-human proteins and identified residues in the DDD sequences that appeared to be the most highly conserved among different DDD moieties. These are indicated below by underlining with reference to the human PKA RIIα DDD sequence of SEQ ID NO:1. Residues that were particularly conserved are further indicated by italics. The residues overlap with, but are not identical to those suggested by Kinderman et al. (2006) to be important for binding to AKAP proteins. Thus, a potential DDD sequence is indicated in SEQ ID NO:17, wherein "X" represents a conservative amino acid substitution.

```
                                        (SEQ ID NO: 1)
SHIQIPPGLTELLQGYTVEVLRQQPPDLVEFAVEYFTRLREARA

                                        (SEQ ID NO: 17)
XHIXIPXGLXELLQGYTXEVLRXQPXDLVEFAXXYFXXLXEXRX
```

The skilled artisan will realize that in general, those amino acid residues that are highly conserved in the DDD and AD sequences from different proteins are ones that it may be preferred to remain constant in making amino acid substitutions, while residues that are less highly conserved may be more easily varied to produce sequence variants of the AD and/or DDD sequences described herein.

In addition to sequence variants of the DDD and/or AD moieties, in certain embodiments it may be preferred to introduce sequence variations in the antibody moiety or the linker peptide sequence joining the antibody with the AD sequence. In one illustrative example, three possible variants of fusion protein sequences, are shown in SEQ ID NO:18-20.

```
(L)
                                        (SEQ ID NO: 18)
QKSLSLSPGLGSGGGGSGGCG

(A)
                                        (SEQ ID NO: 19)
QKSLSLSPGAGSGGGGSGGCG

(-)
                                        (SEQ ID NO: 20)
QKSLSLSPGGSGGGGSGGCG
```

Amino Acid Substitutions

In certain embodiments, the disclosed methods and compositions may involve production and use of proteins or peptides with one or more substituted amino acid residues. As discussed above, methods for making monoclonal antibodies against virtually any target antigen are well known in the art. Typically, these result in production of murine antibodies against a target antigen. As is well known in the art, the antigen-binding specificity of murine monoclonal antibodies is determined largely by the hypervariable complementarity determining region (CDR) sequences. Murine antibodies generally comprise 6 CDR sequences, 3 on the antibody light chain and 3 on the heavy chain. As described in detail above, chimeric, humanized or human versions of murine antibodies may be constructed by techniques such as CDR grafting, where the murine CDR sequences are inserted into, for example, human antibody framework and constant region sequences, or by attaching the entire murine variable region sequences to human antibody constant region sequences. In alternative embodiments, the variable region sequences of an antibody may be constructed, for example, by chemical synthesis and assembly of oligonucleotides encoding the entire light and heavy chain variable regions of an antibody.

In various embodiments, the structural, physical and/or therapeutic characteristics of native, chimeric, humanized or human antibodies, or AD or DDD sequences may be optimized by replacing one or more amino acid residues. For example, it is well known in the art that the functional characteristics of humanized antibodies may be improved by substituting a limited number of human framework region (FR) amino acids with the corresponding FR amino acids of the parent murine antibody. This is particularly true when the framework region amino acid residues are in close proximity to the CDR residues.

In other cases, the therapeutic properties of an antibody, such as binding affinity for the target antigen, the dissociation- or off-rate of the antibody from its target antigen, or even the effectiveness of induction of CDC (complement-dependent cytotoxicity) or ADCC (antibody dependent cellular cytotoxicity) by the antibody, may be optimized by a limited number of amino acid substitutions.

In alternative embodiments, the DDD and/or AD sequences used to make the anti-HLA-DR DNL constructs may be further optimized, for example to increase the DDD-AD binding affinity. Potential sequence variations in DDD or AD sequences are discussed above.

The skilled artisan will be aware that, in general, amino acid substitutions typically involve the replacement of an amino acid with another amino acid of relatively similar properties (i.e., conservative amino acid substitutions). The properties of the various amino acids and effect of amino acid substitution on protein structure and function have been the subject of extensive study and knowledge in the art.

For example, the hydropathic index of amino acids may be considered (Kyte & Doolittle, 1982, J. Mol. Biol., 157:105-132). The relative hydropathic character of the amino acid contributes to the secondary structure of the resultant protein, which in turn defines the interaction of the protein with other molecules. Each amino acid has been assigned a hydropathic index on the basis of its hydrophobicity and charge characteristics (Kyte & Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). In making conservative substitutions, the use of amino acids whose hydropathic indices are within ±2 is preferred, within ±1 are more preferred, and within ±0.5 are even more preferred.

Amino acid substitution may also take into account the hydrophilicity of the amino acid residue (e.g., U.S. Pat. No. 4,554,101). Hydrophilicity values have been assigned to amino acid residues: arginine (+3.0); lysine (+3.0); aspartate (+3.0); glutamate (+3.0); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). Replacement of amino acids with others of similar hydrophilicity is preferred.

Other considerations include the size of the amino acid side chain. For example, it would generally not be preferred to replace an amino acid with a compact side chain, such as glycine or serine, with an amino acid with a bulky side chain, e.g., tryptophan or tyrosine. The effect of various amino acid residues on protein secondary structure is also a consideration. Through empirical study, the effect of different amino acid residues on the tendency of protein domains to adopt an alpha-helical, beta-sheet or reverse turn secondary structure has been determined and is known in the art (see, e.g., Chou & Fasman, 1974, Biochemistry, 13:222-245; 1978, Ann. Rev. Biochem., 47: 251-276; 1979, Biophys. J., 26:367-384).

Based on such considerations and extensive empirical study, tables of conservative amino acid substitutions have been constructed and are known in the art. For example: arginine and lysine; glutamate and aspartate; serine and threonine; glutamine and asparagine; and valine, leucine and isoleucine. Alternatively: Ala (A) leu, ile, val; Arg (R) gln, asn, lys; Asn (N) his, asp, lys, arg, gln; Asp (D) asn, glu; Cys (C) ala, ser; Gln (O) glu, asn; Glu (E) gln, asp; Gly (G) ala; His (H) asn, gln, lys, arg; Ile (I) val, met, ala, phe, leu; Leu (L) val, met, ala, phe, ile; Lys (K) gln, asn, arg; Met (M) phe, ile, leu; Phe (F) leu, val, ile, ala, tyr; Pro (P) ala; Ser (S), thr; Thr (T) ser; Trp (W) phe, tyr; Tyr (Y) trp, phe, thr, ser; Val (V) ile, leu, met, phe, ala.

Other considerations for amino acid substitutions include whether or not the residue is located in the interior of a protein or is solvent exposed. For interior residues, conservative substitutions would include: Asp and Asn; Ser and Thr; Ser and Ala; Thr and Ala; Ala and Gly; Ile and Val; Val and Leu; Leu and Ile; Leu and Met; Phe and Tyr; Tyr and Trp. (See, e.g., PROWL website at rockefeller.edu) For solvent exposed residues, conservative substitutions would include: Asp and Asn; Asp and Glu; Glu and Gln; Glu and Ala; Gly and Asn; Ala and Pro; Ala and Gly; Ala and Ser; Ala and Lys; Ser and Thr; Lys and Arg; Val and Leu; Leu and Ile; Ile and Val; Phe and Tyr. (Id.) Various matrices have been constructed to assist in selection of amino acid substitutions, such as the PAM250 scoring matrix, Dayhoff matrix, Grantham matrix, McLachlan matrix, Doolittle matrix, Henikoff matrix, Miyata matrix, Fitch matrix, Jones matrix, Rao matrix, Levin matrix and Risler matrix (Idem.)

In determining amino acid substitutions, one may also consider the existence of intermolecular or intramolecular bonds, such as formation of ionic bonds (salt bridges) between positively charged residues (e.g., His, Arg, Lys) and negatively charged residues (e.g., Asp, Glu) or disulfide bonds between nearby cysteine residues.

Methods of substituting any amino acid for any other amino acid in an encoded protein sequence are well known and a matter of routine experimentation for the skilled artisan, for example by the technique of site-directed mutagenesis or by synthesis and assembly of oligonucleotides encoding an amino acid substitution and splicing into an expression vector construct.

EXAMPLES

Example 1

Construction of a Humanized L243 Antibody

Molecular Cloning of L243$V_K$ and $V_H$ Genes

The hybridoma cell clone producing the mAb mL243 (ATCC HB55) was cultured in HSFM medium (Life Technologies, Inc) supplemented with 10% FBS (Hyclone). The genes encoding the VK (VK1BACK/CK3') and VH (VH1BACK/VH1FOR) of mL243 were cloned by RT-PCR and the sequences were determined by DNA sequencing. Multiple independent clones were sequenced to eliminate possible errors resulting from the PCR reaction.

Sequence Design of hL243 V Genes

Searching the human $V_K$ and $V_H$ sequences in the Kabat database, the FRs of mL243 $V_K$ and $V_H$ were found to exhibit the highest degree of sequence homology to human REI $V_K$ and RF-TS3 $V_H$, respectively. One exception is the FR4 of mL243 $V_H$, which showed the highest sequence homology with that of NEWM $V_H$. Therefore, the human REI framework sequences were used as the scaffold for grafting the CDRs of mL243VK, and a combination of RF-TS3 and NEWM framework sequences were used for hL243 $V_H$. In fact, hL243 $V_H$ has the same human $V_H$ frameworks as that of another humanized Ab, hRS7 (Govindan et al, Breast Cancer Res Treat 84,173-182, 2004). There are a number of amino acid changes in each chain outside of the CDR regions when compared to the starting human antibody frameworks. Several amino acid residues in murine FRs that flank the putative CDRs were maintained in the reshaped hL243 Fv based on the guideline previously established (Qu et al, Clin Cancer Res (1999) 5 3095s-3100s). These residues are R37, K39, V48, F49, and G100 of mL243$V_k$ and F27, K38, K46, A68, and F91 of mL243$V_H$ (FIG. 3 and FIG. 4 respectively). Also see SEQ ID NO:3 and SEQ ID NO:4 respectively for the sequences of hL243 $V_L$ and hL243 $V_H$ respectively.

Construction ofhL243 V Sequences

A modified strategy as described by Leung et al. (Mol Immunol (1995) 32:1413-1427) was used to construct the designed $V_K$ and $V_H$ genes for hL243, using a combination of long oligonucleotide syntheses and PCR. For the construction of the hL243 $V_H$ domain, two long oligonucleotides, hL243VHA (175-mer) and hL243VHB (168-mer) were synthesized on an automated DNA synthesizer (Applied Biosystem).

```
hL243VHA represents nt 23 to 197 of the HL243VH
domain
                                    (SEQ ID NO: 21)
GGTCTGAGTTGAAGAAGCCTGGGGCCTCAGTGAAGGTTTCCTGCAAGGCT

TCTGGATTTACCTTCACAAACTATGGAATGAACTGGGTGAAGCAGGCCCC

TGGACAAGGGCTTAAGTGGATGGGCTGGATAAACACCTACACTAGAGAGC

CAACATATGCTGATGACTTCAAGGG
```

-continued

```
hL243VHB represents the minus strand of the
hL243VH domain complementary to nt 176 to
343.
                                    (SEQ ID NO: 22)
ACCCTTGGCCCCAGTAGTCAAAACCCGTAGGTACAACCGCAGTAATATCT

CTTGCACAGAAATACACGGCAGTGTCGTCAGCCTTTAGGCTGCTGATCTG

GAGATATGCCGTGCTGACAGAGGTGTCCAAGGAGAAGGCAAACCGTCCCT

TGAAGTCATC AGCATATG
```

The 3'-terminal sequences (22 nt residues) of hL243VHA and B are complementary to each other, as underlined in the above sequences. The 3'-ends of hL243VHA and B anneal to form a short double stranded DNA flanked by the rest of the long oligonucleotides. Each annealed end serves as a primer for the replication of the single stranded DNA in a PCR reaction, resulting in a double strand DNA composed of the nt 23 to 343 of hL243VH. This DNA was further amplified in the presence of a short oligonucleotide primer pair, hRS7VHBACK and hL243VHFOR, to form the full-length hL243VH. Because of the sequence identity between hRS7VH and hL243VH in this region, hRS7VHBACK, previously designed and used for hRS7 Ab, was used here.

```
hRS7VHBACK
                                    (SEQ ID NO: 23)
GTGGTGCTGCAGCAATCTGGGTCTGAGTTGAAGAAGCC

hL243VHFOR
                                    (SEQ ID NO: 24)
TGAGGAGACGGTGACCAGGGACCCTTGGCCCCAGTAGT
```

A minimum amount of hL243VHA and B (determined empirically) was amplified in the presence of 10 μl of 10× PCR Buffer (500 mM KCl, 100 mM TrisHCL buffer, pH 8.3, 15 mM $MgCl_2$), 2 μmol of hRS7VHBACK and hL243VHFOR, and 2.5 units of Taq DNA polymerase (Perkin Elmer Cetus, Norwalk, Conn.). This reaction mixture was subjected to 3 cycle of PCR reaction consisting of denaturation at 94° C. for 1 minute, annealing at 45° C. for 1 minute, and polymerization at 72° C. for 15 minutes, and followed by 27 cycles of PCR reaction consisting of denaturation at 94° C. for 1 minute, annealing at 55° C. for 1 minute, and polymerization at 72° C. for 1 minute. Double-stranded PCR-amplified product for hL243VH was gel-purified, restriction-digested with PstI and BstEII and cloned into the complementary PstI/BstEII sites of the heavy chain staging vector, VHpBS4.

For constructing the full length DNA of the humanized $V_K$ sequence, hL243 VKA (155-mer) and hL243VKB (155-mer) were synthesized as described above. hL243VKA and B were amplified by two short oligonucleotides hlmmu31VKBACK and hlmmu31VKFOR as described above. hImmuS 1 VKB ACK and hlmmuS1 VKFOR were designed and used previously for a humanized anti-AFP Ab (Qu et al, Clin Cancer Res (1999) δ 395-31).

```
hL243VKA represents nt 21 to 175 of the hL243VD
domain
                                    (SEQ ID NO: 25)
TCCATCATCTCTGAGCGCATCTGTTGGAGATAGGGTCACTATCACTTGTCG

AGCAAGTGAGAATATTTACAGTAATTTAGCATGGTATCGTCAGAAACCAGG
```

-continued

```
GAAAGCACCTAAACTGCTGGTCTTTGCTGCATCAAACTTAGCAGATGGTGT

GC
```

hL243VKB represents the minus strand of the hL243VK domain complementary to nt 154 to 312

(SEQ ID NO: 26)

```
CAGCTTGGTCCCTCCACCGAACGCCCACGGAGTAGTCCAAAAATGTTGACA

ATAATATGTTGCAATGTCTTCTGGTTGAAGAGAGCTGATGGTGAAAGTATA

ATCTGTCCCAGATCCGCTGCCAGAGAATCGCGAAGGCACACCATCTGC TA

AGTTTGA
```

hImmu31VKBACK (SEQ ID NO: 27)

```
GACATTCAGCTGACCCAGTCTCCATCATCTCTGAGCGC
```

hImmu31VKFOR (SEQ ID NO: 28)

```
CCGGCAGATCTGCAGCTTGGTCCCTCCACCG
```

Gel-purified PCR products for hL243VK were restriction-digested with PvuII and BglHI and cloned into the complementary PvuI/BclI sites of the light chain staging vector, VKpBR2. The final expression vector hL243pdHL2 was constructed by sequentially subcloning the XbaI-BamHI and XhoI/NotI fragments of hL243$V_K$ and $V_H$, respectively, into pdHL2 as described above.

Construction of the Expression Vectors for hL243 Antibodies

A final expression vector hL243pdHL2 was constructed by sequentially subcloning the XbaI-BamHI and XhoI/NotI fragments of hL243$V_K$ and $V_H$, respectively, into pdHL2 as described previously (Losman et al *Cancer,* 80:266, 1997). The expression vector pdHL2, as described by Gilles et at (*J Immunol Methods* 125:191, 1989), contains the genomic sequence of the human γ1 chain, therefore, the hL243 is an IgG1/K isotype.

To construct the expression vector for hL243 of other isotypes, such as IgG4/K, the genomic sequence of human γ1 chain was replaced with that of γ4 chain, which was obtained by PCR amplification. The template used was the genomic DNA extracted from ATCC CRL-11397 cell and the primer pair was P-SacII CCGCGGTCACATGGCACCACCTCTCTTGCAGCTTCCACCAAGGGCCC (SEQ ID NO:29) and P-EagI CCGGCCGTCGCACTCATTTACCCAGAGACAGGG (SEQ ID NO:30). The amplified PCR product was cloned into TOPO-TA sequencing vector (Invitrogen) and the sequence was confirmed by DNA sequencing.

A point mutation, Ser241Pro (based on Kabat numbering) was introduced into the hinge region of the γ4 sequence to avoid formation of half-molecules when the IgG4 Ab is expressed in mammalian cell cultures (Schuurman et al, *Mol Immunol* 38:1, 2001). The human γ4 hinge region sequence between PstI and StuI restriction sites (56 bp) was replaced with a synthetic DNA fragment with substitution of the TCA codon for Ser241 to CCG for Pro. The human γ1 genomic sequence in hL243pdHL2 was substituted with the mutated γ4 sequence, resulting in the final expression vector, designated as hL243γ4PpdHL2, for the IgG4 isotype hL243.

Transfection and Expression of hL243 Antibodies

Approximately 30 μg of the expression vector for hL243 or hL243γ4P was linearized by digestion with SalI and transfected into Sp2/0-Ag14 cells by electroporation (450V and 25 μF). The transfected cells were plated into 96-well plates for 2 days and then selected for drug-resistance by adding MTX into the medium at a final concentration of 25 pM. MTX-resistant colonies emerged in the wells after 2-3 weeks. Supernatants from colonies surviving selection were screened for human Ab secretion by ELISA assay. Briefly, 100 ul supernatants were added into the wells of a microtiter plate precoated with GAH-IgG, F(ab')$_2$ fragment-specific Ab and incubated for 1 h at room temperature. Unbound proteins were removed by washing three times with wash buffer (PBS containing 5% polysorbate 2). HRP-conjugated GAH-IgG, Fc fragment-specific Ab was added to the wells. Following an incubation of 1 h, the plate was washed. The bound HRP-conjugated Ab was revealed by reading $A_{490}$ nm after the addition of a substrate solution containing 4 mM OPD and 0.04% $H_2O_2$. Positive cell clones were expanded and hL243 and hL243γ4P were purified from cell culture supernatant by affinity chromatography on a Protein A column.

The Ag-Binding Specificity of hL243

Ag-binding activity and specificity of HL243 was shown by a cell surface binding assay. Raji cells were incubated in PBS/BSA (1%) containing saturate concentration of purified hL243 (2 μg/ml) for 1 h at 4° C. After washing, cell surface-bound hL243 was detected by incubating the Raji cells in the buffer containing a PE-conjugated $2^{nd}$ antibody (goat anti-human IgG, Fc fragment specific) and counting in a Guave PCA system (Guava Technologies, Inc, Hayword, Calif.). As shown in FIG. 5, hL243 bound to an antigen on Raji cells recognized by mL243 because the binding is specifically blocked by preincubation of the cells with mL243, indicating the Ag-binding specificity of mL243 is preserved in the humanized version.

The Ag-Binding Activity of hL243γ4P

A competition cell-binding assay was carried out to assess the immunoreactivity of hL243γ4P relative to the parent mL243. A constant amount of $^{125}$I-labeled murine L243 or hL243γ4P (100,000 cpm, ~10 μCi/μg) was incubated with human lymphoma cells (Raji, Daudi or Ramos) in the presence of varying concentrations (0.2-700 nM) of purified hL243γ4P or murine L243 at 4° C. for 1-2 h. Unbound Abs were removed by washing the cells in PBS. The radioactivity associated with cells was determined after washing. As shown in FIG. 6, murine L243 and hL243γ4P mAbs competed with each other for the binding to the cell surface antigen, indicating they recognize same antigenic determinant. hL243γ4P showed an apparent ~2-fold stronger binding avidity than mL243 because it competed better than mL243 ($EC_{50}$ of ~7 vs ~16.5 nM).

Figure 7:
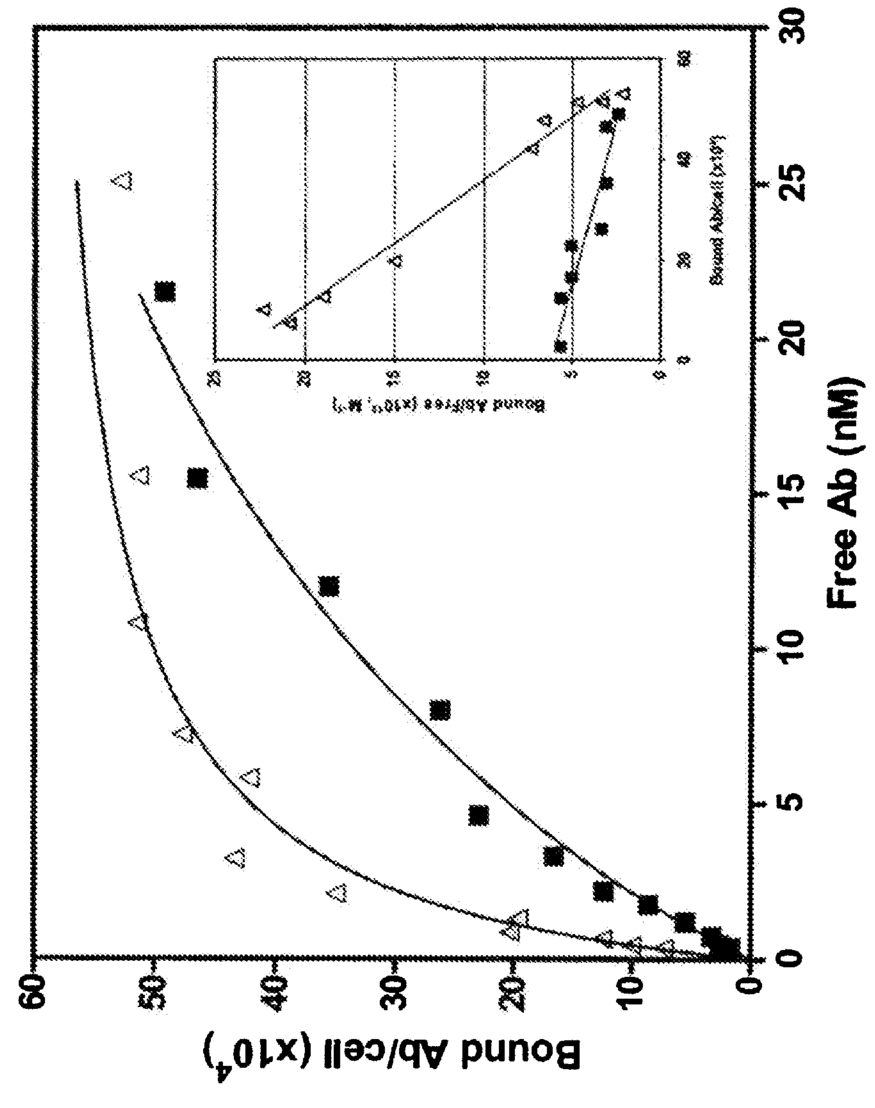
FIG. 7 illustrates exemplary Ag-binding affinities of hL243γ4P and mL243 determinated by direct cell surface saturation binding and Scachard plot analysis. Varying concentrations of $^{125}$I-labeled mL234 (solid square) or hL243γ4P (open triangle) were incubated with $2\times10^5$ Daudi human lymphoma cells at 4° C. for 2 h, and unbound radioactivity was removed from cell suspensions by washing. The cell-associated radioactivity was counted, specific binding of radiolabeled antibody to the cell surface antigen calculated, and Scatchard plot analysis was then applied to determine the maximum number of binding sites per cell and the apparent antigen-binding affinity constant. The maximum binding of mL234 or hL243γ4P to Daudi cell surface was $6\times10^6$ molecules/cell. The dissociation constants determined for mL234 or hL243γ4P were 14 and 2.6 nM, respectively.

The antigen-binding affinity constant of hL243γ4P was determined by direct cell surface binding assay of the radiolabeled antibodies and Scatchard plot analysis. To measure specific cell surface antigen binding, two sets of cells were prepared and used in the binding assay to estimate the non-specific and total binding of radioactivities, respectively. The cells for non-specific binding were pre-incubated with excess amount of unlabeled Ab to block all surface antigen sites prior to adding the radiolabeled antibody, while those for total binding were pre-incubated in PBS. After pre-incubation, varying amounts of either $^{125}$I-hL243γ4P or $^{125}$I-mL243 were added and incubated with $2\times10^5$ human lymphoma cells (Raji, Daudi or Ramos) at 4° C. for 2 h and unbound antibodies were removed by washing. The cell-associated radioactivity was counted. The specific cell surface binding of the radiolabeled antibody at a given concentration of radiolabeled antibody was calculated as: the counts of total binding minus the counts of non-specific binding. Scatchard plot analysis was then performed to determine the maximum number of hL243γ4P and mL243 binding sites per cell and the apparent dissociation constants of the equilibrium binding. As shown in FIG. 7, the maximum binding of hL243γ4P and mL243 to Daudi cells was virtually same, ~$6\times10^5$ molecules/cell, indicating they bound to the same Ag. The apparent dissociation constant values for hL243γ4P and mL243 were calculated to be 2.6 and 14 nM, respectively. Similar results were obtained with Raji and Ramos cells (data not shown).

Example 2 hL243γ4P Functional Studies

In vitro cell-based studies were conducted to determine whether hL243γ4P had retained its antiproliferative effect and whether effector cell and complement binding functions have been abrogated. This study indicated that the antiproliferative effect had been maintained, while effector cell and complement binding functions had been abrogated.

Effector Cell Assay

The goal of replacing the Fc region of hL243 with an IgG4 isotype Fc region was to abrogate effector cell functions through Fcγ-receptor. Complement-binding CDC and ADCC assays were performed to assess these functions by hL243y4P.

CDC

Figure 8:
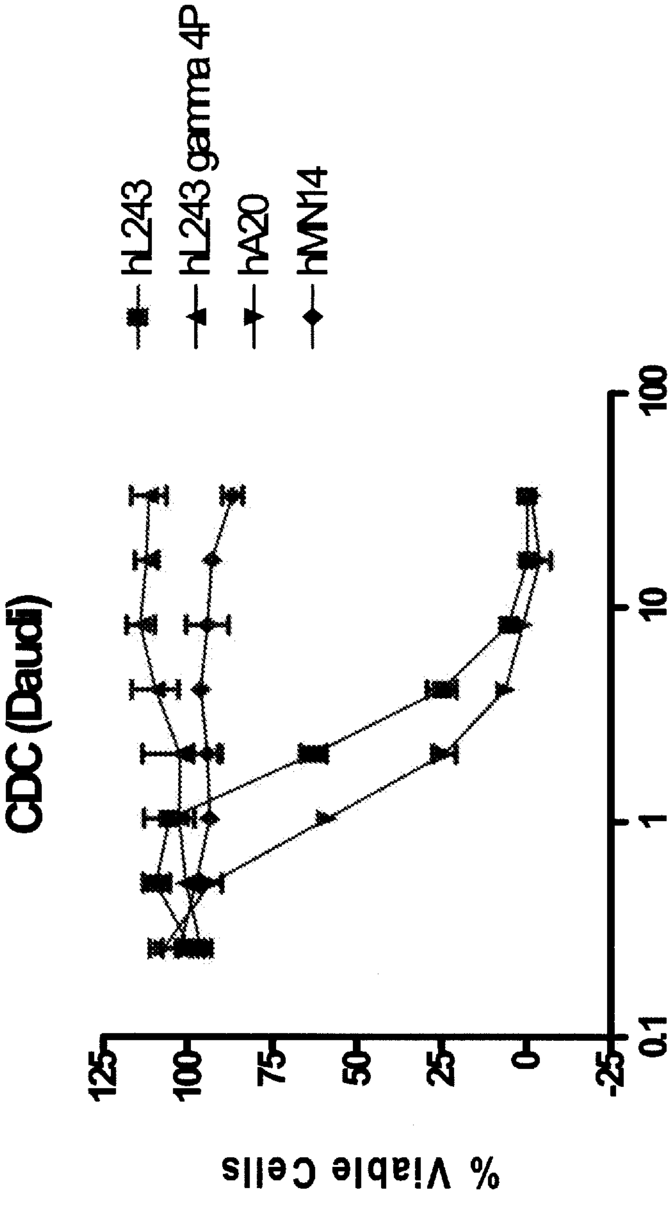
FIG. 8 illustrates that hL243 is effective in killing target cells in the presence of human serum complement. Daudi cells were incubated with hL243, hL243γ4P, hA20 (a positive control), and hMN-14 (a negative control) in the presence of human serum complement. hL243γ4P was shown not to produce any complement-induced cytotoxicity.
Figure 15:
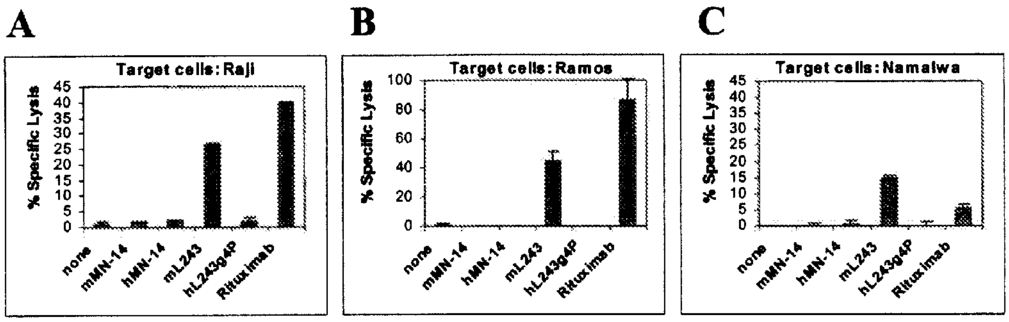
FIG. 15 illustrates CDC assays in (A) Raji, (B) Ramos and (C) Namalwa cell lines when exposed to various antibodies disclosed herein.

Daudi cells were incubated with serial dilutions of the antibodies hL243, hL243γ4P, hA20 (as another positive control) and hMN14 (negative control) in the presence of human complement for 2 h. This was followed by the addition of resazurin to assess cell viability. Both untreated and maximum lysis controls were included. Fluorescence readings were obtained 5 hours after resazurin addition. The fluorescence level obtained is directly correlated to the amount of viable cells. Percent viable cells was calculated by the formula (Test−maximum lysis)/(untreated control−maximum lysis)×100. The results indicated that hL243γ4P does not produce any complement-mediated cytotoxic effect on cells compared to hL243 ($EC_5$=2.6 nM) and hA2 ($EC_5$=0.66 nM). See FIG. 8 and FIG. 15.

ADCC

Figure 9:
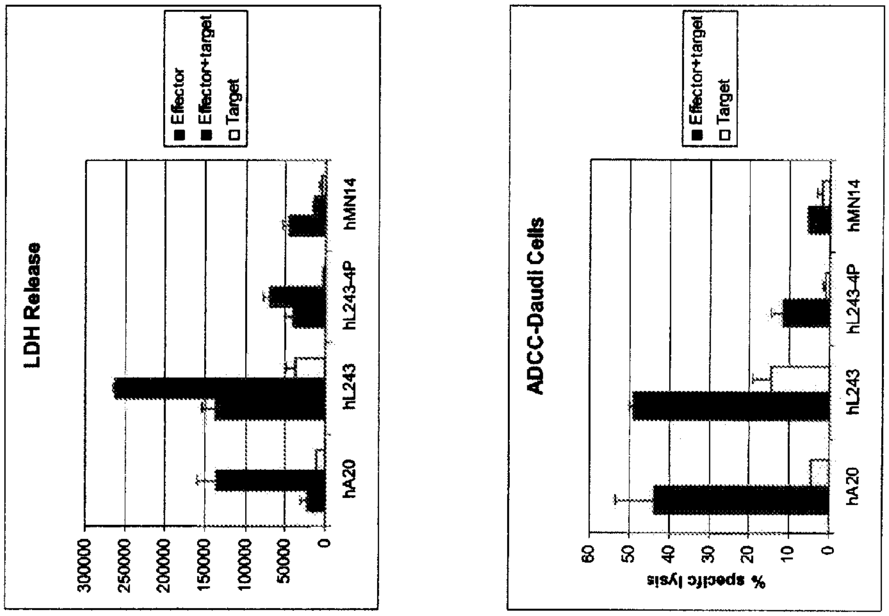
FIG. 9 illustrates LDH release (A) and % cell lysis (B) by ADCC as observed for hL243, hL243γ4P, hA20 (positive control) and hMN-14 (negative control).

Daudi cells were incubated with hA20, hL243, hL243γ4P and hMN-14 at 5 μg/ml. Effector cells were added at a ratio of 5:1. After 4 hours cell lysis was assayed by LDH release (FIG. 9A) and cell lysis (FIG. 9B).

In these results where the effects of antibody alone on effector cells are shown it can be seen that the hL243 induced significant lysis of effector cells while hL243γ4P did not. When the specific lysis figures are corrected for the effect on effector cells, hL243γ4P shows much reduced lysis of target cells compared to hL243 (12% vs 48%).

In Vitro Proliferation Assays

Figure 10:
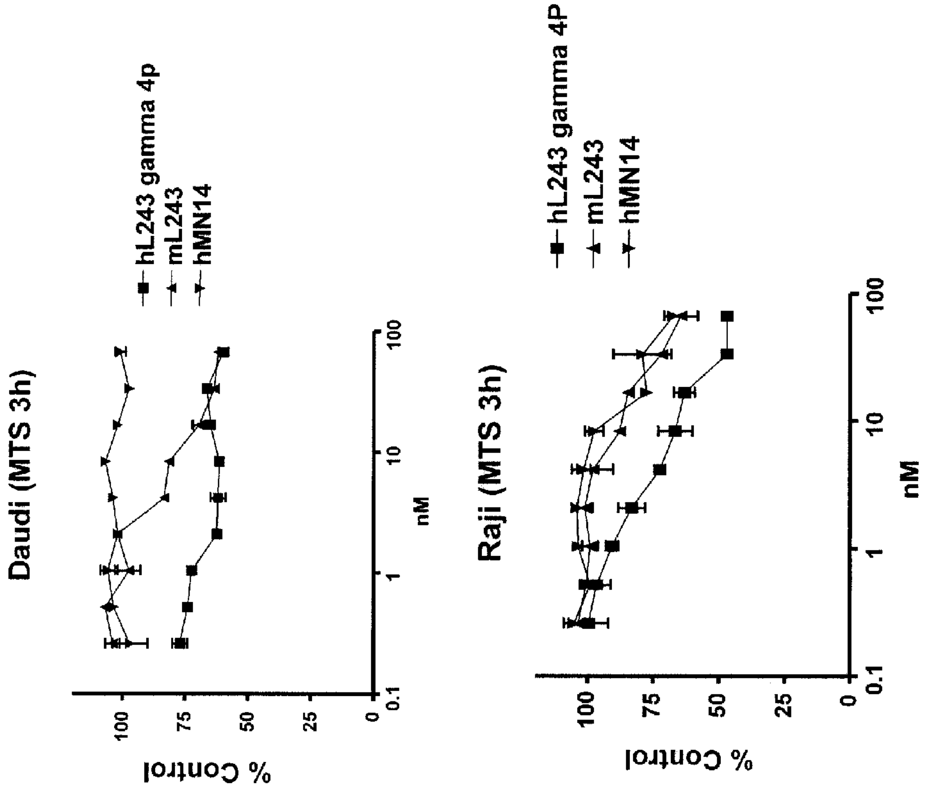
FIG. 10 illustrates exemplary in vitro proliferative assays on (A) Daudi and (B) Raji cell lines at the end of 2 days.
Figure 11:
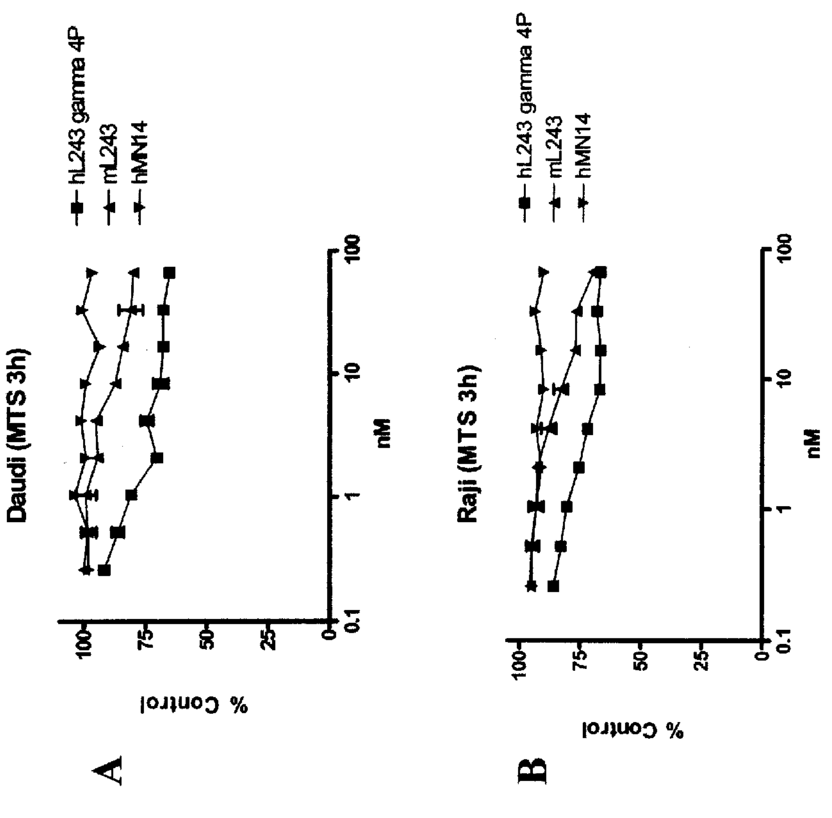
FIG. 11 illustrates exemplary in vitro proliferative assays on (A) Daudi and (B) Raji cell lines at the end of 3 days.

A multiplex colorimetric assays utilizing both MTS bioreduction (for determination of the number of viable cells) and BrdU (for quantification of cell proliferation based on the measurement of BrdU incorporation during DNA synthesis) were performed. Daudi and Raji cells were incubated with serial dilutions of hL243γ4P for 2 and 3 days. mL243 and hMN-14 were used as positive and negative controls respectively. After incubation, BrdU and MTS assays were performed. Results of the MTS assays are shown in FIG. 10 and FIG. 11. BRDU assays gave similar results (not shown). These results indicate hL243γ4P inhibits proliferation of Raji and Daudi cell lines. However in similar experiments in the EBV negative cell line Ramos, inhibition of proliferation was only observed in the presence of a crosslinking anti Fc $(Fab)_2$.

Example 3

Comparison of In Vivo Efficacy of hL243γ4P and mL243 (IgG2a) in a Xenograft Model of Human Non-Hodgkin's Lymphoma A therapeutic study was performed to compare the in vivo efficacy of humanized L243-IgG4 and murine L243-IgG2a monoclonal antibody isotypes, in a xenograft model of human non-Hodgkin's lymphoma (Raji). Prior in vitro studies have shown that replacing the Fc region of L243-IgG1 with an IgG4 isotype abrogates the effector cell functions of the antibody (ADCC and CDC), while retaining the antiproliferative effects. Prior studies using fully human anti-HLA-DR antibodies engineered as an IgG4 isotype have also been shown to minimize side effects due to Fcγ-mediated effector functions while providing excellent tumoricidal activity in vitro, and in vivo in xenograft models of non-Hodgkins lymphoma and animal models (cynomologus monkeys) with no long-lasting hematological effects. See Nagy et al, Nature Medicine, 8:801 (2002). Thus, this study aimed to determine if hL243-IgG4 could maintain significant antitumor efficacy in a xenograft model. In the absence of sufficient quantity of hL243-IgG1, mL243 IgG2a was used (murine IgG2a is the equivalent of human IgG1 in complement fixation, and effecting ADCC).

Figure 12:
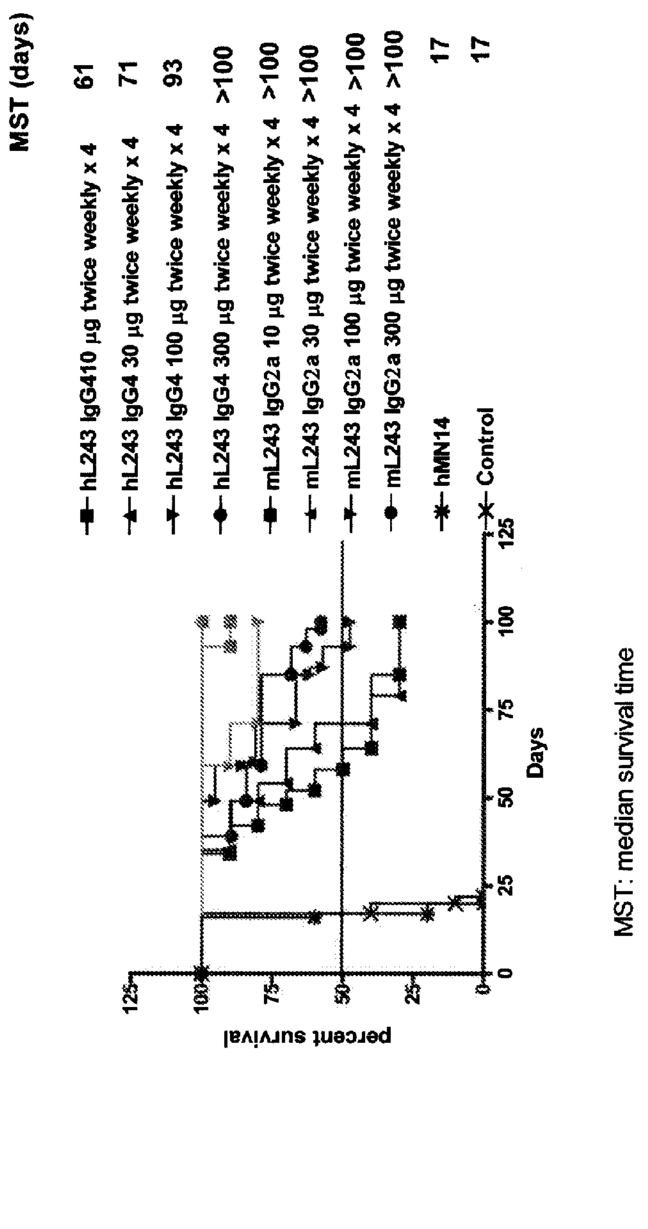
FIG. 12 illustrates exemplary median survival times for tumor-bearing SCID mice injected with hL243γ4P.

SCID mice were injected with 2.5 million Raji cells. Therapy with hL243-IgG4 or mL243-IgG2a was initiated 1 day post tumor cell administration. Both groups of mice injected with saline or with non-specific control antibody, hMN-14, had a median survival time (MST) of 17 days. All the groups of mice treated with either humanized or murine L243 had significantly improved life span compared to mice injected with saline or hMN-14 ($P<0.0001$). Treatment with various doses of hL243 IgG4 resulted in a dose-response relationship, with mice receiving higher doses having better survival times. In the group of animals treated with various doses of mL243 IgG2a, the cure rate was in the range of 80-100%. See FIG. 12.

This study showed the concurrent retention of antitumor efficacy and removal of complement binding activity of the IgG4 construct of L243. Although, this study was performed in mice, significant therapeutic benefits using the aforementioned constructs may be achieved in all mammals suffering from autoimmune diseases, lymphomas, or leukemias. In particular, the aforementioned constructs can effectively be used in (i) domestic animals, especially cats, dogs, and horses, to treat autoimmune diseases and lymphomas/leukemias; and (ii) humans, for the treatment of autoimmune diseases, lymphomas, and leukemias, as well as immune dysregulatory, metabolic, and neurodegenerative diseases involving HLA-DR expression.

Example 4

In Vitro Comparison of hL243 with L243 and Anti-B Cell MAbs in the Treatment of Human and Canine Lymphomas A 0.5 mg sample of hL243 (IgG4 isotype) was tested for reactivity with lymphoma cell lines and a dog B cell lymphoma aspirate in comparison to the murine L243 as well as in comparison to other anti-B cell MAbs. Two functional studies were also done. The ability of the hL243 to induce apoptosis in the dog lymphoma aspirate was determined, and the anti-proliferative activity of the hL243 was tested against Namalwa, a human lymphoma cell line reported to be resistant to rituximab.

The binding of humanized or chimeric MAbs on human B cell lymphomas were measured by flow cytometry using a Fluorescence-Activated Cell Sorter (FACS) in which the following MAbs—hMN-14, hLL1, hLL2, hA20, RITUXAN®, and hL243 were stained with FITC goat anti-human (GAH) IgG Fc. The cell lines chosen were Namalwa (a rituximab resistant human B cell lymphoma cell line), SU-DHL-6 (a human B cell non-Hodgkin's lymphoma), WSU-FSCCL (an EBV-negative low-grade human B cell lymphoma cell line), Raji, Daudi, and Ramos cells. As shown in Table 2, hL243 bound to all the aforementioned cell lines. In particular, hL243 bound to the Namalwa cells that are CD20-unresponsive, showing greater binding than other humanized MAbs. (See Table 1) Furthermore, hL243 demonstrated anti-proliferative activity in the rituximab resistant human B cell lymphoma cell line, Namalwa, as measured by a $^3$H-thymidine uptake assay. The other anti-CD20 antibody, humanized A20 (hA20), developed by Immunomedics, Inc, showed similar results to rituximab, a chimeric anti-CD20 known as RITUXAN®. See Stein et al. (2004) *Clin Cancer Res* 10: 2868-2878.

Figure 14:
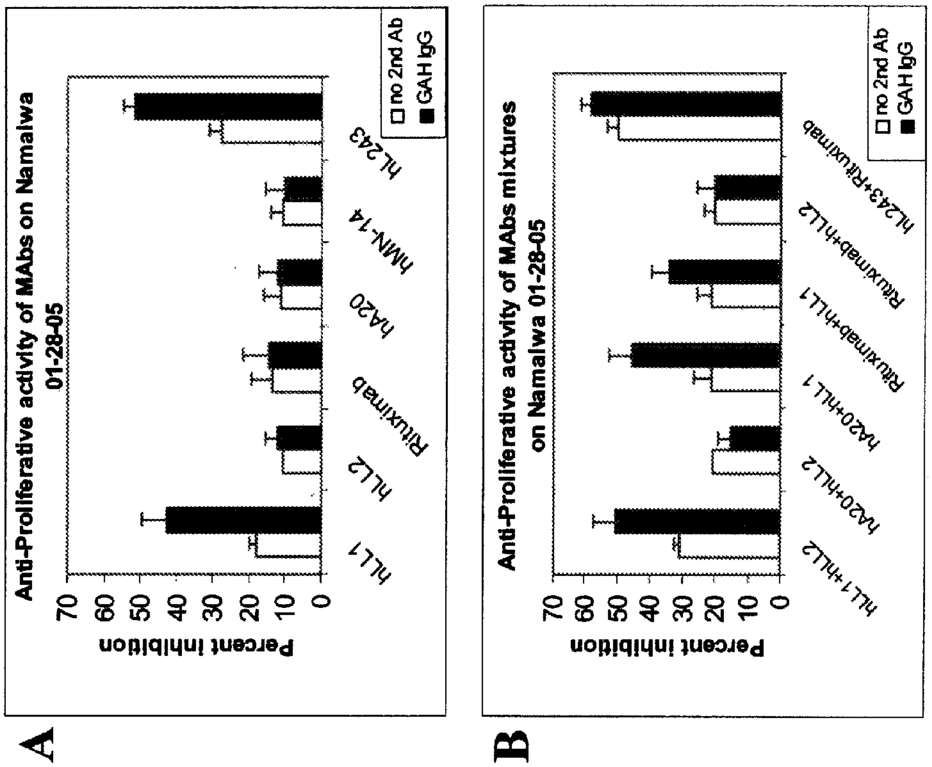
FIG. 14 illustrates anti-proliferative effects of humanized antibodies (hLL1, hLL2, Rituximab, hA2, hMN-14 and hL243 IgG4 isotype), with and without goat anti-human IgG (GAH)) on Namalwa human B cell lymphoma cell line as determined by a $^3$H-thymidine uptake assay with (A) single antibodies or (B) mixtures of antibodies.

As shown in FIG. 14A-B, the hL243 MAb yielded 28% inhibition of proliferation when given alone. This was increased to 51% when hL243 was given in combination with anti-human IgG second antibody. When used in combination with rituximab the activity was increased to a level greater than that of either MAb alone. See FIG. 14-B. Thus, anti-HLA-DR antibodies used in combination with other anti-TAA antibodies may exhibit synergistic effects against lymphoma and other diseases.

Figure 13:
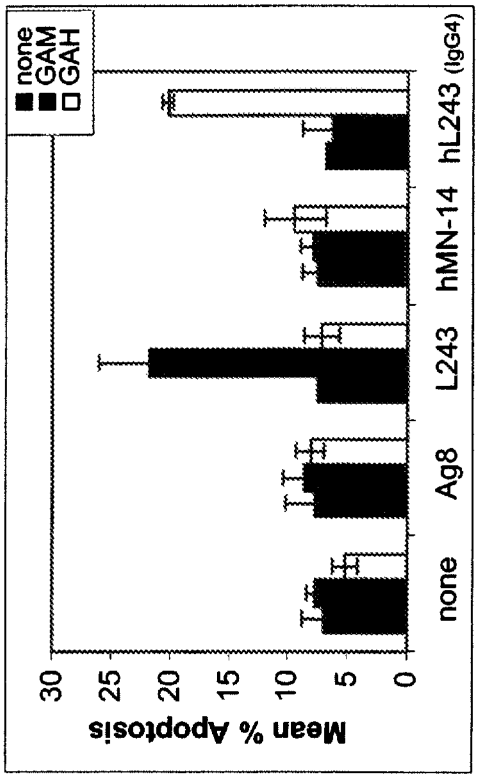
FIG. 13 illustrates comparative induction of apoptosis in dog lymphoma cells (measured as % cells with a sub GO/G1 phase DNA content) caused by L243, hL243 (IgG4 isotype), hMN-14 (humanized MN-14 IgG), and Ag8 (murine myeloma derived mAb). L243 and hL243 caused apoptosis when crosslinked with goat anti-mouse (GAM) and goat-anti human (GAH) antibodies respectively.

The studies also demonstrated that hL243 has a greater binding affinity to the dog lymphoma cells than other humanized MAbs. See Table 3. In addition, hL243 was able to induce apoptosis in the dog lymphoma cells when crosslinked with an anti-human IgG second antibody, measured as % cells with a sub GO/G1 phase DNA content. See FIG. 13.

Example 5 hL243 Antibody Combinations and Their Effects

Methods

Antibodies

The hybridoma cell clone producing the anti-HLA-DR monoclonal antibody, mL243, was obtained from ATCC (ATCC number HB-55). Cells were cultured in HSFM medium (Life Technologies, Inc) supplemented with 10% FBS (Hyclone). The genes encoding the $V_\kappa$ and $V_H$ genes of L243 were cloned by RT-PCR. The humanized L243 (IgG1/κ isotype), hL243γ1, was generated similarly, as described previously (Leung et al., Hybridoma 13:469 (1994); Leung et al., Mol Immunol 32:1413 (1995); Stein et al., Blood 14:375 (2004); Govindan et al., Breast Cancer Res Treat 84:173 (2004)).

The IgG4/κ isotype of hL243, hL243γ4p, can be constructed by replacing the heavy chain constant region coding sequence for the human γ1 chain with that of γ4 chain. A point mutation, Ser241Pro (based on Kabat numbering) was introduced into the hinge region of the γ4 sequence in order to avoid formation of half-molecules when the antibody is expressed and produced in mammalian cell cultures (Schuurman et al., Mol Immunol 38:1 (2001)). Other MAbs used in the studies were rituximab, purchased from IDEC Pharmaceuticals Corp. (San Diego, Calif.), and hMN-14, or labetuzumab (humanized anti-carcinoembryonic antigen IgG1), provided by Immunomedics, Inc. The construction and characterization of hMN-14, used here as a negative isotype control, have been described previously (see, e.g., U.S. Pat. No. 5,874,540).

Cells

Exemplary cell lines were used in several studies. For example, the Burkitt lymphoma lines, Daudi, Raji, and Ramos, were purchased from the American Type Culture Collection (Manassas, Va.). Non-Burkitt lymphoma cell lines were obtained as follows: RL and SU-DHL-6, which contain the chromosomal translocation t(14; 18), were obtained from Dr John Gribben (Dana-Farber Cancer Institute, Boston, Mass.) and Dr Alan Epstein (University of Southern California, Los Angeles, Calif.), respectively. Cell lines SU-DHL-4, SU-DHL-1, and Karpas 422 were provided by Dr Myron Czuczman (Roswell Park Cancer Institute, Buffalo, N.Y.), and WSU-FCCL and DoHH2 cell lines were obtained from Dr Mitchell Smith (Fox Chase Cancer Center, Philadelphia, Pa.). The cells were grown as suspension cultures in DMEM (Life Technologies, Gaithersburg, Md.), supplemented with lo % fetal bovine serum, penicillin (100 U/ml), streptomycin (100 μg/ml), and L-glutamine (2 mM) (complete media).

Flow Cytometric Assays

Immunophenotyping. Indirect immunofluorescence assays were performed with the panel of cell lines described above, using FITC-goat anti-human IgG (Tago, Inc., Burlingame, Calif.) essentially as described previously, and analyzed by flow cytometry using a FACSCaliber (Becton Dickinson, San Jose, Calif.).

Analysis of Apoptosis. Flow cytometric analysis of cellular DNA was performed following propidium iodide staining Cells were placed in 24-well plates ($5\times10^5$ cells/well) and subsequently treated with MAbs (5 μg/ml). Three wells were prepared with each MAb to study the effects of crosslinking with goat anti-mouse or goat anti-human second antibodies. Following a 2-min incubation with the primary MAbs (37° C., 5% $CO_2$), F(ab')$_2$ goat anti-mouse IgG Fcγ-specific second antibody (Jackson Laboratories, West Grove, Pa.) was added to one well from each primary MAb to adjust the second antibody concentration to 20 pg/ml. F(ab')$_2$ goat anti-human IgG Fcγ-specific (Jackson Laboratories) was similarly added to the second well from each primary MAb, and the volume of the third set was equalized by addition of medium. Following a 48-h incubation (37° C., 5% $CO_2$), cells were transferred to test tubes, washed with PBS, and then resuspended in hypotonic propidium iodide solution (50 mg/ml propidium iodide in 0.1% sodium citrate, 0.1% Triton X-100). Samples were analyzed by flow cytometry using a FACSCaliber. Percent apoptotic cells was defined as the percent of cells with DNA staining before G0/G1 peak (hypodiploid).

Antigen Expression of Cultured Lymphoma Cells

Flow cytometry analysis was performed using indirect immunofluorescent staining to show that hL243γ4P binds to a panel of cultured human B cell lymphomas. A comparison to other surface antigens is shown. As seen in Table 4, the hL243γ4P MAb binds to all the tested cell lines. A stronger expression was observed on Daudi and Raji, but the level of fluorescence staining is strong on all the cell lines tested. Binding was compared to that of humanized MAbs against other B cell antigens (CD74, CD22, CD20), the murine-human chimeric anti-CD20 MAb rituximab, and a humanized anti-CEA MAb (negative control). The staining with hL243γ4P was markedly greater than that of CD22 and CD74 on all seven cell lines. CD20 staining was more variable, as shown by reactivity with the humanized (hA20) and chimeric (rituximab) MAbs. The Burkitt's lines, Daudi, Raji, and Ramos, expressed intermediate levels of CD20, whereas the follicular and diffuse large B cell lymphoma lines assessed varied. In comparison to HLA-DR expression measured by hL243γ4P binding, SU-DHL-6 has higher CD20 expression, Namalwa, and WSU-FSCCL lower CD20 expression, and RL approximately equal expression of both antigens.

Effector Cell Assays

Figure 16:
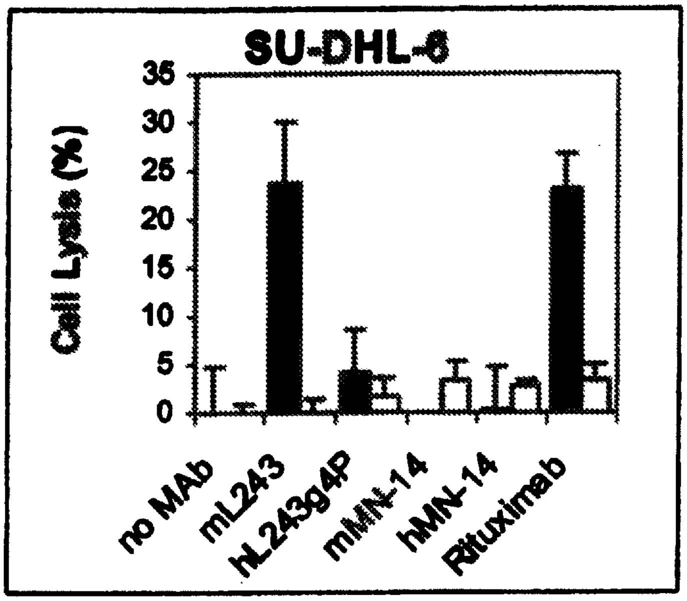
FIG. 16 illustrates ADCC assays and calcein AM release when SU-DHL-6 cells are exposed to various antibodies disclosed herein.

Induction of ADCC was measured in Raji, Daudi, and SU-DHL-6 by calcein AM release. The activity of hL243γ4P was compared to that of the murine L243 and rituximab, as a positive control. As expected, rituximab and the murine L243 induced significantly more cell lysis than the negative controls (no MAb and murine and humanized MN-14) and hL243γ4P did not (FIG. 16).

In Vitro Anti-Proliferative Effects

Figure 17:
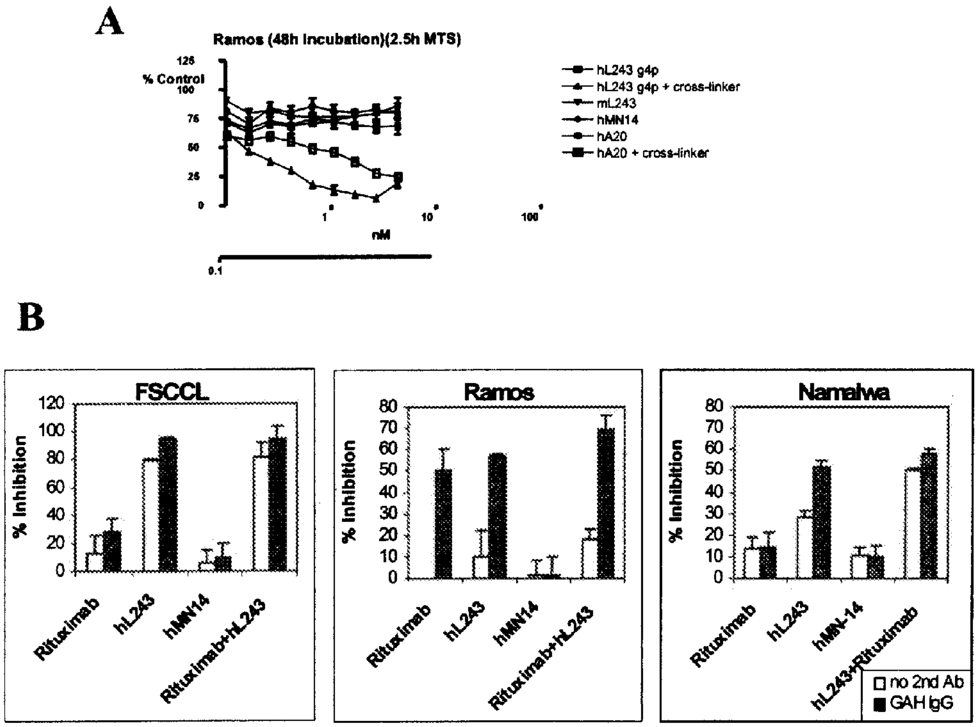
FIG. 17 illustrates anti-proliferative effects of hL243γ4P on several cell lines disclosed herein. (A) MTT studies and (B) $^3$H-thymidine uptake assays. In (B) hL243 refers to the γ4P form of the antibody.

The effect of hL243 on cellular proliferation was assessed using the $^3$H-thymidine uptake assay on Raji, FSCCL, and Namalwa cells (FIG. 17B and Table 5). The effect of hL243γ4P was compared to that of rituximab and to rituximab combined with hL243γ4P, in the presence or absence of a crosslinking anti Fc antibody. In FSCCL, previously shown to be relatively insensitive to rituximab, hL243γ4P yielded significantly greater inhibition of proliferation than rituximab. In Ramos, hL243 and rituximab activity were similar, and the combination was more effective than either alone. The combination may have a synergistic effect. Cross-linking with an anti-human Fc antibody was required for significant anti-proliferative activity to be seen in Ramos. In Namalwa, as with FSCCL, hL243γ4P yielded significantly greater inhibition of proliferation than rituximab and the combination of rituximab and hL243γ4P yielded significantly more inhibition of proliferation than either MAb alone.

Assessment of Apoptosis Induction

The mechanism of hL243 γ4P-induced cell death was evaluated by measuring various markers of apoptosis. These included induction of DNA fragmentation, Annexin V/7-AAD staining, measurement of activated caspase-3, loss of mitochondrial membrane potential and activation of the AKT survival pathway.

Figure 18:
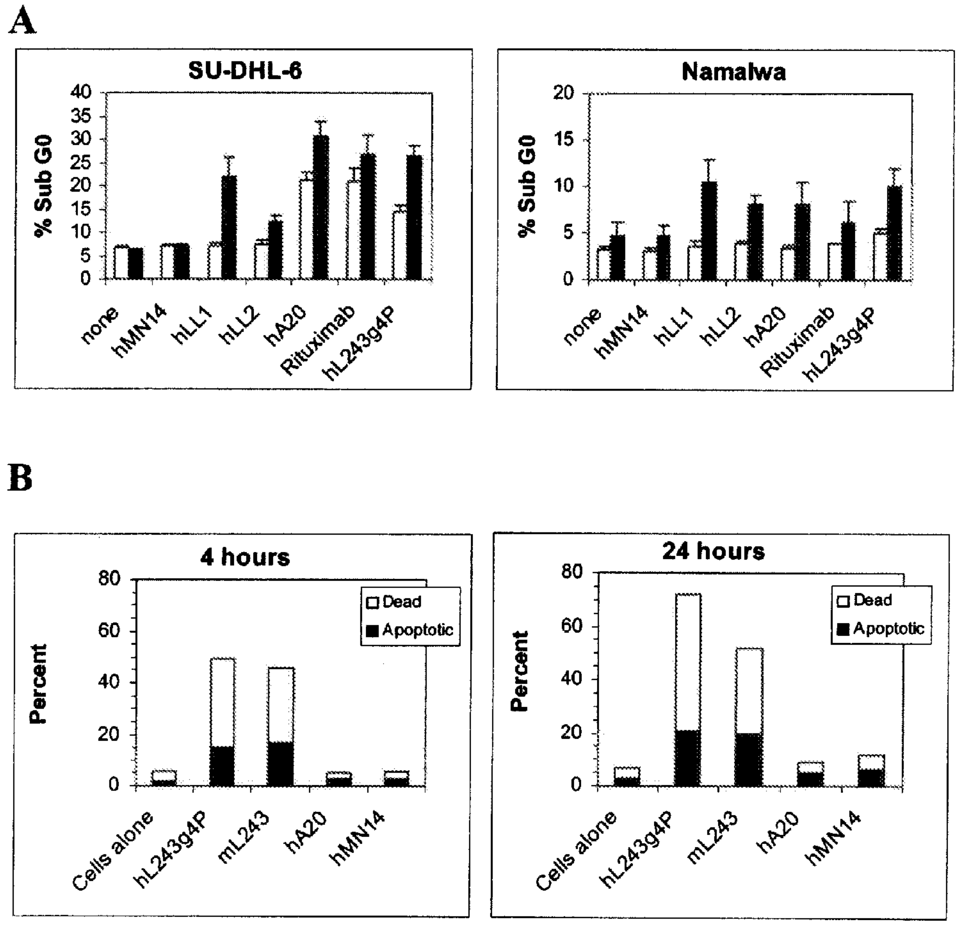
FIG. 18 illustrates induction of apoptosis. Dead cells are represented by clear and apoptotic cells are represented by solid bars. (A) measurement of Sub G DNA in SU-DHL-6 and Namalwa cells. (B) Annexin V/7-ADD at 4 and 24 hours. Cells used had 97% viability prior to treatment.

DNA fragmentation was evaluated by flow cytometry in SU-DHL-6 and Namalwa. Cells were cultured with the MAbs for 48 h with or without a second MAb for crosslinking, followed by DNA staining with propidium iodide. Cells were analyzed by flow cytometry, and positive florescence below the G1 region represents DNA fragmentation and is a measure of apoptosis. Activity of hL243 γ4P was compared to that of humanized MAbs against other B cell antigens, including anti-CD74 (hLL1), anti CD22 (hLL2, epratuzumab), anti-CD20 (hA20), as well as the murine-human chimeric MAb rituximab. Controls included no first MAb and the negative control humanized anti-CEA MAb, hMN-14. hL243 γ4P induced apoptosis in both cell lines, at levels similar to or greater than the other anti-B cell MAbs (FIGS. 18A and 21B).

A kit was used (eg the Guava Nexin™ kit) to discriminate between apoptotic and nonapoptotic dead cells in Daudi cells. The kit utilizes Annexin-V-PE to detect phosphatidylserine (PS) on the external membrane of apoptotic cells and a cell impermeant dye 7-AAD as an indicator of membrane structural integrity. 7-AAD is excluded from live, healthy cells and early apoptotic cells, but permeates late stage apoptotic and dead cells. As shown in FIG. 18B the results of this study indicated that hL243γ4P induced apoptosis similar to mL243 following both 4 h and 24 h treatment. In contrast, the anti-CD20 MAb did not induce measurable apoptosis in Daudi cells. Therefore, hypercrosslinking by a secondary agent, such as anti-human IgG or protein A may be used for induction of apoptosis by anti-CD20 MAbs in many cell lines including Daudi.

Figure 19:
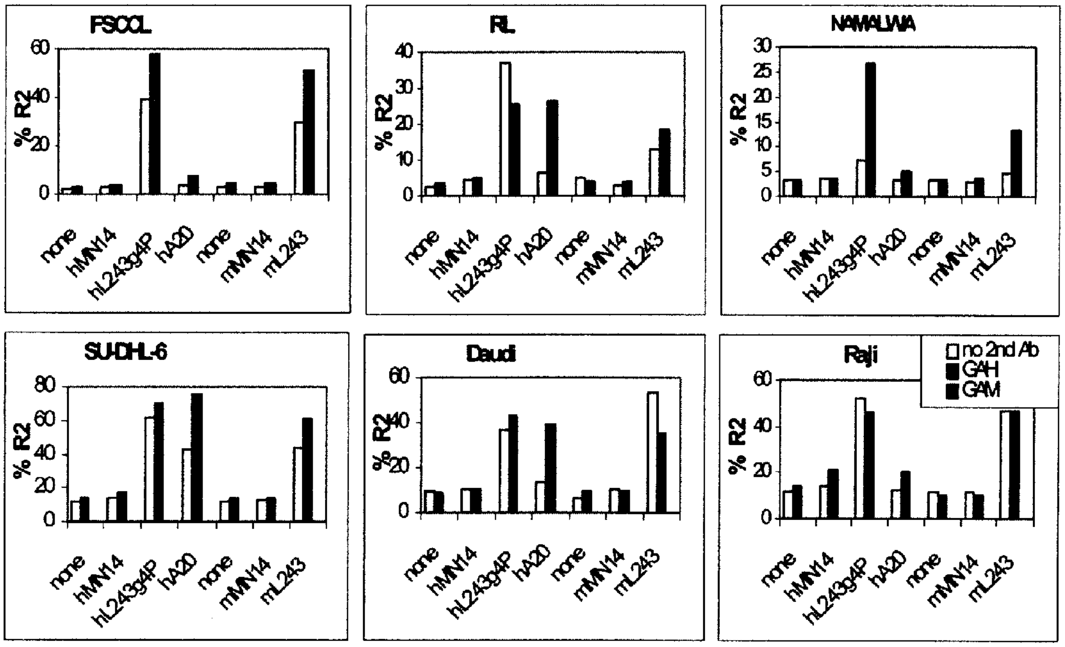
FIG. 19 illustrates mitochondrial membrane potential using a JC-1 assay in several cell lines.

In another example, the effects of humanized and murine L243 on mitochondrial potential was studied in different cells, namely, SU-DHL-6, Daudi, Raji, WSU-FSCCL, RL, and Namalwa. Results shown in FIG. 19 indicate apoptotic changes in the mitochondrial membrane potential were observed with both murine and humanized L243 MAbs. Crosslinking with a second antibody may not be needed, but can increase the effect in 2 of 6 cell lines evaluated, FSCCL and Namalwa. The loss of mitochondrial membrane potential induced by hL243γ4P was greater than that of the anti-CD20 MAb (hA20), without a crosslinking agent. With crosslinking the hA20 levels are increased to those of hL243γ4P in 3 of the 6 cell lines (RL, SU-DHL-6, and Daudi).

Induction of activated caspase-3 by humanized and murine L243 was assayed by flow cytometry in a panel of lymphoma cell lines. Result summarized in Table 6 show both the murine and humanized L243 induce activation of caspase-3, at similar levels, in the absence of crosslinking with second antibody. The induction of activated caspase-3 with the L243 MAbs is greater in all cell lines than that of hA20. With a second antibody these levels are increased and the effect of hA20 is similar to that of the hL243 γ4P, except in Namalwa and FSCCL, two cell lines which we routinely observe to be relatively insensitive to anti-CD20 MAbs. Cleaved caspase-3 was also assayed in Daudi over a 2 day time course (FIG. 20A). The activity continues to increase for approximately 2 days of L243γ4P incubation. Time points less than 1 h were not done.

The involvement of AKT in the mechanism of action of L243 was assayed in 6 cell lines by flow cytometry. Cells were incubated with various MAbs for 2 days, then assayed for phospho-AKT. The results listed in Table 7 show that L243 activates AKT in all cell lines. Phospho-AKT levels in anti-CD20 (hA20) treated cells, as well as anti-CD74 and anti-CD22 treated cells (not shown), are similar to untreated cells on all cell lines. To determine the time course of P-AKT activation, Daudi cells were incubated with MAbs for various times, MAbs were removed (by centrifugation) at time points from 0 min to around 2 days (FIG. 20B). These results show activation of AKT by L243 can occur faster than can be measured by this assay, because even at the zero time point P-AKT levels are equal to the 2 day time point.

In Vivo Therapeutic Efficacy of hL243 in a Xenograft Model of Non-Hodgkin's Lymphoma (Raji)

Figure 21:
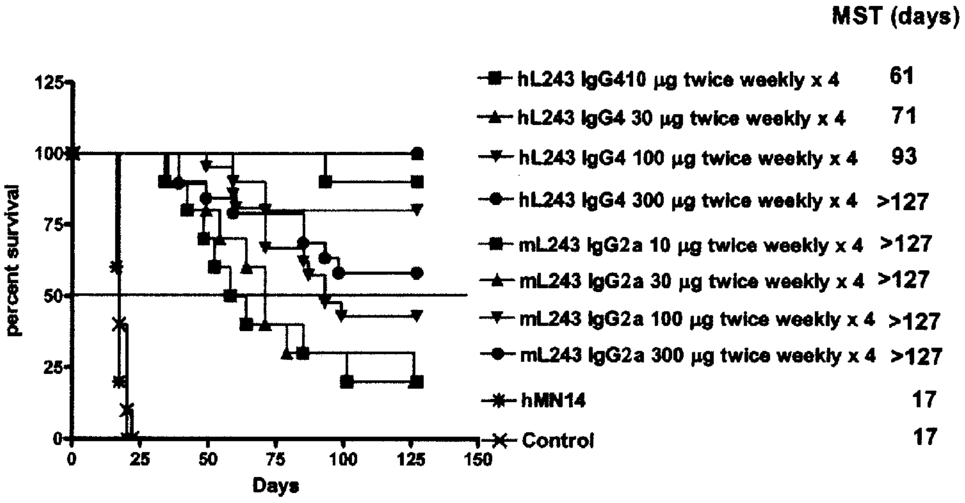
FIG. 21 illustrates therapy of Raji-bearing SCID mice with murine L243 and L243 γ4P.

A therapeutic study was performed to compare the in vivo efficacy of hL243γ4P and mL243 (IgG2a isotype) monoclonal antibodies, in a xenograft model of human non-Hodgkin's lymphoma (Raji). The aim of this study was to determine if hL243γ4P can maintain significant antitumor efficacy in a xenograft model. SCID mice were injected with $2.5\times10^6$ Raji cells. Therapy with hL243γ4P or mL243 was initiated 1 day-post tumor cell administration. Results are shown in FIG. 21. Both groups of mice injected with saline or with non-specific control antibody, hMN14, had a median survival time (MST) of 17 days. All the groups of mice treated with either humanized or murine L243 had significantly improved life span compared to mice injected with saline or hMN14 ($P<0.0001$). Treatment with various doses of hL243γ4P resulted in a dose-response relationship, with mice receiving higher doses having better survival times. In the group of animals treated with various doses of mL243 IgG2a, the cure rate was in the range of 80-100%.

Example 6

Anti-HLA-DR Antibody Therapy in Spontaneous Canine Lymphoma

Expression of HLA-DR on hematological malignancies has generated considerable interest in its development as a target for antibody-based therapy. Here we describe the use of anti-HLA-DR monoclonal antibodies (mAbs), L243 and IMMU-114 (hL243γ4P), a humanized IgG4 mAb engineered to eliminate adverse reactions associated with complement-activation, for antibody therapy in dogs with lymphoma.

Normal and malignant canine B cell binding, induction of apoptosis, antibody-dependent cellular-cytotoxicity (ADCC), complement-dependent cytotoxicity (CDC), and direct cytotoxicity of L243 and IMMU-114 were measured in vitro. Safety and pharmacokinetic data on L243 and IMMU-114 administration were collected in normal dogs, followed by a preliminary trial of L243 in dogs with advanced lymphoma or unresectable plasmacytoma.

L243 and IMMU-114 were observed to bind to normal canine lymphocytes and canine lymphoma cells. In vitro, murine L243 and IMMU-114 binding yielded a reduction in viable cell counts and induction of apoptosis in canine lymphoma cells. When incubated with canine serum or peripheral blood mononuclear cells, L243, but not IMMU-114, induced CDC and ADCC, respectively. In vivo, both anti-HLA-DR mAbs can be administered safely to dogs and bind to malignant cells. Evidence of clinical activity (hematopoietic toxicity and tumor response) was observed in dogs with advanced-stage lymphoma following L243 immunotherapy.

To avoid complications associated with complement-dependent cytotoxicity (CDC) and antibody-dependent cellular cytotoxicity (ADCC), we recombinantly-engineered a humanized IgG4 construct of the murine anti-HLA-mAb, L243, referred to as hL243γ4P (IMMU-114) (Stein et al., 2006, Blood 108:2736-44). The IgG4 isotype was prepared because human Fcγ receptors are known to have low affinity for the human IgG4 isotope (Ravetch and Kinet, Ann Rev Immunol, 1991, 9:457-92). A point mutation, Ser241Pro, was introduced into the hinge region of the γ4 sequence in order to avoid formation of half-molecules when the antibody is expressed and produced in mammalian cell cultures, thus the designation, γ4P. As discussed in the preceding Examples, replacing the Fc region of a humanized IgG1 anti-HLA-DR mAb with the IgG4 isotype abrogated the effector cell functions of the antibody (ADCC and CDC), while the antigen-binding properties, anti-proliferative capacity (in vitro and in vivo), and the ability to induce apoptosis concurrent with activation of the AKT survival pathway and other signaling pathway effects, were retained. Thus, IMMU-114 is indistinguishable from the parental murine mAb and a humanized IgG1 anti-HLA-DR mAb in assays dependent upon antigen recognition. The abrogation of ADCC and CDC may be preferred for in vivo therapeutic use.

Materials and Methods

Antibodies. The following mAbs were used for phenotyping: anti-CD3-FITC, anti-CD4-FITC, anti-CD8-PE, and B cell-PE, purchased from Serotec Ltd (Raleigh, N.C.), unlabeled anti-human CD22 (LL2) and anti-human CD74 (LL1), supplied by Immunomedics, Inc. (Morris Plains, N.J.), unlabeled anti-human-CD3, -CD20, and -CD45 (Leu 4, Leu-16, and H-Le-1, respectively), purchased from BD Biosciences (San Jose, Calif.), and anti-CD20 mAbs, 2B8 and 1F5, purified from culture fluids of hybridoma cells obtained from the American Type Culture Collection (ATCC, 10801 University Blvd., Manassas, Va. 20110-2209). Murine mAbs Ag8 (P3x63 Ag8, ATCC) and MN-14 (anti-carcinoembryonic antigen [CEA, CEACAM5 or CD66e]) were used as isotype controls. L243 and humanized mAbs, IMMU-114 (hL243γ4P), milatuzumab (hLL1, anti-CD74 mAb) (Stein et al., Blood, 2004, 104:3705-11), veltuzumab (hA20, anti-CD20) (Stein et al., Clin Cancer Res, 2004, 10:2868-78), epratuzumab (hLL2, anti-CD22) (Leung et al., Molecular Immunol, 1995, 32:1416-27), and labetuzumab (hMN-14, anti-CEA) (Sharkey et al., Cancer Res, 1995, 55:5935s-45s), were from Immunomedics, Inc.

Flow Cytometry. Peripheral blood lymphocyte subsets were determined using flow cytometry. The different leukocyte populations were identified by their distinctive position on forward and side scatter plots. The lymphocyte population was gated and 10,000 events were acquired for each antibody. All flow cytometry experiments were performed and analyzed using a FACSCalibur (Becton Dickinson, San Jose, Calif.). The data were analyzed with CellQuest software. Immunostaining was performed according to the manufacturer's directions. Briefly, a 100-μl aliquot of whole blood in EDTA was incubated with either antibody or isotype control antibody for 15 min at room temperature. Red blood cells were lysed with 2 ml of FACS lysing solution and incubated for 5 min. The cells were washed in phosphate-buffered saline (PBS), pH 7.4. The cell pellet was resuspended in PBS containing 20 mM glucose and 1% bovine serum albumin and immediately assayed by flow cytometry.

Determination of HLA-DR and CD20 antigen expression on normal and neoplastic cells was performed by indirect immunofluorescence assays using FITC-goat anti-mouse IgG (GAM, Invitrogen, Carlsbad, Calif.), as described previously (Stein et al., Blood, 2006, 108:2736-44).

In Vitro Cytotoxicity and Apoptosis Assays. Apoptosis was evaluated by flow cytometry. Briefly, cells were incubated with mAbs for 48 h with or without a second antibody for cross-linking, followed by DNA staining with propidium iodide. Samples were analyzed by flow cytometry using a FACSCalibur. Percentage of apoptotic cells was defined as the percentage of cells with DNA staining before G1/G0 peak (hypodiploid).

Standard $^{51}Cr$ release assays were used to measure ADCC and CDC. Briefly, for CDC a 1/8 final dilution of canine serum was used as the source of complement, followed by a 3-h incubation. Cells treated with 0.25% Triton X-100 were included as 100% lysis control, and cells treated with complement alone as 0% lysis. For ADCC, effector:target cell ratios of approximately 50:1 were used, and incubations were for 4 h. All assays were performed in triplicate.

In Vivo Studies. Sterile antibodies were diluted in a total volume of 90 ml and 250 ml of 0.9% NaCl for administration to normal dogs and dogs with lymphoma, respectively. All dogs were pre-medicated with 4 mg/kg diphenhydramine intramuscularly 20 min prior to antibody infusion. The dogs were monitored continuously during the infusion, and vital signs and body temperature were recorded every 30 min. If adverse events (vomiting, erythema, pruritus, weakness, tachycardia) were observed, the infusion was stopped for at least 15 min and restarted at half the initial infusion rate. The normal dogs' rectal temperature was taken twice daily for 7 days following each antibody infusion. Adverse events were graded according to the veterinary co-operative group—common terminology criteria (Veterinary co-operative oncology group, Vet Comparative Oncol, 2004, 2:194-213).

Normal Dogs. Intact female beagle dogs were used to assess systemic toxicity with L243 (2 dogs) and IMMU-114 (2 dogs) antibody administration. The dogs were deemed healthy based on physical examination, complete blood cell count, biochemical profile, and urinalysis. L243 was administered at 1.5 mg/kg of body weight over a planned 90-min interval to the first dog. This dose was extrapolated from previous dose ranging studies in mice. The antibody infusion was repeated on day-7 in this dog. The dose of L243 was increased to 3 mg/kg for the second dog, since there was minimal toxicity noted in dog-1. The second dose was repeated on day-2 rather than day-7, to determine if increased toxicity would be detected with a shorter interval between treatments. IMMU-114 was administered at 3 mg/kg infused over a 90-min period to 2 dogs. One of the dogs was infused a second time 2 weeks later at 1.3 mg/kg.

Blood was collected into ethylenediamine tetraacetic acid (EDTA) tubes for complete blood cell counts and peripheral blood lymphocyte phenotyping at 4, 24, 48, and 72 h and at 7, 14, 21 days after the first infusion. Biochemical profiles and urine were analyzed at 7, 14, and 21 days after the first infusion. Dogs were humanely euthanized by intravenous pentobarbital sodium injection 30 days after the first infusion. Necropsies were performed post mortem and tissue samples were collected in formalin for histologic review by a board certified pathologist.

Dogs with Lymphoma. Dogs were enrolled in this study if they had histologic or cytologic confirmation of lymphoma or plasma cell neoplasia and had previously failed or were refractory to conventional cytotoxic chemotherapy or if the owner had declined other therapy. Chemotherapy was not administered concurrently or less than 3 weeks prior to treatment with HLA-DR mAb. Pretreatment evaluation for all tumor-bearing dogs included physical examination, complete blood cell count, biochemical profile, and urinalysis. Dogs were excluded if there was evidence of ≥grade 2 toxicity on screening studies. Lymph nodes or tumors were measured in 3 dimensions and tumor volume was calculated as the product of length, width, height, π/6. Dogs received 1 to 4 treatments administered at 2-week intervals at a dosage of 3 mg/kg intravenously. Based on the normal dog studies above, the starting protocol for infusion of L243 was planned over a 4-h period. Due to delays caused by infusion reaction in some of the dogs, the infusion was slowed to 3 mg/kg over 12 h. Adverse infusion events were monitored continuously in an intensive care setting during the infusion. Complete blood cell count, chemistry profile, urinalysis and tumor measurements were evaluated weekly.

Enzyme-Linked Immunoabsorbent Assay (ELISA). L243 and IMMU-114 serum levels were measured by ELISA. Two ml of whole blood were collected pretreatment, at the end of the antibody infusion, 1 h after the end of the infusion and at 24 h. The samples were allowed to clot at room temperature for 30 min and the serum was separated and frozen at −80° C. prior to analysis. The ELISA assays were performed in 96-well PVC microtiter plates. Plates were coated overnight with goat anti-mouse IgG F(ab')$_2$ fragment specific antibody at 10 μg/ml in PBS, 0.02% $NaN_3$ (Jackson Immunoresearch, West Grove, Pa.), then blocked with 1% BSA/PBS, 0.02% $NaN_3$ for 1 h at room temperature. Triplicate serum dilutions (in 1% BSA/PBS, 0.02% $NaN_3$ at 1/3, 1/10, 1/30, and 1/100) were incubated for 1 h in the coated wells. A standard curve of L243 or IMMU-114 was run in the same plate. After washing with PBS, 0.05% Tween, peroxidase conjugated goat anti-mouse (or anti-human) IgG, Fcγ specific antibody (1:3000 dilution in 1% BSA/PBS, Jackson Immunoresearch) was added and the plate was incubated for an additional 1 h at room temperature in the dark. The plates were washed, developed with o-phenylenediamine dihydrochloride substrate solution and read at 490 nm, after stopping the reaction by adding 1.5 N $H_2SO_4$.

Statistics. P-values were calculated using the Student's t test. Two-sided tests were used throughout. Values less than 0.05 are considered statistically significant. For ADCC and CDC assays, P values were calculated versus the no-antibody control.

Results

Figure 22:
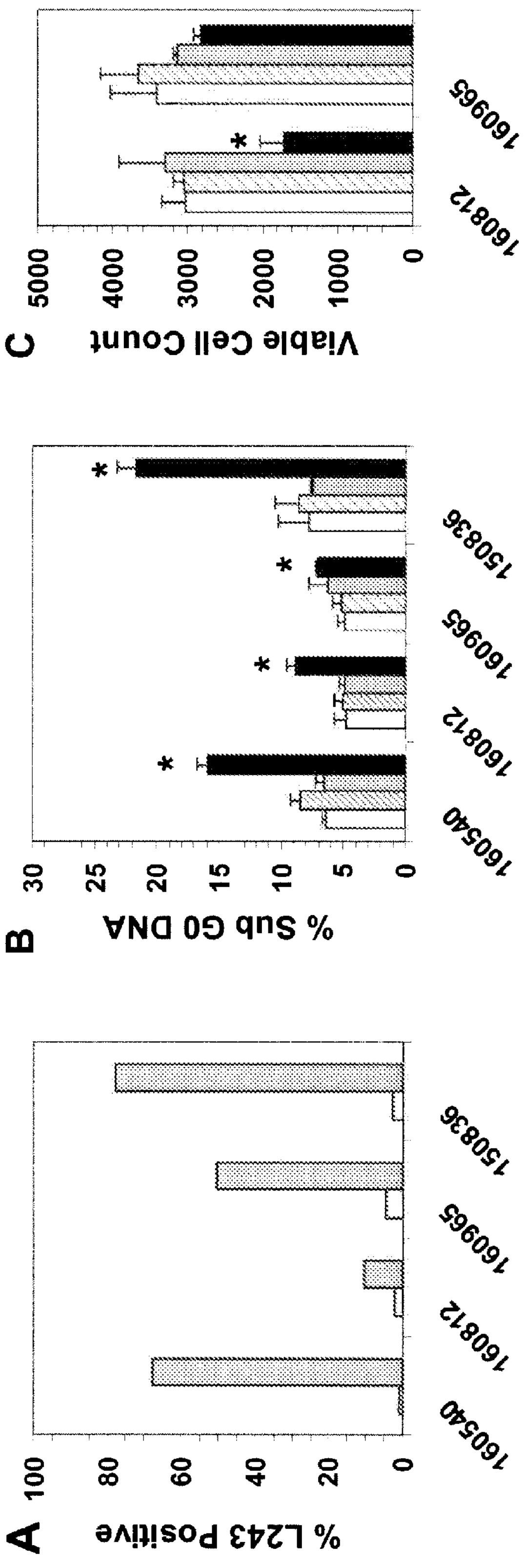
FIG. 22. In vitro effects of murine L243 on canine lymphoma aspirates. (A) L234 binding to the aspirates from 4 dogs. White bars, Ag8; gray bars, L243. (B) Percent apoptotic cells as measured by flow cytometry of hypodiploid DNA (sub G0) following propidium iodine staining Incubations were performed without second antibody or in the presence of goat anti-mouse IgG. (C) Viable cell count was performed on two of the specimens by flow cytometry analysis of the cell count within a viable gate defined in the forward scatter vs. side scatter dot plot. For panels B and C: white bars, Ag8 without second antibody; striped bars, Ag8 with GAM; gray bars, L243 without second antibody; black bars, L243 with GAM; *, P<0.05 vs. Ag8.

In Vitro Effects of L243 on Proliferation and Apoptosis. Lymph node aspirates from four dogs with lymphoma were incubated with mAb L243 in vitro to determine the effects of the mAb on proliferation and apoptosis. All four specimens were positive for L243 binding (FIG. 22A). Induction of apoptosis by L243 was evaluated by flow cytometry assays measuring hypodiploid DNA. Cells were cultured with the mAbs for 48 h with or without a second mAb for cross-linking, followed by DNA staining with propidium iodide. Cells were analyzed by flow cytometry, and positive fluorescence below the G0/G1 region represents DNA fragmentation and is a measure of apoptosis. As shown in FIG. 22B, L243 caused specific induction of apoptosis in the presence of goat anti-mouse IgG second antibody ($P<0.05$ vs. crosslinked isotype control) in all four specimens. Viable cell counts were measured after 2-day incubations of the tumor aspirates with L243 plus goat anti-mouse IgG second antibody. Decreases in the viable tumor cell population of 43% (P=0.0088) and 23% (P=0.097) were obtained in specimens 160812 and 160965, respectively, vs. Ag8 plus goat anti-mouse IgG second antibody (FIG. 22C). Specimens 160540 and 150836 were not tested by this assay. ADCC and CDC assays were performed on one tumor aspirate, from dog 171205, using PBMCs or serum isolated from that animal as sources of effector cells and complement, respectively. Statistically significant lysis was observed with L243 but not an isotype control (MN-14) in both assays. For CDC, lysis was 38.1%±0.9% (P=0.0004) and 1.1±2.2% (P=1.0000) for L243 and isotype control, respectively. For ADCC, lysis was 26.6±15.9% (P=0.0319) and −6.9±18.36% (P=0.4544) for L243 and isotype control, respectively. Thus, crosslinked L243 yields a specific therapeutic effect on canine lymphoma aspirates, leading to a reduction in viable cell count and induction of apoptosis, as measured by DNA fragmentation. When incubated with dog serum or PBMCs, L243 induces CDC and ADCC.

Figure 23:
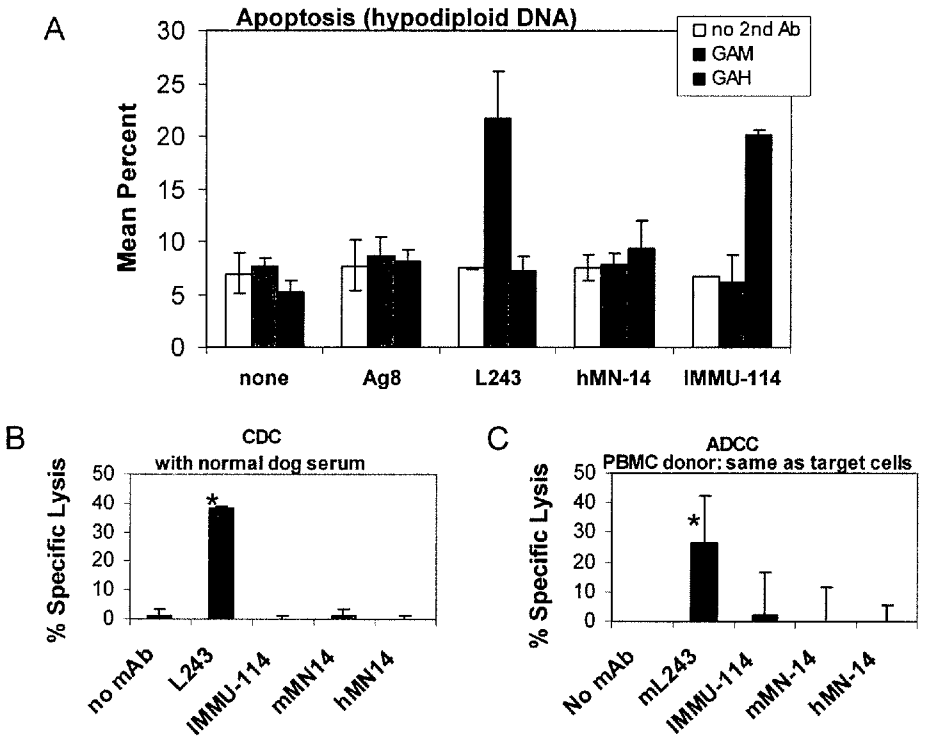
FIG. 23. In vitro effects of IMMU-114 on canine lymphoma aspirates. (A) Percent apoptotic cells as measured by flow cytometry of hypodiploid DNA (sub G0) following propidium iodine staining Incubations were performed without second antibody or in the presence of goat anti-mouse IgG (GAM) or goat anti-human IgG (GAH). (B) and (C) Percent specific lysis in CDC and ADCC assays on aspirate of dog #171205. Error bars, SD of three replicates. *, significant change (P<0.05) relative to no mAb control.

We also demonstrated that IMMU-114 (humanized, engineered L243) binds to canine lymphoma cells (Table 8). In addition, IMMU-114 induces apoptosis in the canine lymphoma cells when crosslinked with an anti-human IgG second antibody (FIG. 23A). Evaluation of the ability of IMMU-114 to induce CDC and ADCC was performed on one canine lymphoma aspirate (171205). As shown in FIGS. 23B and 23C, murine L243 but not IMMU-114 yielded specific cell lysis of the dog lymphoma cells, confirming the lack of CDC and ADCC effector functions of IMMU-114.

L243 Administration In Vivo. Safety data on L243 infusion was collected in two normal dogs, followed by a trial in 6 dogs with relapsed lymphoma, and 1 dog with an unresectable plasmacytoma.

Figure 24:
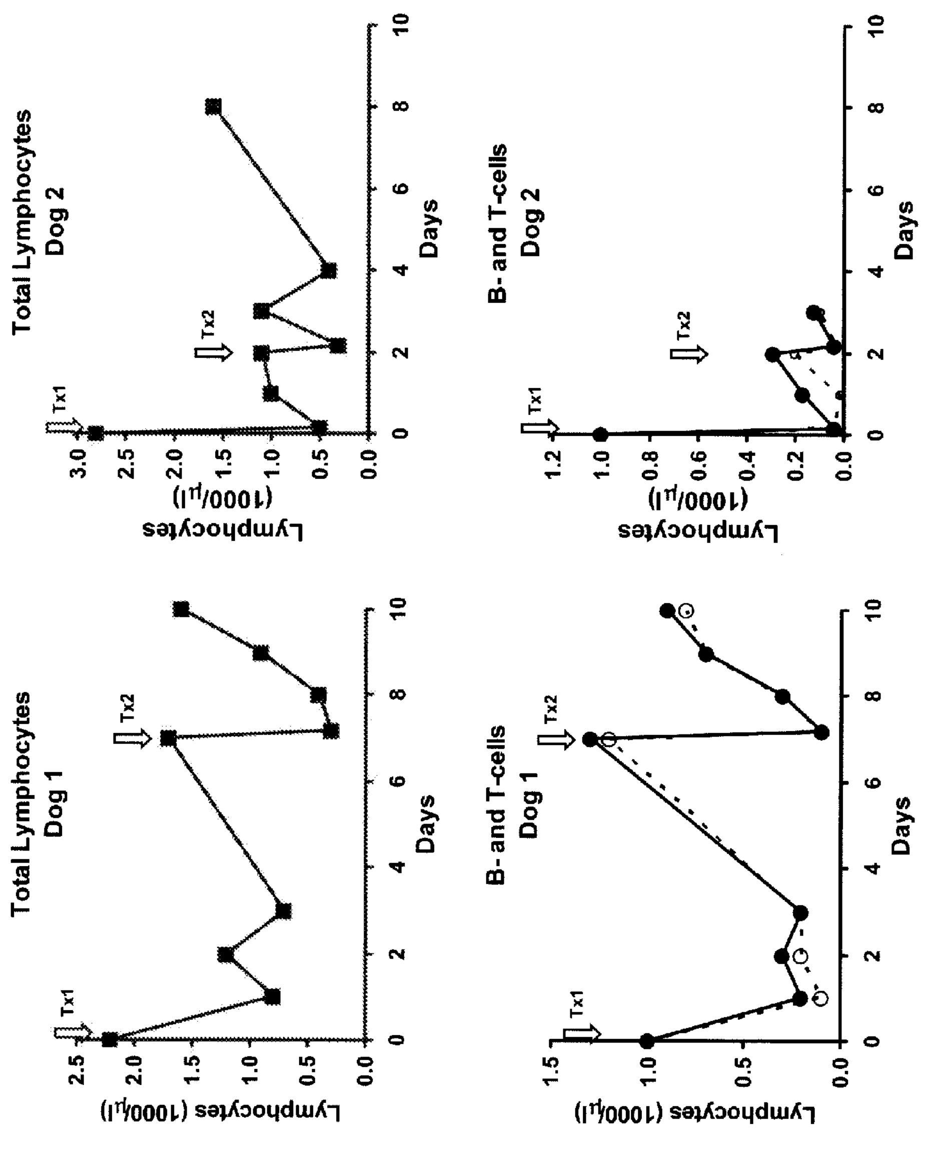
FIG. 24. Peripheral blood lymphocyte count and lymphocyte subset phenotyping indicated a decrease in both B- and T-cell lymphocytes. ■, total lymphocyte count; ●, T-cell count, relative to baseline; ○, B cell count, relative to baseline.

Normal Dogs. Dog 1 received 2 infusions of 1.5 mg/kg, 7 days apart. An infusional reaction occurred during the first antibody administration that included grade I nausea/vomiting and grade I fever. Decreasing the infusion rate by 50% (from an initial rate of 0.2 mg/ml/min) eliminated the adverse reactions. There were no adverse events during the second infusion. Dog 2 received 2 infusions of 3.0 mg/kg, 48 hours apart (0.25 mg/ml/min). There were no adverse reactions during either infusion. There were no significant changes in the post-infusion biochemical profiles or urinalysis in either dog. Mature neutrophils were transiently elevated in Dog 2 ($13.3\times10^3$/μl; normal range 3.4-$9.7\times10^3$/μl) 24 h after the first infusion and normalized within 24 h. Both dogs had a marked transient increase in band neutrophils. Dog 1 had 1000/μl band neutrophils 4 h after the second infusion (normal range 0-100/μl); Dog 2 had 1300/μl band neutrophils 24 h after the first infusion. Both dogs had normal band neutrophil counts 24 h later. Lymphopenia (800/μl-dog 1, 500/μl-dog 2: normal range 1000-4000/μl) was noted 4-24 h following the first infusion in both dogs and following the second infusion in dog 2. Lymphocytes returned to normal within approximately 1 week following infusion. Peripheral blood lymphocyte subset phenotyping indicated a decrease in both B and T cell lymphocytes (FIG. 24). Such rapid changes in neutrophils and lymphocytes represent a non-specific component to immunogens in dogs. Resolution of the neutrophilia occurred within one day and lymphocyte populations recovered over a 7-day period. Complete necropsy examination of Dogs 1 and 2 did not reveal any gross or histologic abnormalities.

Tumor-Bearing Dogs. Seven dogs with lymphoma/plasmacytoma were treated with L243. The median age of the patients was 10.8 years (range 8.4-11.9 years). The median body weight was 35 kg (range 12.6-51.2 kg). There were 4 male dogs (2 intact, 2 castrated), and 3 female dogs (all spayed). Four of the dogs had B cell lymphoma, 2 had T-cell lymphoma, and 1 had an unresectable plasmacytoma. All dogs were staged according to WHO guidelines for canine lymphoma: 3 were stage V, 2 were stage III, and one remained incompletely staged. Four of the six lymphoma patients had failed initial conventional and rescue chemotherapy treatments. The remaining two lymphoma patients had received prednisone as their only therapy prior to presentation and their owners' had declined standard chemotherapy. All previous chemotherapeutic agents were discontinued 2-4 weeks prior to L243 therapy.

Toxicity. Infusional side-effects were common with 6/7 patients, experiencing grade 1 nausea or vomiting and 5/7 experiencing grade 1 fever. Slowing the infusion rate abrogated the adverse reactions. Two dogs received dexamethasone at 0.5-2 mg/kg i.v. due to vomiting and elevated temperature. No dog had treatment discontinued due to adverse events. Hematologic toxicity was noted in 3/7 patients. One dog had grade 1 neutropenia and grade 1 thrombocytopenia two weeks after the first infusion. This dog received a total of 3 treatments and did not exhibit any additional hematologic abnormalities. In two dogs, grade 3 neutropenia and grade 4 thrombocytopenia were observed one week after the second infusion. Both of these dogs were heavily pretreated with chemotherapy prior to antibody infusion. Bone marrow aspirates indicated a non-specific granulocytic and megakaryocytic hypoplasia. One dog was euthanized due to hemorrhage from multiple ulcerated cutaneous lymphoma lesions. The second dog's cytopenias resolved uneventfully by the fourth week post infusion. One dog died suddenly at home approximately 5 days after L243 therapy due to rapidly progressing, resistant lymphoma. A necropsy was not performed.

Response to Therapy. Two dogs with advanced, multicentric B cell lymphoma had a transient response to L243 therapy. One dog had stable disease with complete resolution of circulating lymphoblasts for 5 weeks following the second infusion, with improvement in attitude and appetite. This dog received a total of three treatments. His disease progressed 8 weeks after his first L243 treatment. The second dog had a 50% reduction in the size of peripheral lymph nodes observed by physical examination and measurement of peripheral lymph node volume one week after the first treatment. The partial response lasted 8 weeks before progressive disease was noted. This dog received a total of 4 treatments without evidence of any toxicity. Both dogs received a brief course (1-2 weeks) of corticosteroid prior to L243 therapy. In each instance, the dogs had progressive disease on corticosteroids prior to L243 infusion and all corticosteroid therapy was discontinued before treatment.

A comparison of cells aspirated from a lymph node prior to L243 with cells obtained one week after the first L243 infusion was performed in order to assess in vivo targeting of the L243 mAb. The histograms represented baseline and one-week post infusion aspirated cells, to which no first or second antibodies were added in vitro (not shown). The profiles of the baseline cells and week-1 cells overlapped (not shown). The cells were incubated in vitro with FITC-labeled GAM, to detect cells that were labeled with L243 in vivo (not shown). Cells obtained from the same lymph node 1 week after treatment with L243 were shifted to the right of the baseline cells, demonstrating the binding of murine IgG to the cell surface (not shown). The cells were incubated in vitro with L243 and FITC-GAM to determine whether the cells were saturated with mAb L243. Aspirated cells taken 1 week after treatment with L243 coincided with the baseline cells because the in vivo and in vitro binding of L243 IgG to the cell surface are indistinguishable after saturating doses of L243 (not shown). Both groups exhibited higher mean fluorescence compared to that of the FITC-GAM labeled cells, indicating that the in vivo L243 dose administered did not saturate all malignant cells in the node (not shown). Data obtained from cells aspirated 2 weeks after infusion continue to demonstrated L243 binding to malignant lymphocytes (not shown). An alternate explanation is that some of the bound L243 was internalized or processed, and the antigen remains on or returns to the cell surface, able to bind additional antibody. Cells were incubated in vitro with Ag8 (isotype matched, nonspecific mAb) and FITC-GAM. Aspirated cells taken 1 week after infusion with L243 were shifted to the right of the baseline cells, again demonstrating the binding of murine IgG to the cell surface (not shown). Only the cells labeled in vivo with L243 bind to the FITC-GAM, because Ag8 does not bind to the cells. This assay demonstrated that L243 targeted the tumor cells in vivo.

Figure 25:
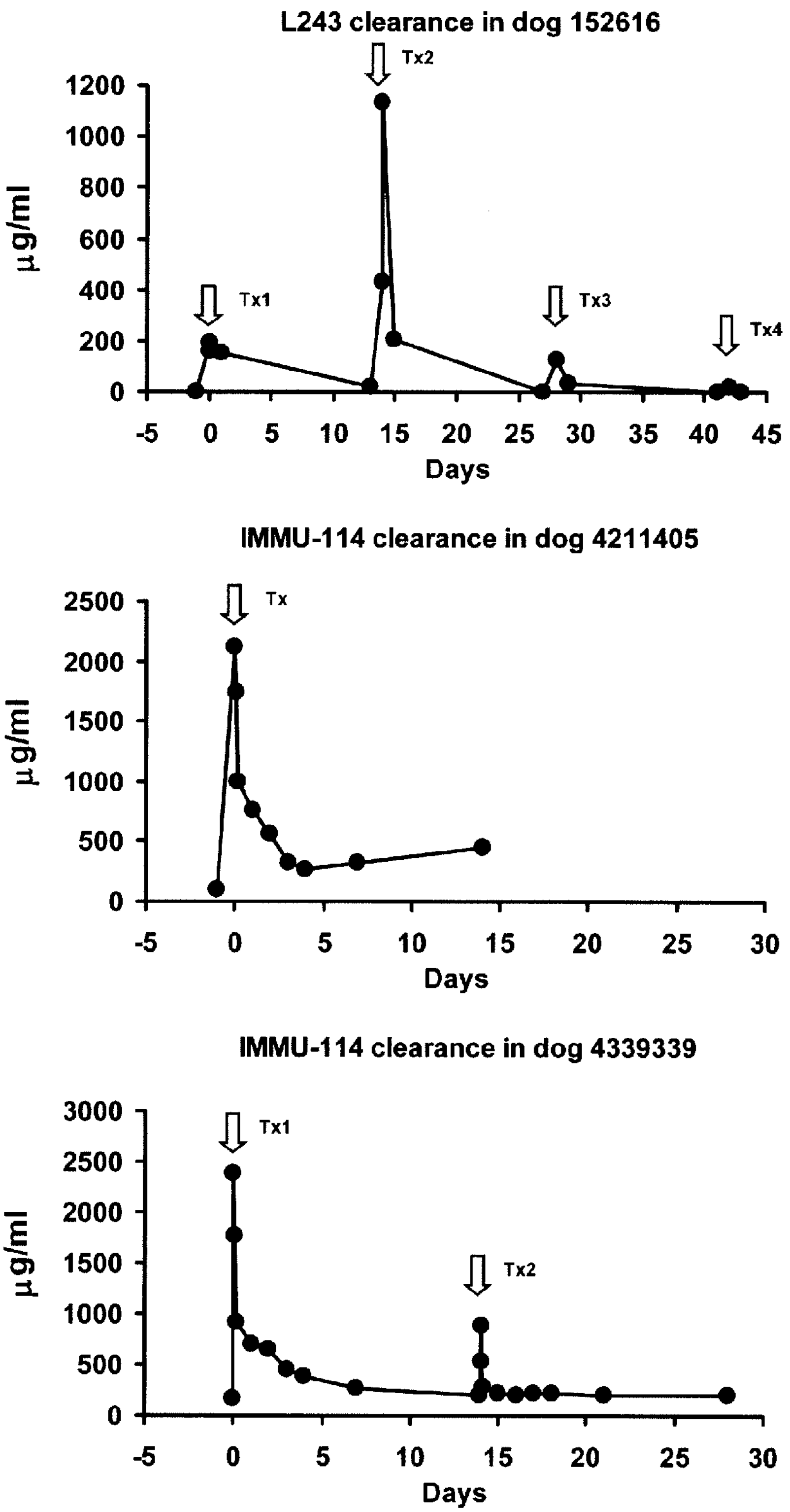
FIG. 25. Clearance of L243 in a dog with lymphoma (A) and of IMMU-114 in two normal dogs (B and C). The L243 doses administered in the dog with lymphoma (A) were 1.5 mg/kg for treatment 1 and 3.0 mg/kg for the remaining 3 treatments. IMMU-114 doses were 3.0 mg/kg for the initial dose in both normal dogs (B and C). The second dose of IMMU-114 administered to second normal dog (C) was 1.3 mg/kg.

The L243 antibody was measured by ELISA in the serum of the last treated dog (152616). Samples were collected prior to the antibody infusion, at the end of the infusion, 1 h post infusion and at 24 h at each of the 4 treatments (FIG. 25). The serum level of L243 detected after the second infusion was markedly higher than after the first infusion. This suggests that the antigen pool present on cell surfaces was either blocked or eliminated by the first infusion. Infusions 3 and 4 yielded progressively lower serum concentrations of L243. This was likely due to an anti-antibody response causing rapid clearance of the infused murine L243 antibody. Because the presence of anti-mouse IgG was not measured, reappearance of an antigen sink cannot be ruled out.

IMMU-114 Administration In Vivo. Once IMMU-114, the humanized reengineered IgG4 form of murine L243, became available, it was administered to 2 normal beagles at 3 mg/kg over 90 min. There was no infusion reaction noted in either dog during the infusion. One of the dogs was infused a second time 2 weeks later (at 1.3 mg/kg). A mild infusion reaction that included head shaking, mild fever and vomiting occurred following the second infusion. The severity of the reaction was lessened by slowing the rate of the infusion. This may suggest the development of anti-human IMMU-114 antibody. CBCs and biochemical panels were conducted with no significant changes noted over a 2-week period, with the exception of a transient lymphopenia as also observed with L243 infusion. Pharmacokinetic (PK) data obtained at the end of infusion, and 1, 4, 24, 48, 72 h, 1 week, and 2 weeks post-infusion indicated a rapid clearance within the first few hours, with about 50% of the IMMU-114 antibody cleared within 2 h, and with the remaining antibody clearing with a half-life of ~2 days (FIG. 25).

Discussion

Naturally-occurring lymphoma in dogs is extremely common and has been validated as a useful model of high-grade, B cell, non-Hodgkin's lymphoma in humans. Conventional chemotherapeutic management of lymphoma in dogs, as in humans, is limited with 5-20% 2-year survival rates following CHOP-based chemotherapeutic protocols. The availability of canine lymphoma patients, the ability to investigate novel strategies with repeated sampling of normal and tumor tissue or fluid, as well as the design of rigorous clinical trials to determine relevant therapeutic endpoints, are recognized advantages of this model as a bridge from preclinical investigations to humans. Although anti-CD20 antibodies have contributed to improved outcomes in some forms of lymphoma in humans, the commercially available human anti-CD20 antibodies do not bind sufficiently with canine B cell lymphomas to permit further investigations of this strategy. However, substantial opportunities exist to expand the investigation of other antibody-based immunologic therapeutics.

Lymphoma is an increasingly common form of cancer with a wide range of immunologic and genetic subcategories with equally diverse prognoses. Aggressive forms of non-Hodgkin's lymphoma are currently controlled with chemotherapy with or without antibody infusions with only a moderate degree of success. Novel immunotherapeutic approaches, such as infusion of anti-B cell mAbs to improve the management of lymphoma, are traditionally examined in murine models but should be more carefully evaluated prior to human study to identify and better anticipate the impact of such interventions. Studies in the present canine model are important to the translation of IMMU-114 to clinical studies in humans, particularly given the prior clinical experience with another anti-HLA-DR antibody (Hu1D10; apolizumab), where moderate to severe side effects, primarily related to robust immune effector activity (e.g., mainly CDC) limited its dosing (Shi et al., Leuk Lymphoma, 2002, 43:1303-12. In order to expedite the scientific and practical decisions about progression of new immunotherapeutic strategies into humans with B cell malignancies, prudent use of the canine lymphoma model to address both safety and efficacy represents a truly comparative approach to cancer investigation.

The effects of anti-HLA-DR antibodies on malignant cells have been studied extensively. The most widely recognized function of class II major histocompatibilty complex (MHC) molecules is the recognition of foreign antigen fragments and presentation to CD4 T lymphocytes. In addition, signals delivered via HLA-DR molecules contribute to the functioning of the immune system by up-regulating the activity of adhesion molecules, inducing T-cell antigen counter receptors, and initiating the synthesis of cytokines Stimulation of HLA molecules by antibodies has been shown to affect growth, differentiation, and immunoglobulin secretion by B lymphocytes, as well as production of cytokines, modulation of expression of growth factor receptors, cell adhesion, and co-stimulatory molecules by B cells and monocytes (Nagy et al., J Mol Med, 2003, 81:757-65). HLA molecules have also been shown to serve as receptors that activate various cell death pathways, including caspase-dependent and caspase-independent alternative pathways of apoptosis (Nagy et al., J Mol Med, 2003, 81:757-65; Mone et al., Blood, 2004, 103:1846-54; Newell et al., PNAS USA 1993, 90:10459-63; Truman et al., Blood, 1997, 89:1996-2007). Functions reported to be affected by incubation of cells with L243 have included signal transduction, growth inhibition, Fas-mediated apoptosis, interactions with actin microfilaments, TNF-α and TNF-β gene expression, cell adhesion, ADCC, and others (see, e.g., Nagy et al., J Mol Med, 2003, 81:757-65; Mone et al., Blood, 2004, 103:1846-54; Newell et al., PNAS USA 1993, 90:10459-63; Truman et al., Blood, 1997, 89:1996-2007; Altomonte et al., J Cell Physiol, 2004, 200:272-6; Aoudjit et al., Exp Cell Res 2004, 299:79-90; Guo et al., Hum Immunol, 1999, 60:312-22). Enhanced cell kill over rituximab alone is demonstrated when the IMMU-114, is combined with rituximab in vitro (Stein et al., 2006, 108:2736-44). Recent studies have shown that antigen expression is not sufficient for cytotoxicity, but that antibody-induced activation of extracellular signal-regulated kinase (ERK) and c-Jun N-terminal kinase (JNK) stress signaling pathways are also required (Stein et al., unpublished).

The results reported here show that the anti-HLA-DR antibodies, L243 and IMMU-114, are able to induce cell death of canine lymphoma cells in vitro and can be given safely to dogs with lymphoma that are not heavily pretreated with chemotherapy. From this study, we were able to obtain valuable information regarding the dose and infusion rate for canine patients diagnosed with B cell lymphomas. The primary reaction following initiation of the infusion was mild and was characterized by a grade 1 fever and grade 1 nausea/vomiting. Myelosuppression was only noted in canine patients that were heavily pretreated with other chemotherapeutic agents. No other severe acute reactions were observed.

Two dogs with T-cell lymphoma were treated. Our preliminary work demonstrated that the T-cell form of lymphoma did not bind L243 significantly. We chose to enroll these dogs to identify whether the infusion reaction may be non-specific in an L243-negative tumor. Neither dog expressed the L243 antigen on the tumor cells. Both of these dogs experienced similar infusion reactions to those dogs with L243+ B cell tumors.

All dogs had tumor measurements and were evaluated for response. The two dogs with B cell lymphoma that had received prednisone as their only prior therapy experienced measurable responses to L243. One experienced a minor, but measurable, response with significant improvement of advanced symptoms, while the second had a partial response lasting 8 weeks. Five dogs did not demonstrate an obvious tumor response. Dogs in this group were L243− negative (T-cell lymphoma) or had end-stage disease at the time of treatment.

In vitro studies showed that murine L243 and its humanized IgG4 construct, IMMU-114, bind to normal and malignant canine lymphocytes and subsequently induce biological activity. In vivo studies indicate that the murine and humanized mAbs can be administered safely to dogs with lymphoma and bind to the malignant cells in nodal tissue. Preliminary evidence of disease stabilization was observed in dogs with advanced-stage lymphoma following anti-HLA-DR immunotherapy.

Example 7

Comparative Effects of Different Specificity Antibodies

The cross-reactivity of a panel of anti-human B cell mAbs with dog lymphocytes was evaluated using peripheral blood from a healthy dog. A human blood sample was tested at the same time as a control. Single color indirect flow cytometry analysis was performed. Reactivity of the mAb panel with the human lymphocytes was within the expected range. MAbs against human CD20 (1F5) and HLA-DR (L243) reacted with the dog lymphocytes. Anti-human CD22 (LL2), CD74 (LL1), and mAbs recognizing human CD3 (Leu 4), CD20 (Leu-16), and CD45 (H-Le-1) did not cross-react with dog lymphocytes. Based on these initial results, tumor aspirates obtained through a large gauge needle from dogs with lymphoma were tested for binding to anti-HLA-DR and anti-CD20 murine mAbs. Anti-HLA-DR (L243) was positive in 32/35 samples (greater than 5 units above the isotype control) and strongly positive (greater than 10 units above the negative control) in 30/35 samples. In contrast, anti-CD20 (2B8 used in these studies) was positive in 5/21, including 3 strongly positive. Reactivity of L243 was confirmed on the peripheral blood of several of these dogs.

Figure 26:
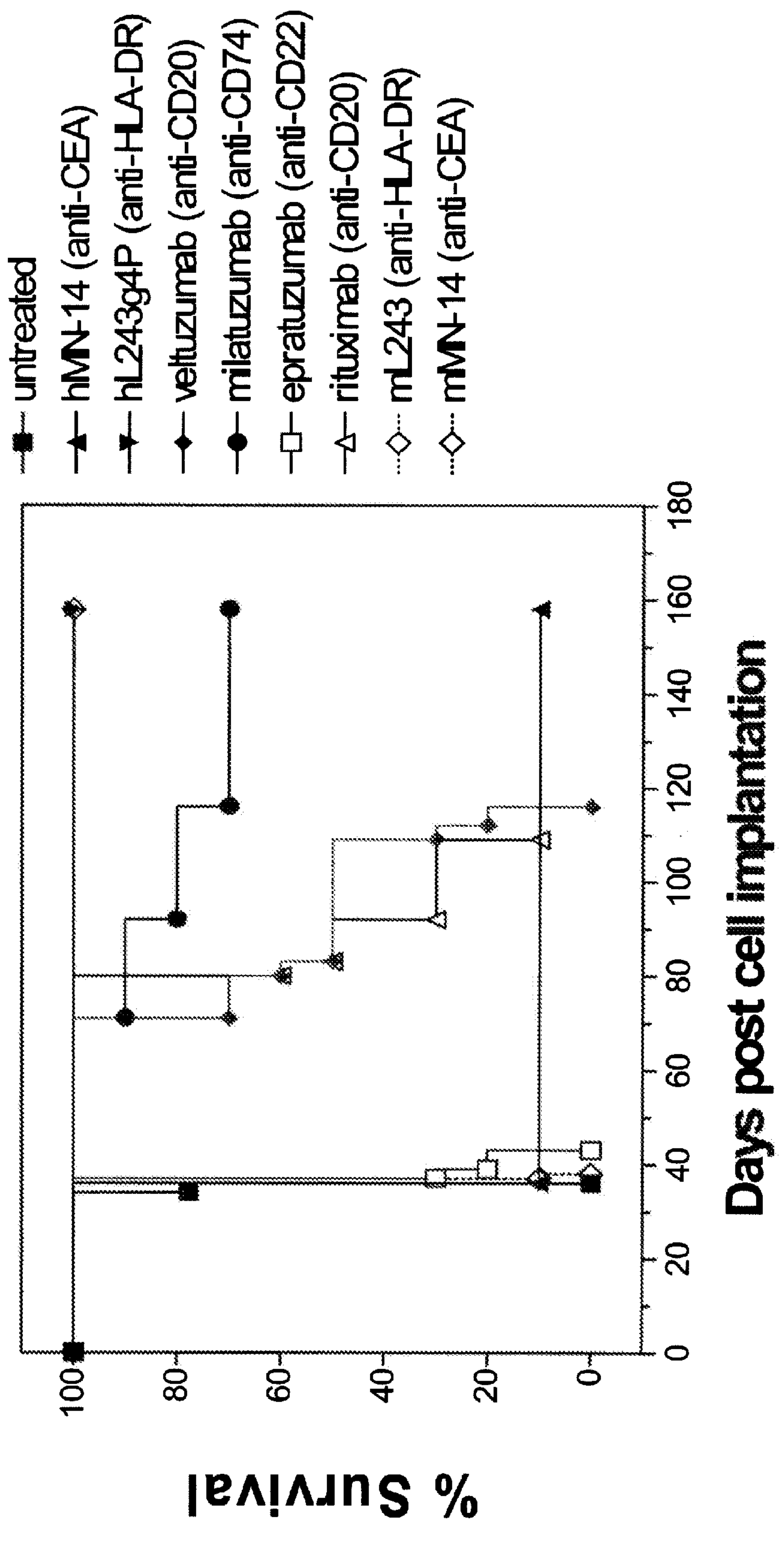
FIG. 26. Effect of different specificity antibodies on survival. 250 μg of the indicated antibodies was injected twice per week for 4 weeks, starting 1 day after injection of WSU-FSCCL tumor cells.

The comparative effect of the different specificity antibodies on survival of mice injected with WSU-FSCCL tumor cells is shown in FIG. 26. The mL243 and hL243γ4P antibodies produced a significant increase in survival compared to the other antibodies tested.

We examined the reactivity and cytotoxicity of hL243γ4P on a panel of leukemia cell lines. hL243γ4P bound to the cell surface of 2/3 AML, 2/2 mantle cell, 4/4 ALL, 1/1 hairy cell leukemia, and 2/2 CLL cell lines, but not on the 1 CML cell line tested. Cytotoxicity assays demonstrated that hL243γ4P was toxic to 2/2 mantle cell, 2/2 CLL, 3/4 ALL, and 1/1 hairy cell leukemia cell lines, but did not kill 3/3 AML cell lines despite positive staining. As expected, the CML cell line was also not killed by hL243γ4P.

Additional comparative data for different antibodies tested against a variety of NHL cell lines is presented in Table 9. Table 10 shows the relative expression of HLA-DR compared with CD74, CD22 and CD20 in different tumor types. Table 11 illustrates the relative cytotoxicity of hL243γ4P compared to other anti-B cell mAbs in different tumor types. The percent of untreated values in MTT assay are shown. Highlighted values represent a significant decrease from untreated ($P<0.05$). HLA-DR is expressed on all B-lymphoma and leukemia tested cell lines at markedly higher levels than CD20, CD22, and CD74. Despite positive staining AML cell lines are not killed by hL243g4P. Variation in expression and cytotoxicity profiles between the mAbs suggests that combination therapies may yield greater effects than the mAbs given singly.

Figure 27:
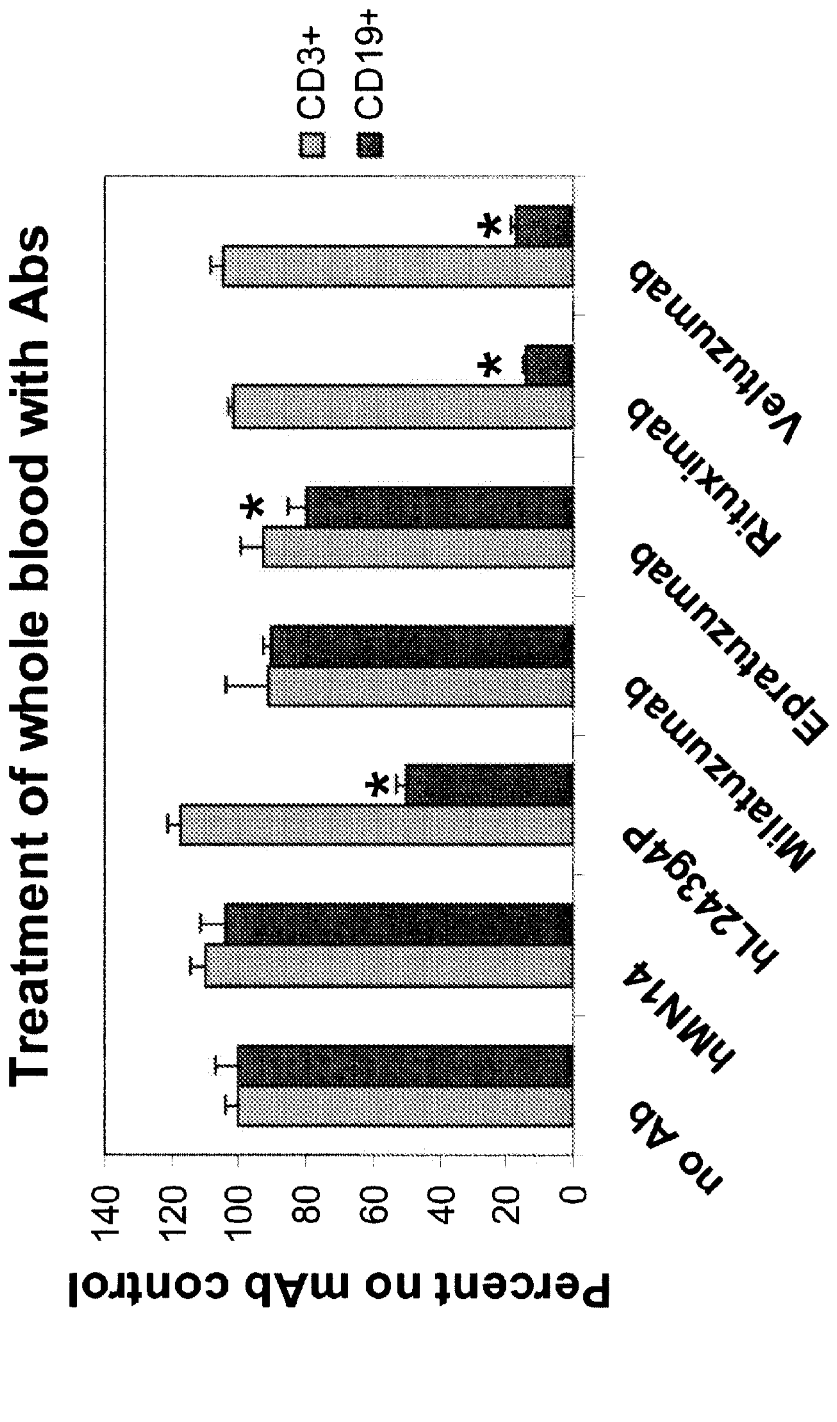
FIG. 27. Ex vivo effects of mAbs on whole blood. Heparinized whole blood of healthy volunteers was incubated with mAbs then assayed by flow cytometry. Data are shown as % of untreated control. Error bars, SD of 3 replicates. *, P<0.05 relative to no mAb control.

FIG. 27 illustrates the ex vivo effects of various antibodies on whole blood. hL243γ4P resulted in significantly less B cell depletion than rituximab and veltuzumab, consistent with an earlier report (Nagy, et al, J Mol Med 2003; 81:757-65) which suggested that anti-HLA-DR mAbs kill activated, but not resting normal B cells, in addition to tumor cells. This suggests a dual requirement for both MHC-II expression and cell activation for antibody-induced death, and implies that because the majority of peripheral B cells are resting, the potential side effect due to killing of normal B cells may be minimal. T-cells are unaffected.

Figure 28:
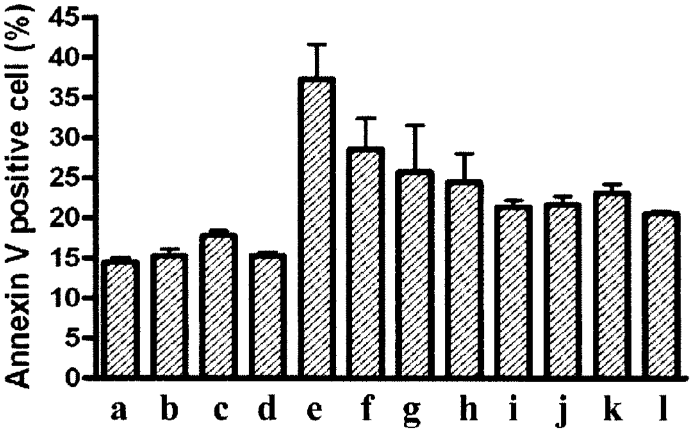
FIG. 28. Effect of ERK, JNK and ROS inhibitors on hL234g4P mediated apoptosis in Raji cells.

The effects of ERK, JNK and ROS inhibitors on hL243γ4P mediated apoptosis in Raji cells is shown in FIG. 28. hL243γ4P cytotoxicity correlates with activation of ERK and JNK signaling and differentiates the mechanism of action of hL243γ4P cytotoxicity from that of anti-CD20 mAbs. hL243γ4P also changes mitochondrial membrane potential and generates ROS in Raji cells (not shown). Inhibition of ERK, JNK, or ROS by specific inhibitors partially abrogates the apoptosis. Inhibition of 2 or more pathways abolishes the apoptosis.

These data demonstrate that hL243g4P may be useful in the treatment of mantle cell lymphoma, ALL, hairy cell leukemia, and CLL, as well as NHL and multiple myeloma.

TABLE 1

Comparison of binding of humanized and murine MAbs on Namalwa

| Humanized MAbs | GEO MEAN Fluorescence 2nd Ab: FITC GAH | Murine MAbs | GEO MEAN Fluorescence 2nd Ab: FITC GAM |
|---|---|---|---|
| none | 2.52 | none | 2.91 |
| HMN14 | 2.49 | Ag8 | 3.64 |
| hRS7 | 2.47 | MN14 | 3.32 |
| hLL1 | 10.06 | RS7 | 3.39 |
| hLL2 | 6.76 | LL1 | 17.31 |
| hA20 | 6.28 | LL2 | 10.46 |
| Rituximab | 7.33 | 1F5 | 3.83 |
| HL243 | 324.16 | m2B8 | 6.16 |
| | | L243 | 594.96 |

TABLE 2

Phenotyping cell lines
(Binding of humanized or chimeric MAbs on B cell lines by FACS Assay)
Indirect assay using FITC-GAH Fc 2nd Ab staining

| | Geometric Mean Fluorescence | | | | | | |
|---|---|---|---|---|---|---|---|
| | none | hMN14 | hLL1 | hA20 | | Rituximab | hL243 |
| Namalwa | 2.5 | 2.36 | 7.81 | 6.4 | 10.11 | 14.12 | 260.8 |
| SU-DHL-6 | 4.6 | 4.94 | 17.29 | 11 | 1199.34 | 1308.89 | 572.2 |
| WSU-FSCCL | 2.6 | 2.66 | 8.66 | 4.1 | 8.91 | 12.45 | 466.7 |
| Raji | 6.8 | 6.96 | 95.1 | 22. | 267.09 | 394.57 | 971.9 |
| Daudi | 3.1 | 3.16 | 48.77 | 51. | 240.96 | 380.45 | 937.4 |
| Ramos | 3.1 | 3.13 | 23.25 | 14. | 203.65 | 374.98 | 277.5 |

TABLE 3

Phenotyping dog lymphoma aspirate

| | % Positive | Mean FL |
|---|---|---|
| Murine MAbs | | |
| none | 3.85 | 3.37 |
| Ag8 | 2.81 | 3.04 |
| L243 | 77.77 | 10.41 |
| m2B8 | 2.61 | 3.11 |
| LL1 | 6.69 | 4.01 |
| LL2 | 5.05 | 3.73 |
| Humanized MAbs | | |
| none | 4.48 | 3.24 |
| hMN-14 | 4.63 | 3.24 |
| hL243 | 26.33 | 5.47 |
| hA2 | 3.96 | 3.25 |
| hLL1 | 4.71 | 3.33 |
| hLL2 | 4.85 | 3.37 |

TABLE 4

Binding of humanized or chimeric MAbs on B cell lines An indirect flow cytometry assay was performed using FITC-GAH Fc specific 2nd antibody staining

| | Geometric Mean Fluorescence | | | | | | |
|---|---|---|---|---|---|---|---|
| | none | anti-CEA (hMN14) | anti-CD74 (hLL1) | anti-CD22 (hLL2) | anti-CD20 (hA20) | anti-CD20 (Rituximab) | anti-HLA-DR (hL243γ4P) |
| Daudi | 3.2 | 3.2 | 48.8 | 517 | 241.0 | 380.5 | 937.4 |
| Namalwa | 2.6 | 2.4 | 7.8 | 64 | 10.1 | 14.1 | 260.9 |
| Raji | 6.9 | 7.0 | 95.1 | 226 | 267.1 | 394.6 | 972.0 |
| Ramos | 3.1 | 3.1 | 23.3 | 146 | 203.7 | 375.0 | 277.6 |
| RL | 2.4 | 2.8 | 7.9 | 51 | 127.5 | 147.8 | 112.2 |
| SU-DHL-6 | 4.6 | 4.9 | 17.3 | 11 | 1199.3 | 1308.9 | 572.3 |
| WSU-FSCCL | 2.7 | 2.7 | 8.7 | 42 | 8.9 | 12.5 | 466.8 |

TABLE 5

Summary of antiproliferative activity of MAbs with and without crosslinking (% Inhibition of 3-H-Thymidine uptake)

| | Rituximab + hL243 | Rituximab | hL243γ4P |
|---|---|---|---|
| **Antiproliferative activity of MAbs without crosslinking** | | | |
| Ramos | 18.2 ± 4.9 | −7.9 ± 3.6 (0.0001)[a] | 10.1 ± 11.9 (0.3619) |
| FSCCL | 75.9 ± 10.2 | 13.4 ± 12.3 (0.0028) | 78.9 ± 1.7 (0.6611) |
| Namalwa | 50.1 ± 1.1 | 13.8 ± 5.6 (0.0061) | 27.8 ± 3.3 (0.0038) |
| **Antiproliferative activity of MAbs in the presence of anti-human $2^{nd}$ Ab** | | | |
| Ramos | 69.0 ± 7.0 | 50.5 ± 9.4 (0.0519) | 56.8 ± 0.8 (0.0073) |
| FSCCL | 94.5 ± 0.9 | 28.1 ± 9.6 (0.0067) | 94.5 ± 0.8 (0.9984) |
| Namalwa | 58.1 ± 2.1 | 14.7 ± 7.0 (0.005) | 51.5 ± 3.0 (0.0416) |

[a]Numbers in parentheses represent P values of the single MAbs in comparison to the combination of rituximab + hL243γ4P

TABLE 6

Cleaved Caspase-3 assay

| | Cleaved caspase-3 (% above no MAb control) | | | | |
|---|---|---|---|---|---|
| | Humanized MAbs | | | murine MAbs | |
| | hL243g4P | hA2 | hMN-14 | mL243 | mMN-14 |
| No crosslinking | | | | | |
| Ramos | 26.9 | 3.2 | 0.8 | 15.8 | 3.9 |
| Namalwa | 18.4 | −0.1 | 0.2 | 9.4 | 0.5 |
| FSCCL | 46.4 | 0.7 | 0.3 | 26.2 | −0.7 |
| Daudi | 48.1 | 7.9 | 0.9 | 45.8 | 1.0 |
| RL | 22.5 | 1.5 | −0.1 | 18.2 | −0.3 |
| SU-DHL-6 | 52.2 | 30.9 | 2.3 | 46.5 | 0.2 |
| Raji | 22.5 | 1.5 | −0.1 | 18.2 | −0.3 |
| with 2nd Ab | | | | | |
| Ramos | 71.7 | 67.8 | 7.3 | 40.3 | 3.0 |
| Namalwa | 72.2 | 20.4 | 7.9 | 25.2 | −0.3 |
| FSCCL | 86.7 | 20.0 | 8.4 | 55.0 | 1.5 |
| Daudi | 68.9 | 72.0 | 2.9 | 51.2 | 0.0 |
| RL | 37.3 | 24.2 | 4.0 | 4.0 | 0.7 |
| SU-DHL-6 | 72.1 | 75.8 | 5.5 | 51.4 | −0.9 |
| Raji | 59.8 | 37.4 | 2.8 | 20.4 | −0.3 |

TABLE 7

P-AKT assay

| | % above no MAb control | | | | |
|---|---|---|---|---|---|
| | humanized MAbs | | | murine MAbs | |
| | hL243g4P | hA2 | hMN-14 | mL243 | mMN-14 |
| Namalwa | 8.4 | −2.8 | 1.3 | 3.5 | −4.4 |
| FSCCL | 25.1 | −1.4 | 3.9 | 16.3 | −1.7 |
| Daudi | 34.9 | 1.0 | −1.4 | 24.5 | −2.1 |
| RL | 5.9 | 1.8 | 0.0 | 1.3 | 1.3 |
| SU-DHL-6 | 29.8 | 0.2 | 1.2 | 26.1 | −0.5 |
| Raji | 5.1 | −0.9 | −1.6 | 17.2 | −4.2 |

TABLE 8

Characteristic phenotype of a canine lymphoma aspirate (150836).

| | % Positive | Mean FL |
|---|---|---|
| Murine Abs | | |
| none | 3.9 | 3.4 |
| Ag8 | 2.8 | 3.0 |
| L243 | 77.8 | 10.4 |
| 2B8 (anti-CD20) | 2.6 | 3.1 |
| LL1 (anti-CD74) | 6.7 | 4.0 |
| LL2 (anti-CD22) | 5.1 | 3.7 |
| Humanized mAbs | | |
| none | 4.5 | 3.2 |
| hMN-14 | 4.6 | 3.2 |
| IMMU-114 | 26.2 | 5.5 |
| hA20 (anti-CD20) | 4.0 | 3.3 |
| hLL1 (anti-CD74) | 4.7 | 3.3 |
| hLL2 (anti-CD22) | 4.9 | 3.4 |

TABLE 9

Comparative reaction of different specificity antibodies with NHL cell lines

| | NHL Cell Line | | | | |
|---|---|---|---|---|---|
| Murine MAb | RL | Raji | Ramos | SU-DHL6 | Daudi |
| Ag8 (neg control) | 3.3 | 2.6 | 4.6 | 2.5 | 6.9 |
| L243 (HLA-DR) | 157.2 | 623.7 | 92.9 | 370.3 | 435.5 |
| LL1 (CD74) | 7.5 | 63.8 | 12.3 | 27.9 | 26.4 |
| LL2 (CD22) | 5.4 | 30.8 | 10.7 | 9.7 | 43.5 |
| 2B8 (CD20) | 46.7 | 102.7 | 64.2 | 148.8 | 101.5 |

TABLE 10

| Expression of HLA-DR compared to CD74, CD22 and CD20 (mean FL) | | | | | | | |
|---|---|---|---|---|---|---|---|
| | Cell line | No mAb | Ag8 (Isotype control) | L243 (HLA-DR) | LL1 (CD74) | LL2 (CD22) | 2B8 (CD20) |
| AML | GDM-1 | 16.8 | 20.1 | 1072.7 | 69.5 | 28.5 | 15.6 |
| | Kasumi-1 | 18.2 | 17.0 | 24.0 | 23.8 | 20.9 | 14.5 |
| | Kasumi-3 | 9.6 | 15.7 | 565.3 | 18.4 | 13.9 | 11.0 |
| MCL | Jeko-1 | 14.3 | 17.4 | 1895.0 | 32.7 | 25.0 | 454.8 |
| | Granta-519 | 15.3 | 16.9 | 2107.9 | 50.8 | 28.6 | 677.2 |
| ALL | RS4; 11 | 6.4 | 8.6 | 152.0 | 24.3 | 20.9 | 11.5 |
| | REH | 3.9 | 3.9 | 2088.4 | 61.1 | 16.8 | 23.5 |
| | 697 | 4.9 | 5.6 | 259.3 | 20.6 | 15.9 | 6.9 |
| | MN60 | 8.1 | 10.5 | 1221.1 | 25.9 | 17.1 | 162.4 |
| CML | K562 | 3.2 | 4.1 | 4.9 | 7.0 | 4.3 | 4.3 |
| Hairy cell leukemia | HC-1 | 4.8 | 3.5 | 514.9 | 36.7 | 17.8 | 42.2 |
| CLL | MEC-1 | 4.7 | 6.0 | 1700.5 | 44.7 | 49.0 | 175.3 |
| | WAC | 15.8 | 14.4 | 787.5 | 43.6 | 20.1 | 275.4 |

TABLE 11

| Cytotoxicity of hL243γ4P compared to other anti-B cell mAbs | | | | | |
|---|---|---|---|---|---|
| | | GAH 2nd Ab | hL243γ4P (HLA-DR) | Milatuzumab (CD74) | Veltuzumab (CD20) |
| AML | GDM-1 | - | 105.9 ± 14.4 | 102.0 ± 15.2 | 100.3 ± 10.5 |
| | | + | 104.1 ± 10.0 | 128.9 ± 9.5 | 111.9 ± 14.5 |
| | Kasumi-1 | - | 92.1 ± 6.0 | 83.9 ± 5.2 | 88.1 ± 16.3 |
| | | + | 88.6 ± 10.6 | 88.1 ± 8.9 | 99.4 ± 4.6 |
| | Kasumi-3 | - | 120.4 ± 7.7 | 116.1 ± 7.3 | 112.3 ± 8.3 |
| | | + | 113.9 ± 9.9 | 123.3 ± 8.9 | 111.8 ± 18.0 |
| MCL | Jeko-1 | - | 41.3 ± 5.4 | 116.7 ± 10.1 | 124.1 ± 7.9 |
| | | + | 25.8 ± 1.7 | 33.1 ± 1.0 | 66.8 ± 3.0 |
| | Granta-519 | - | 78.8 ± 3.2 | 103.8 ± 5.7 | 94.6 ± 3.4 |
| | | + | 64.7 ± 2.2 | 64.7 ± 3.2 | 64.8 ± 1.6 |
| ALL | RS4;11 | - | 79.6 ± 3.7 | 102.0 ± 10.2 | 88.1 ± 10.6 |
| | | + | 90.8 ± 9.7 | 88.6 ± 5.3 | 106.9 ± 5.5 |
| | REH | - | 50.4 ± 5.0 | 79.1 ± 10.2 | 87.9 ± 7.1 |
| | | + | 29.4 ± 2.5 | 29.3 ± 2.1 | 94.7 ± 9.8 |
| | 697 | - | 90.8 ± 13.4 | 105.1 ± 8.2 | 115.0 ± 12.1 |
| | | + | 57.8 ± 3.9 | 59.3 ± 8.2 | 124.2 ± 7.6 |
| | MN60 | - | 34.9 ± 2.8 | 87.6 ± 14.9 | 92.1 ± 10.2 |
| | | + | 26.8 ± 2.5 | 34.9 ± 2.8 | 56.0 ± 2.0 |
| CML | K562 | - | 100.5 ± 7.8 | 100.3 ± 10.1 | 93.8 ± 12.8 |
| | | + | 124.8 ± 20.6 | 108.9 ± 7.4 | 99.8 ± 8.7 |
| hairy cell leukemia | HC-1 | - | 27.5 ± 2.1 | 120.5 ± 5.8 | 91.2 ± 10.8 |
| | | + | 16.9 ± 1.1 | 18.8 ± 1.3 | 48.7 ± 9.9 |
| CLL | MEC-1 | - | 68.8 ± 2.6 | 100.7 ± 8.2 | 99.1 ± 4.8 |
| | | + | 29.6 ± 2.0 | 51.7 ± 2.0 | 62.7 ± 5.8 |
| | WAC | - | 54.4 ± 7.3 | 97.0 ± 11.5 | 101.6 ± 16.9 |
| | | + | 41.1 ± 3.5 | 50.5 ± 6.9 | 62.3 ± 8.2 |

What is claimed is:

1. A method of treating hematopoietic cancer comprising:
   a) administering to a subject with hematopoietic cancer a humanized anti-HLA-DR antibody or antigen-binding fragment thereof comprising the heavy chain complementarity determining region (CDR) sequences CDR1 (NYGMN (SEQ ID NO: 39)), CDR2 (WINTYTREPTYADDFKG (SEQ ID NO: 40)), and CDR3 (DITAVVPTGFDY (SEQ ID NO: 41)) and the light chain CDR sequences CDR1 (RASENIYSNLA (SEQ ID NO: 42)), CDR2 (AASNLAD (SEQ ID NO: 43)), and CDR3 (QHFWTTPWA (SEQ ID NO: 44));
   wherein the humanized antibody is an IgG4 antibody comprising a Ser241Pro mutation, further comprising light chain murine L243 FR residues R37, K39, V48, F49, and G100 and heavy chain murine L243 FR residues F27, K38, K46, A68, and F91 and wherein the hematopoietic cancer is selected from the group consisting of indolent forms of B-cell lymphoma, aggressive forms of B-cell lymphoma, chronic lymphatic leukemia, acute lymphatic leukemia, multiple myeloma, Hodgkin lymphoma, Non-Hodgkin's lymphoma, Burkitt lymphoma, and hairy cell leukemia.

2. The method of claim 1, wherein said humanized anti-HLA-DR antibody has a higher affinity for HLA-DR than a murine L243 antibody that comprises the heavy chain CDR sequences CDR1 (NYGMN (SEQ ID NO: 39)), CDR2 (WINTYTREPTYADDFKG (SEQ ID NO: 40)), and CDR3 (DITAVVPTGFDY (SEQ ID NO: 41)) and the light chain CDR sequences CDR1 (RASENIYSNLA (SEQ ID NO: 42)), CDR2 (AASNLAD (SEQ ID NO: 43)), and CDR3 (QHFWTTPWA (SEQ ID NO: 44)).

3. The method of claim 1, wherein said humanized anti-HLA-DR antibody is a naked antibody.

4. The method of claim 3, further comprising:
   b) administering to said subject at least one therapeutic agent selected from the group consisting of an antibody, an antibody fragment, an immunoconjugate, an immunomodulator, a hormone, a cytotoxic agent, an enzyme, a hormone, a cytokine, an anti-angiogenic agent, a pro-apoptosis agent, a photodynamic agent, a drug and a toxin.

5. The method of claim 4, wherein the antibody, antibody fragment, or immunoconjugate binds to an antigen selected from the group consisting of A3, BrE3-antigen, CD1, CD1a, CD3, CD5, CD15, CD19, CD20, CD21, CD22, CD23, CD25, CD30, CD45, CD74, CD79a, CD80, HLA-DR, NCA95, NCA90, HCG, CEACAM-5, CEACAM-6, CSAp, EGFR, EGP-1, EGP-2, Ep-CAM, Ba 733, HER2/neu, hypoxia inducible factor (HIF), KC4-antigen, KS-1 antigen, KS1-4, Le-Y, macrophage inhibition factor (MIF), MAGE, MUC1, MUC2, MUC3, MUC4, MUC16, PAM-4-antigen, PSA, PSMA, RS5, S100, TAG-72, p53, tenascin, IL-6, IL-8, insulin growth factor-1 (IGF-1), Tn antigen, VEGF, 17-1A-antigen, ED-B fibronectin, HM1.24, VEGF, ILGF, placental growth factor and carbonic anhydrase IX.

6. The method of claim 4, wherein the drug is selected from the group consisting of 5-fluorouracil, aplidin, azaribine, anastrozole, anthracyclines, bendamustine, bleomycin, bortezomib, bryostatin-1, busulfan, calicheamycin, camptothecin, carboplatin, 10-hydroxycamptothecin, carmustine, celecoxib, chlorambucil, cisplatinum, Cox-2 inhibitors, irinotecan (CPT-11), SN-38, carboplatin, cladribine, camptothecans, cyclophosphamide, cytarabine, dacarbazine, docetaxel, dactinomycin, daunorubicin, doxorubicin, 2-pyrrolinodoxorubicine (2P-DOX), cyano-morpholino doxorubicin, doxorubicin glucuronide, epirubicin glucuronide, estramustine, epipodophyllotoxin, estrogen receptor binding agents, etoposide (VP16), etoposide glucuronide, etoposide phosphate, floxuridine (FUdR), 3′,5′—O-dioleoyl-FudR (FUdR-dO), fludarabine, flutamide, farnesyl-protein transferase inhibitors, gemcitabine, hydroxyurea, idarubicin, ifosfamide, L-asparaginase, lenalidomide, leucovorin, lomustine, mechlorethamine, melphalan, mercaptopurine, 6-mercaptopurine, methotrexate, mitoxantrone, mithramycin, mitomycin, mitotane, navelbine, nitrosourea, plicamycin, procarbazine, paclitaxel, pentostatin, PSI-341, raloxifene, semustine, SN-38, streptozocin, tamoxifen, temazolomide (an aqueous form of DTIC), transplatinum, thalidomide, thioguanine, teniposide, topotecan, uracil mustard, vinorelbine, vinblastine, vincristine and vinca alkaloids.

7. The method of claim 4, wherein the toxin is selected from the group consisting of ricin, abrin, alpha toxin, saporin, ribonuclease (RNase), onconase, DNase I, Staphylococcal enterotoxin-A, pokeweed antiviral protein, gelonin, diphtheria toxin, Pseudomonas exotoxin and Pseudomonas endotoxin.

8. The method of claim 4, wherein the anti-angiogenic agent is selected from the group consisting of angiostatin, baculostatin, canstatin, maspin, anti-VEGF antibodies, anti-P1GF peptides and antibodies, anti-vascular growth factor antibodies, anti-Flk-1 antibodies, anti-Flt-1 antibodies and peptides, anti-Kras antibodies, anti-cMET antibodies, anti-MIF (macrophage migration-inhibitory factor) antibodies, laminin peptides, fibronectin peptides, plasminogen activator inhibitors, tissue metalloproteinase inhibitors, interferons, interleukin-12, IP-10, Gro-β, thrombospondin, 2-methoxy-oestradiol, proliferin-related protein, carboxyamidotriazole, CM101, pentosan polysulphate, angiopoietin-2, interferon-alpha, herbimycin A, PNU145156E, 16K prolactin fragment, roquinimex, thalidomide, pentoxifylline, genistein, TNP-470, endostatin, paclitaxel, accutin, angiostatin, cidofovir, vincristine, bleomycin, AGM-1470, platelet factor 4 and minocycline.

9. The method of claim 4, wherein the immunomodulator is selected from the group consisting of erythropoietin, thrombopoietin, granulocyte-colony stimulating factor (G-CSF), granulocyte macrophage-colony stimulating factor (GM-CSF), interferon-α, interferon-β, interferon-γ, human growth hormone, N-methionyl human growth hormone, bovine growth hormone, parathyroid hormone, thyroxine, insulin, proinsulin, relaxin, prorelaxin, follicle stimulating hormone (FSH), thyroid stimulating hormone (TSH), luteinizing hormone (LH), hepatic growth factor, prostaglandin, fibroblast growth factor, prolactin, placental lactogen, tumor necrosis factor-a, tumor necrosis factor-β, mullerian-inhibiting substance, mouse gonadotropin-associated peptide, inhibin, activin, vascular endothelial growth factor, integrin, NGF-β, platelet-growth factor, TGF-α, TGF-β, insulin-like growth factor-I, insulin-like growth factor-II, macrophage-CSF (M-CSF), IL-1, IL-1α, IL-2, IL-3, IL-4, IL-5, IL-6, IL-7, IL-8, IL-9, IL-10, IL-11, IL-12, IL-13, IL-14, IL-15, IL-16, IL-17, IL-18, IL-21, IL-25, LIF, kit-ligand, angiostatin, thrombospondin, endostatin, tumor necrosis factor and lymphotoxin (LT).

10. The method of claim 1, wherein said humanized anti-HLA-DR antibody is attached to at least one therapeutic agent.

11. The method of claim 10, wherein the therapeutic agent is selected from the group consisting of a drug, a toxin, an enzyme, a radionuclide, an immunomodulator, a cytokine, a hormone, an antibody or fragment thereof, an anti-angiogenic agent, a cytotoxic agent, a pro-apoptosis agent, and a photodynamic agent.

12. The method of claim 11, wherein the drug is selected from the group consisting of 5-fluorouracil, aplidin, azaribine, anastrozole, anthracyclines, bendamustine, bleomycin, bortezomib, bryostatin-1, busulfan, calicheamycin, camptothecin, carboplatin, 10-hydroxycamptothecin, carmustine, celecoxib, chlorambucil, cisplatinum, Cox-2 inhibitors, irinotecan (CPT-11), SN-38, carboplatin, cladribine, camptothecans, cyclophosphamide, cytarabine, dacarbazine, docetaxel, dactinomycin, daunorubicin, doxorubicin, 2-pyrrolinodoxorubicine (2P-DOX), cyano-morpholino doxorubicin, doxorubicin glucuronide, epirubicin glucuronide, estramustine, epipodophyllotoxin, estrogen receptor binding agents, etoposide (VP16), etoposide glucuronide, etoposide phosphate, floxuridine (FUdR), 3',5'—O-dioleoyl-FudR (FUdR-dO), fludarabine, flutamide, farnesyl-protein transferase inhibitors, gemcitabine, hydroxyurea, idarubicin, ifosfamide, L-asparaginase, lenalidomide, leucovorin, lomustine, mechlorethamine, melphalan, mercaptopurine, 6-mercaptopurine, methotrexate, mitoxantrone, mithramycin, mitomycin, mitotane, navelbine, nitrosourea, plicamycin, procarbazine, paclitaxel, pentostatin, PSI-341, raloxifene, semustine, SN-38, streptozocin, tamoxifen, temazolomide (an aqueous form of DTIC), transplatinum, thalidomide, thioguanine, teniposide, topotecan, uracil mustard, vinorelbine, vinblastine, vincristine and vinca alkaloids.

13. The method of claim 11, wherein the drug is SN-38.

14. The method of claim 11, wherein the toxin is selected from the group consisting of ricin, abrin, saporin, ribonuclease (RNase), onconase, DNase I, Staphylococcal enterotoxin-A, pokeweed antiviral protein, gelonin, diphtheria toxin, Pseudomonas exotoxin and Pseudomonas endotoxin.

15. The method of claim 11, wherein the anti-angiogenic agent is selected from the group consisting of angiostatin, baculostatin, canstatin, maspin, anti-VEGF antibodies, anti-P1GF peptides and antibodies, anti-vascular growth factor antibodies, anti-Flk-1 antibodies, anti-Flt-1 antibodies and peptides, anti-Kras antibodies, anti-cMET antibodies, anti-MIF (macrophage migration-inhibitory factor) antibodies, laminin peptides, fibronectin peptides, plasminogen activator inhibitors, tissue metalloproteinase inhibitors, interferons, interleukin-12, IP-10, Gro-β, thrombospondin, 2-methoxyoestradiol, proliferin-related protein, carboxyamidotriazole, CM101, pentosan polysulphate, angiopoietin-2, interferon-alpha, herbimycin A, PNU145156E, 16K prolactin fragment, roquinimex, thalidomide, pentoxifylline, genistein, TNP-470, endostatin, paclitaxel, accutin, angiostatin, cidofovir, vincristine, bleomycin, AGM-1470, platelet factor 4 and minocycline.

16. The method of claim 11, wherein the immunomodulator is selected from the group consisting of erythropoietin, thrombopoietin, granulocyte-colony stimulating factor (G-CSF), granulocyte macrophage-colony stimulating factor (GM-CSF), interferon-α, interferon-β, interferon-γ, human growth hormone, N-methionyl human growth hormone, bovine growth hormone, parathyroid hormone, thyroxine, insulin, proinsulin, relaxin, prorelaxin, follicle stimulating hormone (FSH), thyroid stimulating hormone (TSH), luteinizing hormone (LH), hepatic growth factor, prostaglandin, fibroblast growth factor, prolactin, placental lactogen, tumor necrosis factor-α, tumor necrosis factor-β, mullerian-inhibiting substance, mouse gonadotropin-associated peptide, inhibin, activin, vascular endothelial growth factor, integrin, NGF-β, platelet-growth factor, TGF-α, TGF-β, insulin-like growth factor-I, insulin-like growth factor-II, macrophage-CSF (M-CSF), IL-1, IL-1α, IL-2, IL-3, IL-4, IL-5, IL-6, IL-7, IL-8, IL-9, IL-10, IL-11, IL-12, IL-13, IL-14, IL-15, IL-16, IL-17, IL-18, IL-21, IL-25, LIF, kit-ligand, angiostatin, thrombospondin, endostatin, tumor necrosis factor and lymphotoxin (LT).

17. The method of claim 11, wherein the radionuclide is selected from the group consisting of $^{18}F$, $^{32}P$, $^{33}P$, $^{45}Ti$, $^{47}Sc$, $^{52}Fe$, $^{59}Fe$, $^{62}Cu$, $^{64}Cu$, $^{67}Cu$, $^{67}Ga$, $^{68}Ga$, $^{75}Se$, $^{77}As$, $^{86}Y$, $^{89}Sr$, $^{89}Zr$, $^{90}Y$, $^{94}Tc$, $^{94m}Tc$, $^{99}Mo$, $^{99m}Tc$, $^{105}Pd$, $^{105}Rh$, $^{111}Ag$, $^{111}In$, $^{123}I$, $^{124}I$, $^{125}I$, $^{131}I$, $^{142}Pr$, $^{143}Pr$, $^{149}Pm$, $^{153}Sm$, $^{154-158}Gd$, $^{161}Tb$, $^{166}Dy$, $^{166}Ho$, $^{169}Er$, $^{175}Lu$, $^{177}Lu$, $^{186}Re$, $^{188}Re$, $^{189}Re$, $^{194}Ir$, $^{198}Au$, $^{199}Au$, $^{211}At$, $^{211}Pb$, $^{212}Bi$, $^{212}Pb$, $^{213}Bi$, $^{223}Ra$, $^{225}Ac$, and an alpha-emitting radionuclide.

18. The method of claim 5, wherein the administration of a combination of said humanized anti-HLA-DR antibody with an anti-CD20 antibody inhibits proliferation of lymphoma cells more than either anti-HLA-DR antibody or anti-CD20 antibody alone.

19. The method of claim 1, wherein the subject is a human subject.

20. The method of claim 1, wherein the hematopoietic cancer is non-Hodgkin's lymphoma.

21. The method of claim 1 wherein the humanized anti-HLA-DR antibody or antigen-binding fragment thereof is administered intravenously, subcutaneously, or intramuscularly at a dose of between 20 and 2000 mg.

* * * * *